US007867724B2

(12) United States Patent
Alexandru et al.

(10) Patent No.: US 7,867,724 B2
(45) Date of Patent: Jan. 11, 2011

(54) COMPOSITIONS AND METHOD OF TREATING HYPOXIA-ASSOCIATED DISEASES

(75) Inventors: Gabriela Alexandru, Pasadena, CA (US); Raymond Deshaies, Claremont, CA (US); Johannes Graumann, Planegg OT Martinsried (DE)

(73) Assignee: California Institute of Technology, Pasadena, CA (US)

( * ) Notice: Subject to any disclaimer, the term of this patent is extended or adjusted under 35 U.S.C. 154(b) by 59 days.

(21) Appl. No.: 12/291,155

(22) Filed: Nov. 5, 2008

(65) Prior Publication Data
US 2009/0192084 A1 Jul. 30, 2009

Related U.S. Application Data

(60) Provisional application No. 61/002,015, filed on Nov. 5, 2007.

(51) Int. Cl.
*G01N 33/53* (2006.01)
*G01N 33/543* (2006.01)

(52) U.S. Cl. ........................ 435/7.21; 435/7.1; 436/501; 436/506; 436/518; 422/50; 422/61; 530/300; 530/350; 424/9.1

(58) Field of Classification Search ........................ None
See application file for complete search history.

(56) References Cited

PUBLICATIONS

Alexandru et al., UBXD7 binds multiple ubiquitin ligases and implicates p97 in HIF1alpha turnover. *Cell.* 134(5): 804-816. (2008).
Bruderer et al., The AAA ATPase p97/VCP interacts with its alternative co-factors, Ufd1-Npl4 and p47, through a common bipartite binding mechanism. *J Biol Chem.* 279:49609-49616. (2004).
Ghislain et al., Cdc48p interacts with Ufd3p, a WD repeat protein required for ubiquitin-mediated proteolysis in *Saccharomyces cerevisiae. Embo J.* 15:4884-4899. (1996).
Graumann et al., Applicability of tandem affinity purification MudPIT to pathway proteomics in yeast. *Mol Cell Proteomics.* 3:226-237. (2004).
Hurley et al., Ubiquitin-binding domains. *Biochem J.* 399:361-372. (2006).
Ivan et al., The von Hippel-Lindau tumor suppressor protein. *Curr Opin Genet Dev.* 11:27-34. (2001).
Kondo et al., p47 is a cofactor for p97-mediated membrane fusion. *Nature.* 388:75-78. (1997).
Link et al., Direct analysis of protein complexes using mass spectrometry. *Nat Biotechnol.* 17:676-682. (1999).
Meyer et al., A complex of mammalian ufd1 and npl4 links the AAA-ATPase, p97, to ubiquitin and nuclear transport pathways. *Embo J.* 19:2181-2192. (2000).
Meyer et al., Direct binding of ubiquitin conjugates by the mammalian p97 adaptor complexes, p47 and Ufd1-Npl4. *Embo J.* 21:5645-5652. (2002).
Park et al., Ufd1 exhibits the AAA-ATPase fold with two distinct ubiquitin interaction sites. *Structure.* 13:995-1005. (2005).
Rape et al., Mobilization of processed, membrane-tethered SPT23 transcription factor by CDC48(UFD1/NPL4), a ubiquitin-selective chaperone. *Cell.* 107:667-677. (2001).
Richly et al., A series of ubiquitin binding factors connects CDC48/p97 to substrate multiubiquitylation and proteasomal targeting. *Cell.* 120:73-84. (2005).
Rouiller et al., Conformational changes of the multifunction p97 AAA ATPase during its ATPase cycle. *Nat Struct Biol.* 9:950-957. (2002).
Rumpf et al., Functional division of substrate processing cofactors of the ubiquitin-selective Cdc48 chaperone. *Mol Cell.* 21:261-269. (2006).
Ryu et al., Binding surface mapping of intra- and interdomain interactions among hHR23B, ubiquitin, and polyubiquitin binding site 2 of S5a. *J Biol Chem.* 278:36621-36627. (2003).
Schuberth et al., Membrane-bound Ubx2 recruits Cdc48 to ubiquitin ligases and their substrates to ensure efficient ER-associated protein degradation. *Nat Cell Biol.* 7:999-1006. (2005).
Shcherbik et al., Cdc48p$^{NP14p/Ufd1p}$ binds and segregates membrane-anchored/tethered complexes via a polyubiquitin signal present on the anchors. *Mol Cell.* 25:385-397. (2007).
Uchiyama et al. VCIP135, a novel essential factor for p97/p47-mediated membrane fusion, is required for Golgi and ER assembly in vivo. *J Cell Biol.* 159:855-866. (2002).
Wang et al., VCIP135 acts as a deubiquitinating enzyme during p97-p47-mediated reassembly of mitotic Golgi fragments. *J Cell Biol.* 164:973-978. (2004).
Ye Y. Diverse functions with a common regulator: Ubiquitin takes command of an AAA ATPase. *J Struct Biol.* (2006).
Ye et al., The AAA ATPase Cdc48/p97 and its partners transport proteins from the ER into the cytosol. *Nature.* 414:652-656. (2001).

(Continued)

*Primary Examiner*—Lisa V Cook
(74) *Attorney, Agent, or Firm*—Ropes & Gray LLP

(57) ABSTRACT

Hypoxia, a state of lower than normal tissue oxygen tension, has recently been implicated in a host of human diseases, including cancer, heart disease, and neurological disorders. Novel associations between p97 and other proteins, including UBX-domain-containing proteins (UBX-polypeptides), HIF1α, and a variety of E3 ligases are provided herein. The disclosure provides complexes comprising UBX-domain-containing polypeptides (UBX-polypeptides) and other polypeptides involved in the degradation of ubiquitinated proteins. In addition, the disclosure provides uses for active agents that modulate protein-protein complex formation between an UBX-polypeptide and its complementary-binding substrate. For example, the disclosure provides methods for treating or preventing hypoxia-related disorders or conditions in a patient or a cell by administration of an active agent that modulates the activity of an UBX-polypeptide and/or its complementary binding-substrate. Furthermore, the disclosure provides uses for active agents that modulate HIF1α activity; such agents may be used to modulate processes that are regulated by HIF1α. The disclosure also provides many screening assays to identify test agents that modulate complex formation between an UBX-polypeptide and its complementary-binding substrate or methods for evaluating modes of action and/or effects of active agents that have already been identified as modulators of an UBX-polypeptide and/or its complementary-binding substrate.

12 Claims, 11 Drawing Sheets

OTHER PUBLICATIONS

Ye et al., Function of the p97-Ufd1-Npl4 complex in retrotranslocation from the ER to the cytosol: dual recognition of nonubiquitinated polypeptide segments and polyubiquitin chains. *J Cell Biol.* 162:71-84. (2003).

Yuan et al., Solution structure and interaction surface of the C-terminal domain from p47: a major p97-cofactor involved in SNARE disassembly. *J Mol Biol.* 311:255-263. (2001).

Zhong et al., AAA ATPase p97/valosin-containing protein interacts with gp78, a ubiquitin ligase for endoplasmic reticulum-associated degradation. *J Biol Chem.* 279:45676-45684. (2004).

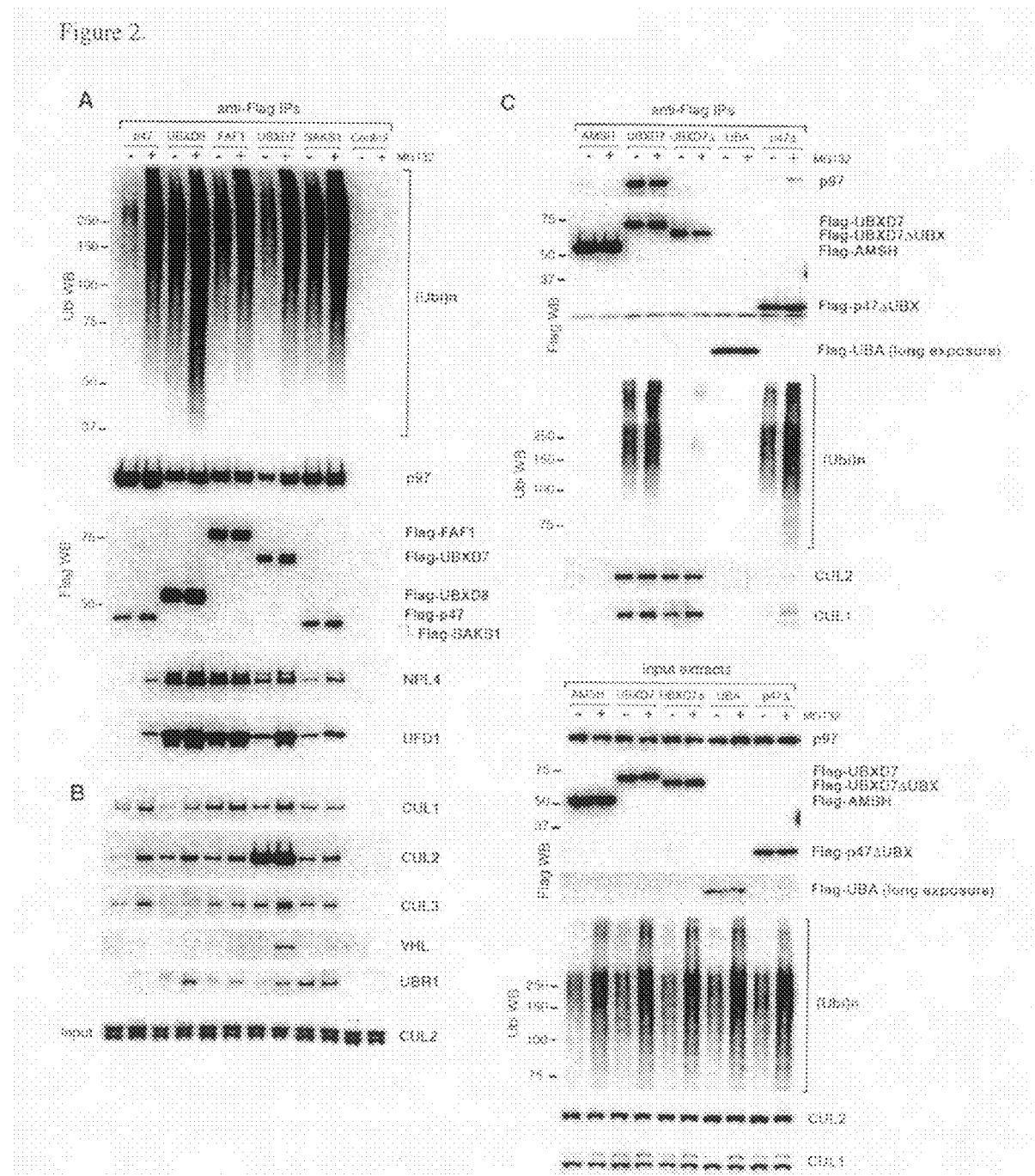

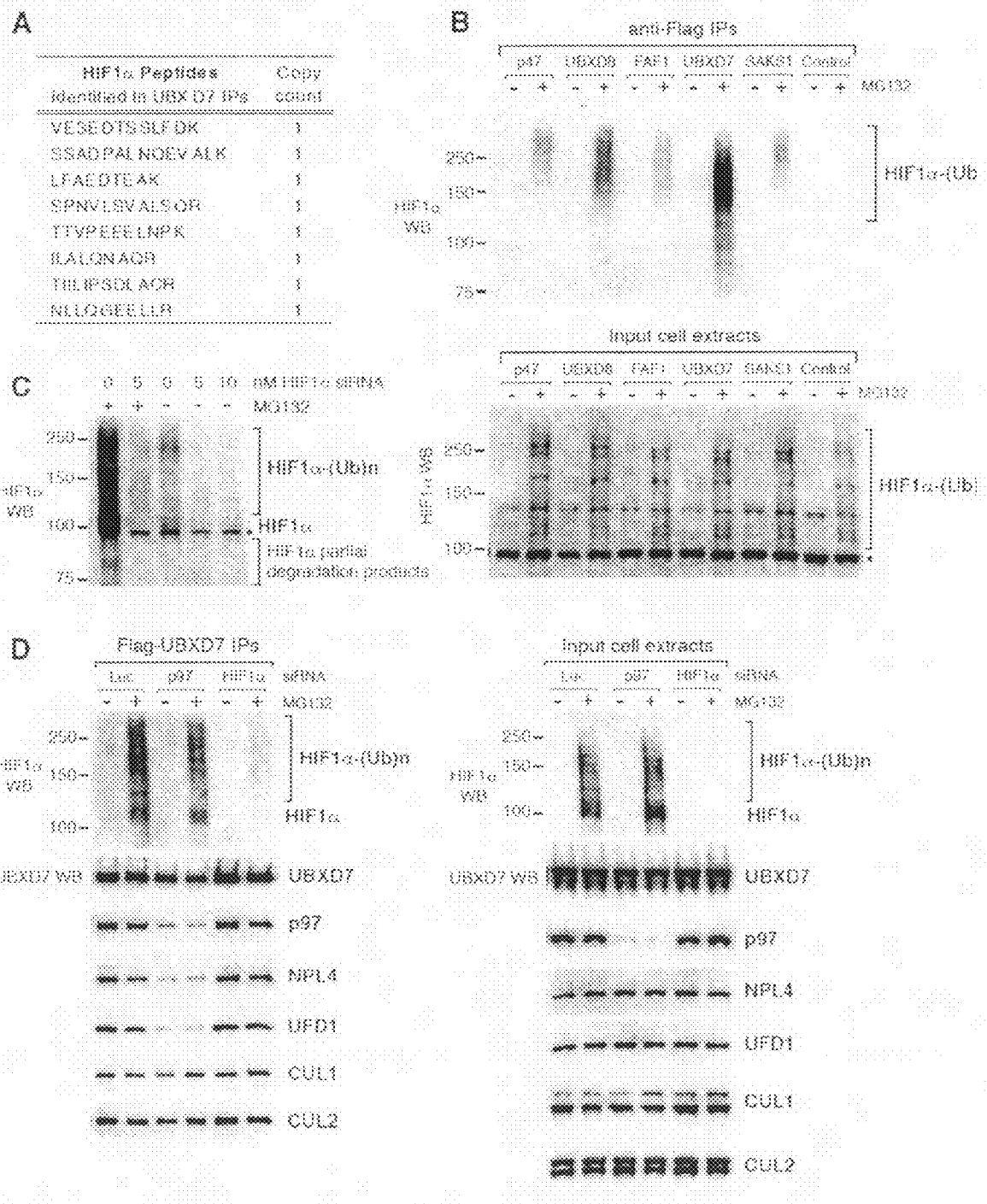

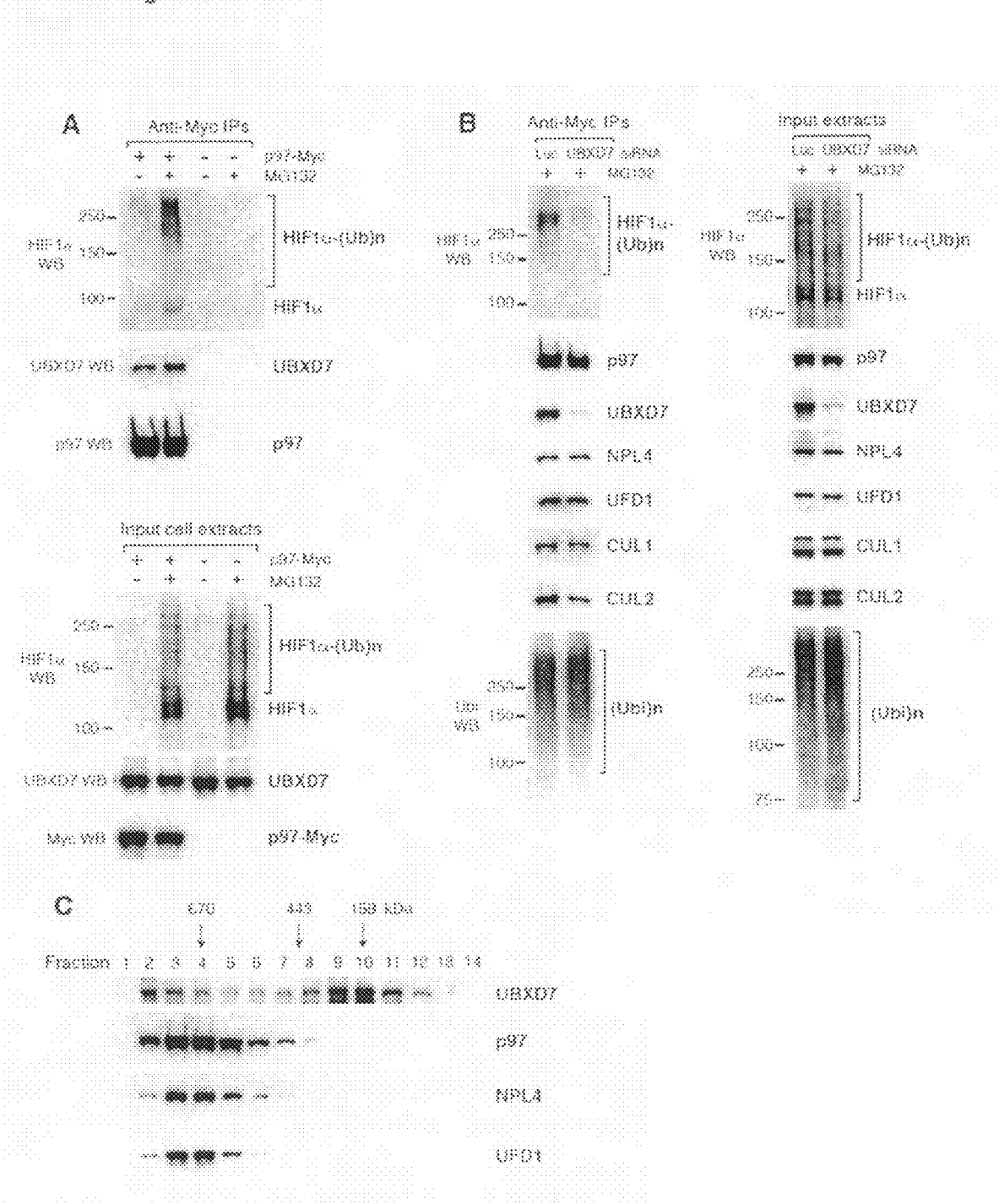

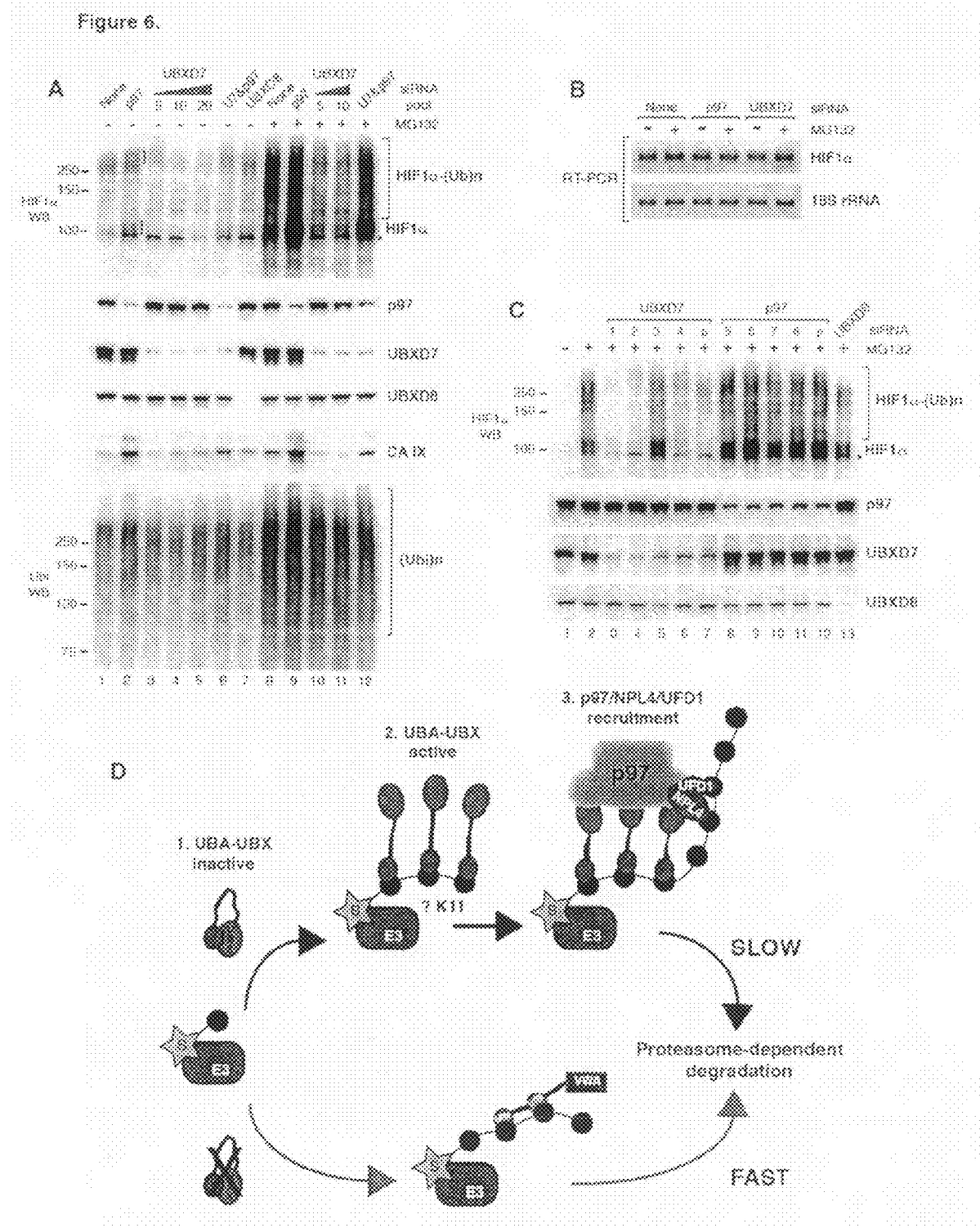

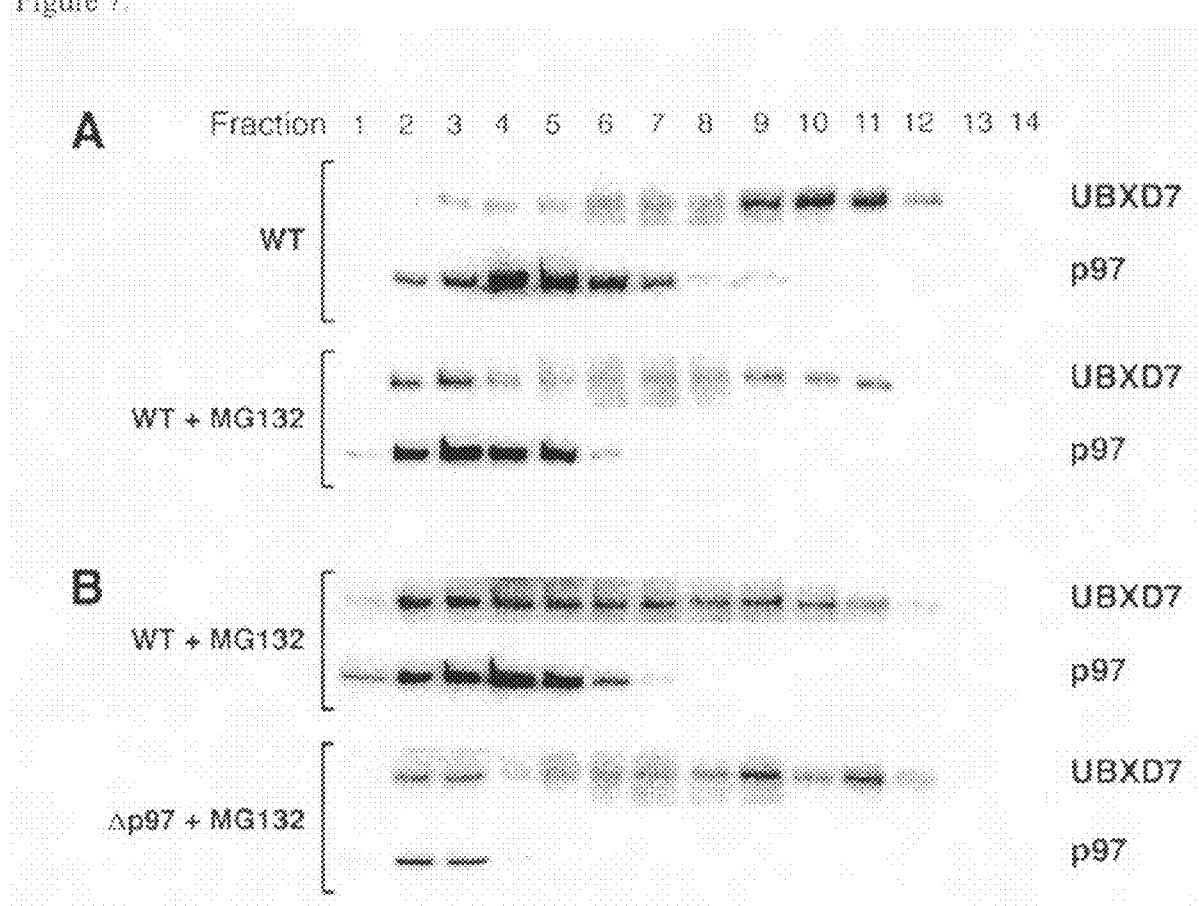

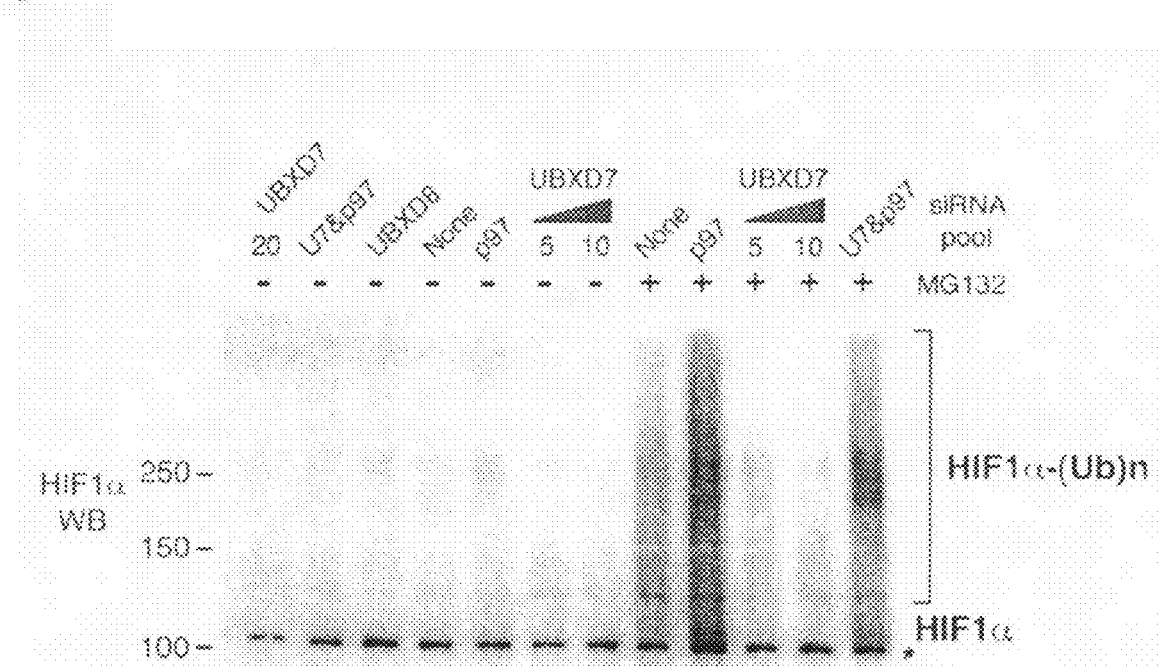

COMPOSITIONS AND METHOD OF TREATING HYPOXIA-ASSOCIATED DISEASES

RELATED APPLICATIONS

This application claims the benefit of U.S. Provisional Application No. 61/002,015, filed Nov. 5, 2007. The entire teachings of the referenced Provisional Application are incorporated herein by reference in their entirety.

BACKGROUND OF THE INVENTION

Hypoxia, a state of lower than normal tissue oxygen tension, has recently been implicated in a host of human diseases, including cancer, heart disease, and neurological disorders. An early response to tissue hypoxia is induction of hypoxia inducible factor (HIF), a basic helix-loop-helix (bHLH) PAS (Per/Arnt/Sim) transcriptional factor that mediates changes in gene expression in response to changes in cellular oxygen concentration. HIF is a heterodimer containing an oxygen-regulated alpha subunit (HIF1α) and a constitutively expressed beta subunit (HIFβ), also known as aryl-hydrocarbon receptor nuclear transporter (ARNT). As HIF1 activity has been implicated in numerous disorders, active agents that regulate the activity or stability of HIF1α represent attractive therapeutics for a variety of hypoxia-associated diseases or conditions. Compositions and methods for treating hypoxia-associated diseases or conditions are needed.

SUMMARY OF THE INVENTION

In certain embodiments, the disclosure provides complexes comprising UBX-domain-containing polypeptides (UBX-polypeptides) and other polypeptides involved in the degradation of ubiquitinated proteins. In addition, the disclosure provides uses for active agents that modulate protein-protein complex formation between an UBX-polypeptide and its complementary-binding substrate. For example, the disclosure provides, in part, methods for treating or preventing hypoxia-related disorders or conditions in a patient or a cell by administration of an active agent that modulates the activity of an UBX-polypeptide and/or its complementary binding-substrate. Furthermore, the disclosure provides uses for active agents that modulate HIF1α activity; such agents may be used to modulate processes that are regulated by HIF1α. The disclosure also provides many screening assays to identify test agents that modulate complex formation between an UBX-polypeptide and its complementary-binding substrate or methods for evaluating modes of action and/or effects of active agents that have already been identified as modulators of an UBX-polypeptide and/or its complementary-binding substrate. Other aspects and embodiments are presented below.

In certain embodiments, the disclosure provides complexes comprising at least a p97 polypeptide and a UBX-polypeptide. For example, the disclosure provides a complex comprising a p97 polypeptide, an UBX-polypeptide, and an E3-ligase or subunit of an E3-ligase. In certain embodiments, the UBX-polypeptide is an UBXD8, UBXD7, UBXD4, ASPL, UBXD6, UBXD3, UBXD2, or UBXD1 polypeptide. In certain embodiments, the E3-ligase is a Cullin-RING Ligase (e.g., CUL1, CUL2, CUL3, or CUL4) or other RING-type E3 ligase (e.g., gp78, UBR1, UBR2, UBR4, Praja 2, IAP2, Topors, RNF126), a HECT E3 ligase (e.g., EDD1/UBR5, UBE3A, HUWE1), or U-box ligase (e.g., UBE4B). In certain embodiments, the subunit of an E3-ligase is a Cullin 1, SKP1, RBX1, FBW1B, Cullin 2, Elongin B, Elongin C, VHL, Cullin 3, KLHL12, KLHL13, KLHL22, KLDC2, KLDC3, LG3BP, BTBD2, Cullin 4A, Cullin 4B, DDB1, VprBP, WDR26, WDR11, WDR68, WDR9, or BRWD3 polypeptide. The disclosure further provides a complex comprising a UBX-polypeptide and its complementary substrate. In a preferred embodiment, the disclosure provides a complex comprising UBXD7 and HIF1α. In certain aspects, the disclosure provides a complex comprising a p97 polypeptide, an UBX-polypeptide and a polypeptide that is the complementary substrate of the UBX-polypeptide. For example, the disclosure provides a complex comprising a p97 polypeptide, a UBXD7 polypeptide, and HIF1α polypeptide. In certain aspects, the disclosure provides a complex comprising a p97 polypeptide, an UBXD7 polypeptide, a HIF1α polypeptide and at least one polypeptide selected from a NPL4 polypeptide, a UFD1 polypeptide, and a CUL2 ubiquitin ligase or a subunit of a CUL2 ubiquitin ligase (e.g., Cullin 2, Elongin B, Elongin C, or VHL).

In certain embodiments, the disclosure provides methods for modulating a function or activity of an UBX-polypeptide by targeting and modulating the stability or activity of an UBX-polypeptide complex. In further embodiments, the disclosure provides methods for modulating a function or activity of the complementary-binding substrate of an UBX-polypeptide (e.g., HIF1α). As one of skill in the art can readily appreciate, a UBX-polypeptide may form different or higher-order complexes with other polypeptides involved in the degradation of ubiquitinated proteins (e.g., cellular ligases, etc.), depending on the biological context.

In one aspect, the disclosure provides methods for identifying an active agent that regulates a complex comprising a UBXD7 polypeptide and a HIF1α polypeptide. In certain embodiments, the method comprises providing an isolated or purified UBXD7 polypeptide and an isolated or purified HIF1α polypeptide in a reaction mixture, adding a test agent to the reaction mixture, and determining whether the test agent interferes with or promotes complex formation between the UBXD7 polypeptide and the HIF1α polypeptide. Often, an active agent identified in this manner will affect both UBXD7 and HIF1α activities. Optionally, the UBXD7-HIF1α complex may further comprise at least one additional polypeptide selected from a p97 polypeptide, a NPL4 polypeptide, a UFD1 polypeptide, and a CUL2 ubiquitin ligase or a subunit of a CUL2 ubiquitin ligase (e.g., a CUL2 polypeptide, an elongin B polypeptide, an elongin C polypeptide, or a VHL polypeptide). In a preferred embodiment, the test agent is a therapeutic active agent useful to treat or prevent a hypoxia-related disease or condition in a patient or a cell.

In one aspect, the disclosure provides methods for identifying an active agent that regulates a complex comprising an UBX-polypeptide and a p97 polypeptide. In certain embodiments, the method comprises providing an isolated or purified UBX-polypeptide and an isolated or purified p97 polypeptide in a reaction mixture, adding a test agent to the reaction mixture, and determining whether the test agent interferes with or promotes complex formation between the UBX-polypeptide and the p97 polypeptide. Often, an agent identified in this manner will affect both UBX-polypeptide and p97 activities. Optionally, the p97-UBX-polypeptide complex may further comprise at least one additional component selected from an E3-ligase, a subunit or polypeptide of an E3-ligase, or a substrate of the UBX-polypeptide. In a preferred embodiment, the test agent is a therapeutic active agent used to treat or prevent an E3-ligase- or ubiquitin-proteasome-associated disorder or condition in a patient or a cell.

In certain embodiments, one or more of the polypeptides of the complex includes a tag, which is a moiety that facilitates isolation of a tagged polypeptide. In certain embodiments one or more of the polypeptides of the complex includes a label, which is a moiety that facilitates detection and/or quantification of a labeled polypeptide. In some instances, a moiety can be used as both a label for polypeptide identification or detection and a tag for polypeptide isolation or purification.

In certain aspects, one or more of the polypeptides of the complex can be affixed to a solid substrate. A polypeptide of the invention may be affixed to a solid substrate through a direct interaction of a component of the solid substrate and the tag of the tagged polypeptide. In a specific embodiment, the solid substrate is a bead.

The determination of whether a test agent interferes with or promotes complex formation may be performed using one of the following methods: Fluorescence Resonance Energy Transfer (FRET), Fluorescence-Activated Cell Sorting (FACS), a surface plasmon resonance system, an electrophoresis mobility shift assay, an immunoassay for protein binding, and other protein-protein binding assays. Furthermore, the determination of whether a test agent interferes with or promotes complex formation may be determined using a device that is capable of measuring polypeptide complex formation or stability. In certain embodiments, the reaction mixture is at physiological oxygen levels (normoxia). In certain embodiments, the reaction mixture is hypoxic.

In one aspect, the disclosure provides methods for identifying an active agent that regulates a HIF1α activity in a cell. In certain embodiments, the method comprises providing a cell that is genetically modified to provide exogenous expression of an UBXD7 polypeptide and a HIF1α polypeptide, contacting the cell with a test agent, and determining whether the test agent inhibits or promotes an activity of HIF1α in the cell. Often, an agent identified in the manner will affect both UBXD7 and HIF1α activities. Optionally, the cell is further genetically modified to provide exogenous expression of at least one polypeptide selected from a p97 polypeptide, a NPL4 polypeptide, a UFD1 polypeptide, and a CUL2 ubiquitin ligase or a subunit of a CUL2 ubiquitin ligase (e.g., a CUL2 polypeptide, an elongin B polypeptide, an elgonin C polypeptide, or a VHL polypeptide). In a preferred embodiment, the test agent is a therapeutic active agent used to treat or prevent a hypoxia-related disease or condition in a patient or a cell.

In certain embodiments, the exogenous expression of the UBXD7 polypeptide and the HIF1α polypeptide is provide by an exogenous expression system. The exogenous expression system may include an inducible promoter. In certain embodiments, an inducible promoter will provide exogenous over-expression of a selected polypeptide (e.g., an UBXD7 polypeptide or a HIF1α polypeptide). In some embodiments, the cell is further contacted with an additional active agent that induces expression of the UBXD7 polypeptide and the HIF-1a polypeptide. In some aspects of the disclosure, the additional active agent activates or de-represses the inducible promoter either through direct interaction with elements at the promoter site or through a trans-activating factor. In certain embodiments, the expression system is an autonomously replicating expression vector. In certain embodiments, the expression system is integrated into the chromosomal DNA of the cell. In certain embodiments, the culture medium of the cell is at physiological oxygen levels (normoxia). In certain embodiments, the culture medium of the cell is hypoxic. The cell in which HIF1α activity is measured may be prokaryotic or eukaryotic cell or of an archaea lineage In certain embodiments, the method of determining whether the test agent inhibits or promotes HIF1α activity comprises measuring the expression of an HIF1α-regulated gene. In a preferred embodiment, the expression of an HIF1α regulated gene is determined by measuring transcription level of an HIF1α regulated gene. Method of measuring the transcription level of a HIF1α-regulated gene include, but are not limited to, Northern blotting, quantitative and qualitative RT-PCR, microarray, or any other method of quantifying the amount of a HIF1α-regulated gene transcript in the cell. In another preferred embodiment, the expression of an HIF1α-regulated gene is determined by measuring the expression of an HIF1α-reporter gene. The HIF1α-reporter gene may comprises a promoter region of an HIF1α-regulated gene (e.g., one contain the HRE binding motif) linked to a reporter gene. A reporter gene may be any expressed transcript that can be measured for enhanced or diminished activity. Furthermore, the determination of whether a test agent inhibits or promotes HIF1α activity may be determined using a device that is capable of measuring HIF1α activity in a cell. In some embodiments the test agent increases the expression of a HIF1α-regulated gene. In some embodiments the test agent decreases the expression of a HIF1α-regulated gene.

In some embodiments, the disclosure provides methods for treating or preventing a hypoxia-related disease or condition in a patient or a cell. The method of treatment may comprise the administration of a therapeutically-effective amount of an active agent to the patient or the cell that modulates a complex comprising a UBXD7 polypeptide and a HIF1α polypeptide. Optionally, the UBXD7-HIF1α complex may further comprises at least one polypeptide selected from a p97 polypeptide, a NPL4 polypeptide, a UFD1 polypeptide, and a CUL2 ubiquitin ligase or a subunit of a CUL2 ubiquitin ligase (e.g., a CUL2 polypeptide, an elongin B polypeptide, an elongin C polypeptide, or a VHL polypeptide). The active agent may stimulate or enhance formation of the complex. Alternatively, the active agent may inhibit or reduce formation of the complex, or even disrupt a formed complex. The active agent may modulate a HIF1α, an UBXD7, or a p97 activity in the cell or patient. In some embodiments, the active agent inhibits or reduces the HIF1α activity. In some embodiments, the active agent stimulates or enhances the HIF1α activity. In certain embodiments, an additional active agent is administered to the patient or cell. The additional active agent may be any therapeutic active agent useful to treat or prevent a hypoxia-related disease or condition in the patient or the cell. In certain embodiments, the patient or cell may be in a normal oxygen environment. In certain embodiments, the patient or cell may be in a hypoxic condition or state.

In certain embodiments, the hypoxia-related disease or condition that may be treated or prevented by the therapeutic active agent include cancer, cardiovascular disease, heart disease, stroke, macular degeneration, diabetic retinopathy, arthritis, inflammation, sepsis, sepsis-induced shock, renal disease, tissue fibrosis, gastrointestinal disease, neurodegenerative disease, respiratory distress syndrome, bronchopulmonary displasia, pulmonary hypertension, hypoxic pulmonary hypertension, severe pulmonary hypertension, COPD, diabetic retinopathy, diabetes, corneal neovascularization, pathogenic blood vessel growth, musculoskeletal disorder, ischemic-reperfusion injury, myocardial hypoxia, or cardiac hypertrophy.

In some embodiments, the disclosure provides, in part, methods of treating or preventing a ubiquitin proteasome-associated disorder in a patient or a cell. The method may comprise the administration of a therapeutically effective amount of an active agent to the patient or the cell that modulates a complex comprising a p97 polypeptide and a UBX-polypeptide. Optionally, the p97-UBX-polypeptide complex may further comprise at least one additional component selected from an E3-ligase, a subunit or polypeptide of an E3-ligase, or a substrate of the UBX-polypeptide. The active agent may stimulate or enhance formation of the complex. Alternatively, the active agent may inhibit or reduce formation of the complex, or even disrupt a formed complex. The active agent may modulate a p97 or a UBX-polypeptide activity in the cell or patient. In certain embodiments, an additional active agent is administered to the patient or cell. The additional active agent may be any therapeutic agent understood by one of skill in the art to treat or prevent a ubiquitin proteasome-associated disorder in a patient or a cell.

In certain embodiments, the ubiquitin proteasome-associated disorder that may be treated or prevented by the therapeutic active agent include serpinopathies, hemolytic anemia, Huntington's Disease, cystic fibrosis, amyotrophic lateral sclerosis, and Parkinson disease, amyloid-related diseases, Alzheimer's disease, transmissible spongiform encephalopathies, Diabetes Type II, dialysis-related amyloidosis, secondary amyloidosis, cerebral amyloid angiopathy, inclusion body myositis, Down's syndrome and Age-Related Macular Degeneration, spinobulbar muscular atrophy or Kennedy's disease, spinocerebellar ataxia type 1; spinocerebellar ataxia type 2, Machado-Joseph disease, spinocerebellar ataxia type 6, spinocerebellar ataxia type 7, spinocerebellar ataxia type 17, dentatorubral-pallidolu-sian atrophy, dystrophia myotonica, Pick's Disease, corticobasal degeneration, progressive supranuclear palsy, amyotrophic lateral sclerosis/parkinsonism dementia complex, Friedreich's ataxia, fragile XE mental retardation, fragile X syndrome, Wilson's Disease, chronic liver diseases, and cataracts.

In certain embodiments, the disclosure provides, in part, methods of treating or preventing an E3-ligase-associated disorder in a patient or a cell. The method may comprise the administration of a therapeutically effective amount of an active agent to the patient or the cell that modulates a complex comprising a p97 polypeptide and a UBX-polypeptide. Optionally, the p97-UBX-polypeptide complex may further comprise at least one additional component selected from an E3-ligase, a subunit or polypeptide of an E3-ligase, or a substrate of the UBX-polypeptide. The active agent may stimulate or enhance formation of the complex. Alternatively, the active agent may inhibit or reduce formation of the complex, or even disrupt a formed complex. The active agent may modulate a p97 or a UBX-polypeptide activity in the cell or patient. In certain embodiments, the patient or cell is administered an additional active agent. The additional active agent may be any therapeutic agent understood by one of skill in the art to treat or prevent an E3-ligase-associated disorder in a patient or a cell.

In certain embodiments, the E3-ligase-associated disorder that may be treated or prevented by the therapeutic active agent include but are not limited to Angelman disease, Juvenile recessive Parkinson, the APECED form of autoimmune polyendocrinopathy syndrome, con Hippel-Lindau syndrome, congenital polycytemia, Fanconi anemia, or breast or ovarian cancer.

In some embodiments, the disclosure provides, in part, methods of modifying the number of K11 linkages in a ubiquitin chain in a patient or a cell. The method may comprise the administration of an effective amount of an active agent to the patient or the cell that modulates a complex comprising a UBX-polypeptide and a p97 polypeptide. The active agent may decrease or increase the number of K11 linkages in an ubiquitin chain. In certain embodiments, modulation of the K11 linkages in a ubiquitin chain can be used treat or prevent disorders associated with misfolded or aggregated proteins that accumulate in particular cell types (e.g., neuronal and muscle cells). In certain embodiments, an active agent that modifies the K11 linkages of a ubiquitin chain may be used to treat or prevent a neurodegenerative disorder associated with protein aggregation in a patient (e.g., Alzheimer's, Huntington's disease, Machado-Joseph disease, Parkinson's disease, or Paget's disease of the bone and front temporal dementia).

In some embodiments, the disclosure provides, in part, methods for treating or preventing a hypoxia-related disease or condition in a patient or a cell by administration of an effective amount of an active agent that modulates a complex comprising a UBXD7 polypeptide and a HIF1α polypeptide provided the active agent is identified using at least one of the screening method described here within used to determine whether a test agent inhibits or promotes an activity of HIF1α in the cell. The screening methods that may be used have been previously described in detail. In certain embodiments, the method provides a cell, wherein the cell is genetically modified to provide exogenous expression of an UBXD7 polypeptide and a HIF1α polypeptide, contacting the cell with a test agent, and determining whether the test agent inhibits or promotes an activity of HIF1α in the cell.

In some embodiments, the test agent or active agent of the present invention is selected from a small molecule, an aptamer, a polypeptide, a polynucleotide, an antibody, an antisense nucleic acid or an siRNA construct. In certain embodiments, the test agent is an anti-UBXD7 antibody, an anti-p97 antibody, an anti-UBX-polypeptide antibody, an UBXD7 agonist, an UBXD7 antagonist, a p97 agonist, a p97 antagonist, a nucleic acid antisense to p97, a nucleic acid antisense to UBXD7, an siRNA construct that provides siRNA-mediated depletion of p97, a siRNA construct that provides siRNA-mediated depletion of UBXD7. In certain embodiments, the polypeptide is a purified, recombinant, or functional fragment of a p97 polypeptide. In some embodiments, the polypeptide is a purified, recombinant, or functional fragment of a UBXD7 polypeptide. In some embodiments, the test agent is a therapeutic active agent used to treat or prevent a hypoxia-related disease or condition, E3-ligase-associated disorder, or a ubiquitin proteasome-associated disorder in a patient or a cell.

BRIEF DESCRIPTION OF THE DRAWINGS

FIG. 2 shows that UBA-UBX proteins interact with ubiquitinated proteins destined for degradation and with various E3 ligases. (A, B) Flag-(UBA-UBX) proteins were immunoprecipitated from 293 cells treated for 2 h with DMSO or MG132. Cells expressing no Flag-tagged protein were used as negative control. Some of the endogenous proteins that coimmunoprecipitated were detected by western blotting using specific antibodies. CUL2 input levels are shown at the bottom of panel B. (C) The indicated Flag-tagged proteins were immunoprecipitated from HeLa cells treated with MG132 as above. AMSH, a protein that is not part of the p97 network, was used as negative control. UBXD7Δ and p47Δ are truncation mutants lacking the UBX domain. The UBA domain by itself was expressed at very low levels. The indicated proteins were detected using specific antibodies, in the immunoprecipitates (top) and in the input cell extracts (bottom). Ubi—ubiquitin

FIG. 4 shows that UBXD7 interacts with endogenous HIF1α independently of p97. (A) HIF1α peptides (SEQ ID NOS: 39-46, respectively in order of appearance) identified by mass spectrometry in Flag-UBXD7 immunoprecipitates from cells treated with MG132 for 2 h. (B) The Flag-(UBA-UBX) immunoprecipitates shown in FIG. 2A were separated by PAGE and blotted using HIF1α specific antibodies (top). The bottom panel shows equivalent HIF1α levels in the input cell extracts. (C) The specificity of HIF1α antibodies was tested on total cell extracts from HeLa cells treated with the indicated concentration of HIF1α siRNA, in the presence and in the absence of a 2 h treatment with MG132. A cross-reacting band partially overlapping with full-length HIF1α is indicated with *. (D) Flag-UBXD7 was immunoprecipitated from HeLa cells treated with 5 nM of the indicated siRNAs for 48 h. Where indicated, 20 μM MG132 was added for 2 h prior to harvesting the cells. The indicated proteins were detected using specific antibodies, in the immunoprecipitates (left) and in the input cell extracts (right). Luc-luciferase FIG. 5 shows that UBXD7 recruits p97 to HIF1α. (A) p97-Myc was immunoprecipitated from HeLa cells treated or not with 20 μM MG132 for 2 h prior to harvesting the cells. Cells expressing no Myc-tagged protein were used as negative control. The indicated proteins were detected in the immunoprecipitates (top) and in the input cell extracts (bottom) using specific antibodies. (B) p97-Myc was immunoprecipitated from HeLa cells treated for 48 h with 5 nM of the indicated siRNAs and incubated with MG132 as above. The indicated proteins were detected using specific antibodies, in the immunoprecipitates (left) and in the input cell extracts (right). Luc—luciferase (C) HeLa cell extracts were fractionated on a Superdex 200 gel filtration column. Individual fractions were concentrated by TCA precipitation and subjected to western blotting using specific antibodies. All proteins were endogenously expressed.

FIG. 6 shows that p97 promotes HIF1α degradation. (A) Total cell extracts were prepared from cells treated with 5 nM of the indicated siRNA pools unless other siRNA concentration is specified. The siRNA treatment was 48 h and it was combined or not with 2 h of MG132 treatment. The indicated proteins were detected using specific antibodies. U7-UBXD7. (B) HIF1α mRNA was amplified by RT-PCR using specific primers. 18S rRNA was amplified as control. (C) Total cell extracts were prepared from cells treated with 5 nM of the indicated siRNA oligonucleotides or pools (p) for 48 h and incubated with 20 μM MG132 for 2 h. The indicated proteins were detected using specific antibodies. A non-specific band cross-reacting with the HIF1α antibodies is indicated with *. (D) UBXD7 Recruits p97/NPL4/UFD1 to the Ubiquitinated Substrate and Prevents Its Interaction with Other Proteasome Targeting Factors. Top: 1—UBA and UBX domains inactivate each other when the protein is not bound to the substrate. 2—Substrate oligo-ubiquitination or attachment of multiple monoubiquitin allows recruitment of several UBA-UBX molecules per substrate. UBA domains mask the emerging ubiquitin-chain and prevent substrate degradation. 3—Substrate binding frees the UBX domains that become available to recruit p97/NPL4/UFD1. The ubiquitin chain is elongated and the substrate is delivered to the proteasome for degradation. Bottom: In the absence of UBXD7, other proteasome targeting factors mediate accelerated substrate degradation. The Rpn10/PSMD4 subunit of the proteasome is depicted as an alternative ubiquitin receptor. S—substrate, E3-ubiquitin ligase FIG. 7 shows that UBXD7 shifts towards p97-positive fractions upon MG132 treatment. HeLa cell extracts were fractionated on a Superdex 200 gel filtration column. Individual fractions were concentrated by TCA precipitation and subjected to western blotting using specific antibodies. (A) Comparison between cells treated or not with MG132. (B) Comparison between cells treated with MG132 for 2 h, in which p97 was depleted by siRNA or not.

FIG. 8 shows that UBXD7 depletion is partially epistatic to p97 depletion with respect to accumulation of ubiquitinated HIF1α. The samples shown in FIG. 6A were boiled and re-analyzed by PAGE to better highlight that ubiquitinated HIF1α levels in cells depleted of both p97 and UBXD7 are intermediary between WT and p97-depleted cells.

DETAILED DESCRIPTION OF THE INVENTION

Overview

Figure 1A:
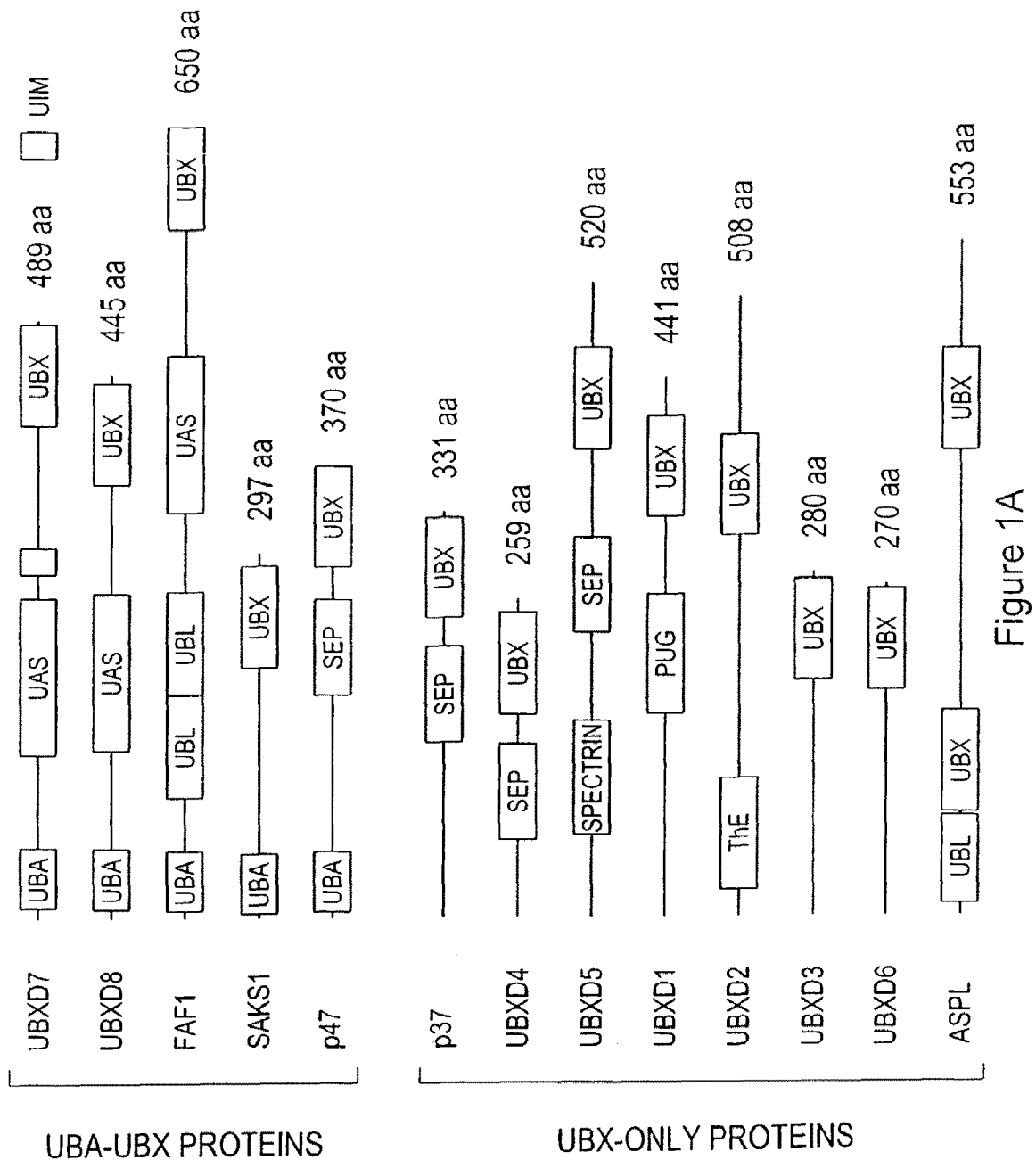
FIG. 1 shows that mammalian UBX-domain proteins interact with p97 and some serve as ubiquitin receptors. (A) The domain composition of human UBX proteins. Those identified in p97-Myc immunoprecipitates are indicated in red. UBA—Ubiquitin-associated; UIM—Ubiquitin-interacting motif; UBL—Ubiquitin-like; ThF—Thioredoxin-like fold. Further information about the respective domains can be found at http://www.ebi.ac.uk/interpro/. (B-D) N-terminally Flag-tagged UBX proteins were expressed in 293 cells and immunoprecipitated using anti-Flag beads. Cells expressing Flag-NPL4 or no Flag-tagged protein were used as positive and negative control, respectively. Some of the endogenous proteins that were coimmunoprecipitated are shown in western blots using specific antibodies. (Ubi)n refers to ubiquitin chains of varying length.

In certain aspects, the disclosure relates to the discovery of surprising associations between p97 and other proteins, including UBX-domain-containing proteins (UBX-polypeptides), HIF1α, and a variety of E3 ligases. p97 is a ATP-dependent chaperone that plays an important role in endoplasmic-reticulum associated degradation, but whose connection to degradation of soluble protein remain uncharacterized. As one of the most abundant proteins in the cell (Peters et al., 1990), p97 performs a variety of functions ranging from cell cycle regulation to membrane fusion and protein degradation (Ye, 2006). The most extensively studied p97 binding partners are p47 and the NPL4/UFD1 heterodimer, which form alternative complexes with p97 and direct its activity to different cellular processes. The NPL4/UFD1 adapter is needed for the function of p97 in UPS-dependent protein degradation, including the ERAD pathway, while p47 enables p97 to participate in homotypic membrane fusion. Many p97 functions, regardless of whether they are associated with proteolysis or not, involve recognition of ubiquitinated protein substrates. While p47 and NPL4/UFD1 are substrate-recruiting cofactors, p97 also interacts with a variety of substrate-processing cofactors like the E4 enzyme Ufd2 (Richly et al., 2005) or the deubiquitinating enzymes VCIP135 (Uchiyama et al., 2002; Wang et al., 2004) and Otu1 (Rumpf and Jentsch, 2006)

The disclosure provides unexpected insights into p97 biology that were elucidated using a focused, 'network proteomics' analysis (Graumann et al., 2004) of p97 and its UBX-polypeptide cofactors. Two major insights have emerged from this effort. First, it was discovered that UBA-UBX proteins associate with an unexpectedly broad range of ubiquitin ligases, including cullins 1 through 4, nine RING ligases, and three HECT domain enzymes. Given the great number of CRLs expressed in human cells and their intimate connection to a broad range of regulatory processes, these findings suggest that the substrate repertoire of p97 is far more diverse than previously appreciated and nominate p97 as a candidate regulator of numerous processes in which it has not previously been implicated. The second major finding, which flows directly from the first, is that this analysis has forged a direct and unexpected functional connection between p97 and HIF1α which is the key governor of cellular and host responses to oxygen tension.

The analysis of the p97 proteome has unearthed a trove of observations that challenge some current assumptions about p97. First, these findings indicate that ERAD is only a small fraction of p97's role in the UPS. Second, the interactions discussed herein challenge the notion that UBX proteins and NPL4/UFD1 form mutually exclusive complexes with p97. Other UBX-polypeptides including UBXD7, UBXD8, and FAF1 clearly form higher-order complexes that contain p97 and NPL4/UFD1. Third, the proteomic findings demonstrate that substrate-processing cofactors such as VCIP135, PLAP, and UFD2 are restricted to specific UBX-polypeptide/p97 complexes.

One of most significant discoveries in the disclosure relates to the finding that in cells treated with MG 132, UBXD7 coimmunoprecipitated all components of the CUL2/VHL ubiquitin ligase as well as its most prominent substrate, HIF1α. Although HIF1α metabolism has been the focus of intensive investigation, it has not been previously linked to p97 in any disclosure. Using UBXD7 as a prototype UBA-UBX protein and HIF1α as a model substrate, this disclosure describes new insights into the role of UBA-UBX adaptors within the p97 network. These insights may be used as a model for the interaction of other UBX and UBA-UBX proteins with their cognitive substrates.

The binding studies that linked HIF1α to UBXD7 and p97 were based in part on a series of siRNA knockdown experiments. In certain aspects of the disclosure, it is demonstrated that endogenous HIF1α accumulates in cells depleted of p97, while the opposite is seen when cells are depleted of UBXD7. To explain this apparent paradox, a model is proposed for a two-step function for UBXD7 in mediating HIF1α degradation via the p97 pathway. Binding of UBXD7 to ubiquitinated HIF1α commits it to the p97 pathway and shields it from other proteasome targeting factors. A protective role of UBXD7 that precedes its role in recruiting p97/NPL4/UFD1 would explain the observed discrepancy between the UBXD7 and p97 siRNA results. In cells depleted of p97, ubiquitinated HIF1α becomes trapped in non-productive complexes with UBXD7. However, in cells depleted of UBXD7, ubiquitinated HIF1α cannot be guided into the p97 pathway and is free to engage other targeting factors or the proteasome itself through its Rpn10/PSMD4 or Rpn13 subunits (FIG. 6D bottom). This would provide a more expeditious route for degradation than the pathway gated by UBXD7, hence the observed reduction in HIF1α levels.

HIF1α is the first known UBA-UBX protein ligand that is not associated with the ER. While elucidating the exact role played by UBXD7 in HIF1α degradation will require further studies, the p97 siRNA results clearly indicate a role for p97 in HIF1α degradation. Taken together, these results highlight the complexity of the substrate targeting and processing pathways that operate downstream of ubiquitin ligases and upstream of the proteasome and represents an attractive target for therapeutic modulation to treat a variety of associated diseases.

As indicated above, K11 linkages of ubiquitin were unexpectedly prominent in UBA-UBX immunoprecipitates. The UBA domains of RAD23 interact with a surface of ubiquitin that includes K48 (Ryu et al., 2003) and they inhibit assembly of K48-linked chains in vitro (Ortolan et al., 2000; Raasi and Pickart, 2003). If UBA-UBX proteins employed a similar binding mode, their UBA domains would be masking K48 of ubiquitin, thereby favoring modification of alternative lysine residues such as K11. The unexpected prominence of K11-linked chains reported here could explain why these linkages were estimated to be equi-abundant with K63-linked chains in budding yeast cells (Peng et al., 2003).

Moreover, K11-linked ubiquitin chains accumulate in neurodegenerative disorders associated with protein aggregation, like Alzheimer's (Cripps et al., 2006) or Huntington's disease (Bennett et al., 2007). Mutations in p97 are the underlying cause for the syndrome of inclusion body myopathy with Paget's disease of the bone and frontotemporal dementia—IBMPFD (Watts et al., 2004) and p97 colocalizes with protein aggregates in Huntington's, Machado-Joseph, and Parkinson's disease (Hirabayashi et al., 2001; Mizuno et al., 2003). K11 linkages can be generated by the ubiquitin ligase APC/C working in concert with the E2 enzymes Ubc4 and UbCH10 (Kirkpatrick et al., 2006). Very recently, Rape and colleagues reported that K11-linkages are required for the turnover of APC/C substrates (Jin et al., 2008). Taken together these observations suggest an unexpected connection between APC/C, p97, and human disorders rooted in defective protein homeostasis. As such, methods of the present invention relate to modulating the number of K11 linkages in a ubiquitin chain by modulating UBA-UBX complex formation. Therefore, methods and agents that modulate UBA-UBX complex formation can be used to treat disorders associated with accumulation of ubiquitinated proteins with increased K11-linkages.

In certain aspects, the disclosure relates to an association between certain disease states and the complex formations between UBX-polypeptides (UBXD8, UBXD4, UBXD7, UBXD6, ASPL, UBXD3, UBXD2, or UBXD1) and other proteins, including p97, UFD1, NPL4, a variety of E3 ligases (e.g., Cullin-RING Ligase or other RING-type E3 ligase, HECT E3 ligase, or U-box ligase), and complementary-binding substrates of a UBX-polypeptides (e.g., HIF1α). In preferred embodiments, the disclosure relates to a complex comprising at least UBXD7 and HIF1α. In certain aspects of the disclosure, by identifying a protein that associates with an UBX-polypeptide and/or p97 polypeptide, the present disclosure provides a conceptual link between the identified-binding substrates (e.g., HIF1α), the cellular processes and disorders associated with the identified-binding substrates, and the p97 and/or the UBX-polypeptide. Accordingly, in certain embodiments of the disclosure, test agents that modulate a complex of the disclosure thereby modulate the activity or stability of the interacting substrate. Thus, these test agents may now be used to modulate functions and disorders associated with the activity of the interacting substrate. In certain embodiments, test agents may be screened for an effect on the stability or activity of the complexes disclosed in this disclosure. Likewise, in certain embodiments of the disclosure, test agents identified to modulate complex stability and activity may now be used to modulate the activity of any interacting substrate (e.g., HIF1α) as a method for treating disorders and conditions associated with the function of the interacting substrate. Methods of identifying test agents that modulate the stability and/or activity a complex of the disclosure are described in detail herein.

In certain aspects, the disclosure provides method for treating hypoxia-related disorders or conditions by modulating the stability or activity of a disclosed protein complex. Hypoxia, a state of reduced oxygen, can occur when the lungs are compromised or blood flow is reduced. Ischemia, reduction in blood flow, can be caused by the obstruction of an artery or vein by a blood clot (thrombus) or by any foreign circulating matter (embolus), or by a vascular disorder such as atherosclerosis. Reduction in blood flow can have a sudden onset and short duration (acute ischemia), or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain, and heart, producing disorders such as intestinal infarction, pulmonary infarction, ischemic stroke, and myocardial infarction.

Currently, treatment of ischemic and hypoxic disorders is focused on relief of symptoms and treatment of causative disorders. For example, treatments for myocardial infarction include nitroglycerin and analgesics to control pain and relieve the workload of the heart. Other medications, including digoxin, diuretics, aminone, β-blockers, lipid-lowering agents and angiotensin-converting enzyme inhibitors, are used to stabilize the condition, but none of these therapies directly address the tissue damage produced by the ischemia and hypoxia Due to deficiencies in current treatments, there remains a need for methods that are effective in treating conditions involving ischemia and hypoxia such as occlusive arterial disease, angina pectoris, intestinal infarctions, pulmonary infarctions, cerebral ischemia, and myocardial infarction. There is also a need for methods that are effective in the prevention of tissue damage caused by ischemia that occurs due to, e.g., atherosclerosis, diabetes, and pulmonary disorders such as pulmonary embolism and the like. In certain embodiments, the disclosure provides methods that can be used to modulate HIFα activity and therefore treat, inhibit or reduce HIFα-associated disorders including conditions involving ischemia and hypoxia.

In some embodiments, an increase of HIF1α stability is desirable in situations in which HIF1α is abnormally low and/or in which increased HIF1α activity is likely to have a beneficial effect. For example, an increase of HIF1α stability is desirable in situations in which increased HIF1α activity is likely to have a beneficial effect (e.g., in cases for promoting angiogenesis). Likewise, decreasing HIF1α stability is desirable in situations in which HIF1α is abnormally high and/or in which decreased HIF1α activity is likely to have a beneficial effect (e.g., in the case of many forms of cancer).

Angiogenesis, defined as the growth of new capillaries from pre-existing vessels, is a pervasive biological phenomenon that is at the core of many physiologic and pathologic processes (U.S. Pat. No. 5,318,957, incorporated by reference herein in its entirety). Examples of physiologic processes which depend upon angiogenesis include embryogenesis, wound repair, repair of ischemic tissue damage and the ovarian/menstrual cycle (Folkman et al., Science 235:442 447 (1987)). In contrast, chronic inflammation associated with chronic fibroproliferative disorders as well as growth and metastasis of solid tumors are associated with aberrant angiogenesis, or an imbalance in the local micro-environmental ratio of the expression of angiogenic to angiostatic factors.

Given the primary role HIF1α plays in cellular responses to hypoxia and the presence of hypoxic regions in solid tumors, the mechanisms cells use to respond to hypoxia can be exploited as points of entry for therapeutic intervention. On a biochemical level, the changes tumor cells undergo under hypoxic conditions may be prevented by interfering with the cascade of gene expression that is regulated by HIF1α. What is needed, therefore, is an efficient way to prevent the accumulation of activated HIF1α in a cell, such that when the cell is exposed to hypoxia it is unable to adapt to low oxygen tension and thus undergoes apoptosis.

In certain aspects, the disclosure provides methods for treating E3-ligase-associated or ubiquitin proteasome-associated disorders by modulating the stability or activity of an indicated protein complex. Conjugation of ubiquitin to substrate proteins requires three enzymes: a ubiquitin-activating enzyme (E1), a ubiquitin-conjugating enzyme (E2), and a ubiquitin ligase (E3). Initially, E1 activates ubiquitin by forming a high-energy thioester intermediate with the C-terminal glycine using ATP. The activated ubiquitin is sequentially transferred to E2 and then to E3 which catalyzes isopeptide bond formation between the activated C-terminal glycine of ubiquitin and an epsilon-amino group of a lysine residue in the substrate. Ubiquitinated proteins are recognized by various cellular receptors and targeted to proteasomes for degradation. As used herein, the proteasome is a multisubunit complex found in both the nucleus and cytosol. The proteasome mediates the degradation of cytosolic, nuclear (Hershko and Ciechanover. 1998. Ann Rev Biochem 67:425), secretory and transmembrane proteins (Hirsch and Ploegh. 2000. Trends Cell Biol 10:268). In addition to clearing defective proteins the ubiquitin-proteasome system also carries out selective degradation of short-lived normal proteins thereby contributing to the regulation of numerous cellular processes. Under some circumstances, misfolded proteins may evade the ubiquitin-proteasome surveillance systems designed to promote correct folding and eliminate faulty proteins. When these misfolded proteins accumulate in sufficient quantity, they are prone to aggregation and may become resistant to proteolysis. As used herein, "aggregates", "inclusions", "bodies", "fibrils" and "plaques" are abnormal associations and accumulations of aberrant proteins that resist proteolysis and may or may not be associated with molecules of the proteasome system. In certain embodiments, modulating the stability or activity of a disclosed protein complex of the disclosure modulates the function or activity of an E3-ligase. As such, the increased or decreased activity of an E3-ligase may affect the turnover rate of various E3-ligase substrates. This method may be used to decrease the abnormal accumulation of various protein aggregates that occur in association with a given E3-ligase- or ubiquitin-associated disorder.

Definitions

The term "isolated", as used herein with reference to the subject proteins and protein complexes, refers to a preparation of protein or protein complex that is essentially free from contaminating proteins that normally would be present with the protein or complex (e.g., in the cellular milieu in which the protein or complex is found endogenously). Thus, an isolated protein complex is isolated from cellular components that normally would "contaminate" or interfere with the study of the complex in isolation, for instance while screening for modulators thereof. It is to be understood, however, that such an "isolated" complex may incorporate other proteins the modulation of which, by the subject protein or protein complex, is being investigated.

The term "isolated" as also used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

As used herein, the term "nucleic acid" refers to polynucleotide such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotide.

The terms "peptides", "proteins" and "polypeptides" are used interchangeably herein. The term "purified protein" refers to a preparation of a protein or proteins that are preferably isolated from, or otherwise substantially free of, other proteins normally associated with the protein(s) in a cell or cell lysate. The term "substantially free of other cellular proteins" (also referred to herein as "substantially free of other contaminating proteins") is defined as encompassing individual preparations of each of the component proteins comprising less than 20% (by dry weight) contaminating protein, and preferably comprises less than 5% contaminating protein. Functional forms of each of the component proteins can be prepared as purified preparations by using a cloned gene as described in the attached examples. By "purified", it is meant, when referring to component protein preparations used to generate a reconstituted protein mixture, that the indicated molecule is present in the substantial absence of other biological macromolecules, such as other proteins (particularly other proteins which may substantially mask, diminish, confuse or alter the characteristics of the component proteins either as purified preparations or in their function in the subject reconstituted mixture). The term "purified" as used herein preferably means at least 80% by dry weight, more preferably in the range of 85% by weight, more preferably 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

The term "similarity" refers to sequence similarity between two peptides or between two nucleic acid molecules. Similarity can be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as similar at that position. Expression as a percentage of homology/similarity or identity refers to a function of the number of identical or similar amino acids at positions shared by the compared sequences. A sequence which is "unrelated" or "non-homologous" shares less than 40% identity, though preferably less than 25% identity with a sequence of the disclosure. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the disclosure may be used as a "query sequence" to perform a search against public databases to, for example, identify other family members, related sequences or homologs. Such searches can be performed using the NBLAST and XBLAST programs (version 2.0) of Altschul, et al., (1990) J Mol. Biol. 215:403-10. BLAST nucleotide searches can be performed with the NBLAST program, score=100, wordlength=12 to obtain nucleotide sequences homologous to nucleic acid molecules of the disclosure. BLAST protein searches can be performed with the XBLAST program, score=50, wordlength=3 to obtain amino acid sequences homologous to protein molecules of the disclosure. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and BLAST) can be used. See http://www.ncbi.nlm.nih.gov.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

A "recombinant nucleic acid" is any nucleic acid that has been placed adjacent to another nucleic acid by recombinant DNA techniques. A "recombined nucleic acid" also includes any nucleic acid that has been placed next to a second nucleic acid by a laboratory genetic technique such as, for example, tranformation and integration, transposon hopping or viral insertion. In general, a recombined nucleic acid is not naturally located adjacent to the second nucleic acid.

The term "recombinant protein" refers to a protein of the present disclosure which is produced by recombinant DNA techniques, wherein generally DNA encoding the expressed protein is inserted into a suitable expression vector which is in turn used to transform a host cell to produce the heterologous protein. Moreover, the phrase "derived from", with respect to a recombinant gene encoding the recombinant protein is meant to include within the meaning of "recombinant protein" those proteins having an amino acid sequence of a native protein, or an amino acid sequence similar thereto which is generated by mutations including substitutions and deletions of a naturally occurring protein.

The term "binding" refers to a direct association between two molecules, due to, for example, covalent, electrostatic, hydrophobic, ionic and/or hydrogen-bond interactions under physiological conditions. Likewise, "complex formation," between two or more polypeptides, refers to a direct association between polypeptides, due to, for example, covalent, electrostatic, hydrophobic, ionic and/or hydrogen-bond interactions under physiological conditions.

A "chimeric protein" or "fusion protein" is a fusion of a first amino acid sequence encoding a polypeptide with a second amino acid sequence defining a domain foreign to and not substantially homologous with any domain of the first amino acid sequence. A chimeric protein may present a foreign domain which is found (albeit in a different protein) in an organism which also expresses the first protein, or it may be an "interspecies", "intergenic", etc. fusion of protein structures expressed by different kinds of organisms.

The terms "compound", "test compound", and "active agent" are used herein interchangeably and are meant to include, but are not limited to, polypeptides, nucleic acids, small molecules and antibodies. "Small molecule" as used herein, is meant to refer to a molecule that has a molecular weight of less than about 5 kD and most preferably less than about 2.5 kD, or even less than 1 kD. Small molecules can be nucleic acids, peptides, polypeptides, peptidomimetics, carbohydrates, lipids or other organic (carbon containing) or inorganic molecules (including, but not limited to, chemicals, metals, and organometallic compounds). Many pharmaceutical companies have extensive libraries of chemical and/or biological mixtures comprising arrays of small molecules, often fungal, bacterial, or algal extracts, which can be screened with any of the assays of the disclosure.

The phrase "conservative amino acid substitution" refers to grouping of amino acids on the basis of certain common properties. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include:
(i) a charged group, consisting of Glu and Asp, Lys, Arg and His,
(ii) a positively charged group, consisting of Lys, Arg and His,
(iii) a negatively charged group, consisting of Glu and Asp,
(iv) an aromatic group, consisting of Phe, Tyr and Trp,
(v) a nitrogen ring group, consisting of His and Trp,
(vi) a large aliphatic nonpolar group, consisting of Val, Leu and Ile,
(vii) a slightly polar group, consisting of Met and Cys,
(viii) a small-residue group, consisting of Ser, Thr, Asp, Asn, Gly, Ala, Glu, Gln and Pro,
(ix) an aliphatic group, consisting of Val, Leu, Ile, Met and Cys, and
(x) a small hydroxyl group, consisting of Ser and Thr.

In addition to the groups presented above, each amino acid residue may form its own group, and the group formed by an individual amino acid may be referred to simply by the one and/or three letter abbreviation for that amino acid commonly used in the art.

A "conserved residue" is an amino acid that is relatively invariant across a range of similar proteins. Often conserved residues will vary only by being replaced with a similar amino acid, as described above for "conservative amino acid substitution".

The term "domain" as used herein refers to a region of a protein that comprises a particular structure and/or performs a particular function (e.g., UBX domain, UBA domain, etc.).

The term "UBX domain" as used herein refers to an ~80-amino acid module that is found in a variety of p97 adaptor cofactors and it the putative binding motif for interacting with p97. The 'Ubiquitin regulatory X' (UBX) domain-containing proteins constitute one of the largest family of Cdc48/p97 cofactors. UBX proteins are involved in substrate recruitment to Cdc48/p97 and in the temporal and spatial regulation of its activity. In combination with UBX-like proteins and other cofactors, they can assemble into a large variety of Cdc48/p97-cofactor complexes possessing distinct cellular functions. The UBX (ubiquitin regulatory X) domain exhibits a α-grasp fold, with a β-β-α or β-β-α-β secondary structure organization, and the five α-strands are arranged in a mixed sheet (Yeung et al. Biochem Society Transactions, (2008) Vol. 36; Buchberger et al. J. Mol. Biol. (2001) Vol 307, 17-24; Dreveny et al. EMBO J. (2004) Vol. 23, 1030-1039). UBX-domain-containing proteins include UBXD7, UBXD8, FAF1, SAKS1, p47, p37, UBXD4, UBXD5, UBXD1, UBXD2, UBXD3, UBXD6, and ASPL.

The term "UBA domain" as used herein refers to an ~35 amino acid residue that is found in various proteins that function in ubiquitin-mediated proteolysis. The ubiquitin associated (UBA) domain binds to ubiquitin, multi-Ub chains, ubiquitinated proteins and other effectors, indicating a role for this motif in protein-protein interactions and subcellular targeting. UBA-domain-containing proteins include UBXD7, UBXD8, FAF1, SAKS1, and p47.

The term "UBX-domain-containing polypeptide" and "UBX-polypeptide" as used herein refers to polypeptides that contain an UBX domain. In preferred embodiments, UBX-polypeptides polypeptides of the present disclosure include UBXD8, UBXD7, UBXD4, ASPL, UBXD6, UBXD3, UBXD2, or UBXD1. In certain embodiments, a "UBX-polypeptide" does not include p47, FAF1, or SAKS1.

The term "RNA interference" or "RNAi" refers to any method by which expression of a gene or gene product is decreased by introducing into a target cell one or more double-stranded RNAs which are homologous to the gene of interest (particularly to the messenger RNA of the gene of interest). RNAi may also be achieved by introduction of a DNA:RNA hybrid wherein the antisense strand (relative to the target) is RNA. Either strand may include one or more modifications to the base or sugar-phosphate backbone. Any nucleic acid preparation designed to achieve an RNA interference effect is referred to herein as an "siRNA construct". Phosphorothioate is a particularly common modification to the backbone of an siRNA construct.

As used herein, the term "specifically hybridizes" or "hybridizes" refers to the ability of a nucleic acid probe/primer of the disclosure to hybridize to at least 12, 15, 20, 25, 30, 35, 40, 45, 50 or 100 consecutive nucleotides of a sequence of the disclosure, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the gene of the disclosure. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As used herein, the terms "treatment", "treating", and the like, refer to obtaining a desired pharmacologic and/or physiologic effect. The effect may be prophylactic in terms of completely or partially preventing a disorder or symptom thereof and/or may be therapeutic in terms of a partial or complete cure for a disorder (e.g., hypoxic-associated disease or HIF-1α-associated disorder) and/or adverse affect attributable to the disorder. "Treatment", as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein the terms "subject" and "patient" refer to animals including mammals including humans. The term "mammal" includes primates, domesticated animals including dogs, cats, sheep, cattle, goats, pigs, mice, rats, rabbits, guinea pigs, captive animals such as zoo animals, and wild animals. As used herein the term "tissue" refers to an organ or set of specialized cells such as skin tissue, lung tissue, kidney tissue, and other types of cells.

The term "therapeutic effect" is art-recognized and refers to a local or systemic effect in animals, particularly mammals, and more particularly humans caused by a pharmacologically active substance. The phrase "therapeutically effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

As used herein, the terms "gene" and "target gene" refer to a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "gene expression" or "expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell (for example, the interaction between HIF1α, and pVHL) can also affect gene expression as defined herein.

As used herein, the term "modulate" refers to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "down-regulate", and grammatical variants thereof are used interchangeably and refer to an activity whereby gene expression or a level of an RNA encoding one or more gene products is reduced below that observed in the absence of a nucleic acid molecule of the presently disclosed subject matter. In some embodiments, inhibition with an siRNA molecule results in a decrease in the steady state level of a target RNA. In some embodiments, inhibition with a siRNA molecule results in an expression level of a target gene that is below that level observed in the presence of an inactive or attenuated molecule that is unable to mediate an RNAi response. In some embodiments, inhibition of gene expression with an siRNA molecule of the presently disclosed subject matter is greater in the presence of the siRNA molecule than in its absence. In some embodiments, inhibition of gene expression is associated with an enhanced rate of degradation of the mRNA encoded by the gene (for example, by RNAi mediated by an siRNA). Furthermore, the terms "inhibit", "suppress", "down regulate", and grammatical variants thereof are used interchangeably and refer to an activity whereby gene expression or a level of an RNA encoding one or more gene products is reduced, resulting in the one or more polypeptide products encoded by said gene being reduced within a cell. As used herein, the terms "induce", "over-express", "up-regulate", and grammatical variants thereof are used interchangeably and refer to an activity whereby gene expression or a level of an RNA encoding one or more gene products is increased above that observed in the absence of a nucleic acid molecule of the presently disclosed subject matter. Furthermore, the terms "induce", "over-express", "up-regulate", and grammatical variants thereof are used interchangeably and refer to an activity whereby gene expression or a level of an RNA encoding one or more gene products is increased, resulting in the one or more polypeptide products encoded by said gene being increased within a cell.

As used herein, a "hypoxia-inducible gene" is a gene for which the expression level increases in response to hypoxia. In some embodiments, a hypoxia-inducible gene is a gene that is characterized by upregulated transcription in response to hypoxic conditions. Exemplary hypoxia-inducible genes thus include "HIF1α-regulated genes" that are characterized by hypoxia response elements (HREs) in their promoters. Under hypoxic conditions, transcription of these genes is induced as a result of activated HIF1 (HIF1α/HIF1β) binding to the HREs. Also as used herein, a HIF1α-regulated genes is a gene for which an activity of the gene product changes in response to hypoxia. In this embodiment, a hypoxia-inducible gene is a gene for which the polypeptide encoded by the gene experiences a change in state in response to hypoxia. Such a change in state includes, but is not limited to a post-transcriptional modification or an interaction with another molecule (for example, a protein-protein interaction).

The term "promoter" or "promoter region" each refers to a nucleotide sequence within a gene that is positioned 5' to a coding sequence of a same gene and functions to direct transcription of the coding sequence. The promoter region comprises a transcriptional start site, and can additionally include one or more transcriptional regulatory elements. In some embodiments, a method of the presently disclosed subject matter employs a hypoxia inducible promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner.

As used herein, "exogenous expression system" refers to a construct or combination of constructs that includes an inducible promoter and a nucleotide sequence of interest operable linked to the inducible promoter. In some embodiments, the construct may also contain a nucleotide sequence encoding a multi-chimeric transactivator, and the inducible promoter that can be transcriptionally activated by the multi-chimeric transactivator. For example, an exemplary inducible expression system of the invention could includes a nucleotide sequence encoding UBXD7 operably linked to a inducible promoter composed of a minimal promoter operably linked to at least one tetO sequence. By "transactivator," "transactivating factor," or "transcriptional activator" is meant a polypeptide that facilitates transcription from a promoter. Where the promoter is an inducible promoter, the transactivator activates transcription in response to a specific transcriptional signal or set of transcriptional signals. For example, an inducible expression system of the invention could include tTAER as a transactivator that facilitates transcription from the inducible tetO promoter when tTAER is not bound to tetracycline and is bound to estrogen. By "inducible promoter" is meant a promoter that is transcriptionally active when bound to a transcriptional activator, which in turn is activated under a specific set of conditions, e.g., in the presence of a particular combination of chemical signals that affect binding of the transcriptional activator to the inducible promoter and/or affect function of the transcriptional activator itself.

The term "expression vector", "vector", or "autonomously replicating expression vector" as used herein refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression. The vectors of the present invention can be autonomously self-replicating or allow for integration into the endogenous chromosome of the host cell.

The term "reporter gene" refers to any expressed transcript that can be measured for enhanced or diminished activity. Reporter genes are selected because the characteristics they confer on organisms expressing them are easily identified and measured. In the present disclosure, reporter gene fusions allow one of skill in the art to quantify the expression of fusion gene (e.g., a HIF1α-regulated gene fused to a reporter). Commonly used reporter genes that induce visually identifiable characteristics usually involve fluorescent proteins; examples include the gene that encodes jellyfish green fluorescent protein (GFP), which causes cells that express it to glow green under UV light, and the enzyme luciferase, which catalyzes a reaction with a luciferin to produce light. Another common reporter in bacteria is the lac Z gene, which encodes the protein beta-galactosidase. This enzyme causes bacteria expressing the gene to appear blue when grown on a medium that contains the substrate analog X-gal (an inducer molecule such as IPTG is also needed under the native promoter). Other fusion genes include selectable-markers. An example of a selectable-marker reporter in bacteria is the chloramphenicol acetyltransferase (CAT) gene, which confers resistance to the antibiotic chloramphenicol.

As used herein, an "exogenous" expressed gene includes any DNA sequence comprising one or more genes encoding a desired protein to be expressed and/or secreted in said cell. Such a DNA sequence may be a complementary DNA sequence (cDNA), an artificial DNA sequence, a genomic DNA sequence, a hybrid DNA sequence or a synthetic or semi-synthetic DNA sequence, included in an expression cassette enabling synthesis in the cells of said proteins. The expression cassette preferably comprises a transcription and translation initiation region joined to the 5' end of the sequence encoding said desired protein(s) so as to direct, and optionally regulate, the transcription and translation of said sequence. The choice of these regions may vary according to the fungal cell used. Generally, these sequences are chosen from promoters and/or terminators derived from host cell genes (either prokaryotic or eukaryotic in origin). These transcription and translation initiation regions may be further modified, e.g., by in vitro mutagenesis, by introduction of additional control elements or synthetic sequences, or by deletions. For example, transcription-regulating elements, such as the so-called UAS, originating from another promoter may be used to construct hybrid promoters which enable the growth phase of the cell culture to be separated from the phase of expression of the desired protein(s) encoding sequence(s). A transcription and translation termination region functional in the intended cell may also be positioned at the 3' end of the coding sequence. In addition, at the N-terminus of the protein sequence, a signal peptide (pre-sequence) may be introduced so as to direct the nascent protein to the secretory pathway of the fungal cell used. This pre-sequence may correspond to the natural pre-sequence of the protein if this protein is naturally secreted, or it may be of another origin, e.g., obtained from another gene, or even artificial.

Preferably, an "exogenous DNA sequence" is part of a vector, which may either replicate autonomously in the cell used or integrate into chromosome of the host cell. Autonomously replicating vectors may contain autonomously replicating sequences derived from the chromosomal DNA of the cell (ARS) or from naturally occurring cell plasmids. Integrating vectors usually contain sequences homologous to regions of the host cell chromosome, which, after being introduced into said cell, enable integration through in vivo recombination. The homologous sequences may correspond to the region of the chromosome to be modified in the cell, enabling a one-step modification-integration mechanism. Integration may also occur through non-homologous recombination.

The term "reaction mixture" refers to a solution that is prepared so as to favor polypeptide interaction and polypeptide-complex formation and/or activity. Generally, this will be physiological conditions, such as 50-200 mM salt (e.g., NaCl, KCl), pH of between 5 and 9, and preferably between 6 and 8. Such conditions may be optimized through trial and error. A variety of other reagents may be included in the compositions. These include reagents like salts, solvents, buffers, neutral proteins, e.g., albumin, detergents, etc. which may be used to facilitate optimal polypeptide interaction or reporter activity and/or reduce non-specific or background interactions. Also reagents that otherwise improve the efficiency of the assay, such as protease inhibitors, nuclease inhibitors, anti-microbial agents, etc., may be used. The compositions may also include adenosine tri-phosphate (ATP). The mixture of components may be added in any order that promotes polypeptide interaction or activity or optimizes identification of candidate modulator effects.

Drug Screening Assays

In certain aspects, the present disclosure provides assays to identify, optimize or otherwise assess active agents that either interfere with or promote function of a p97 polypeptide, a UBX-polypeptide, or an HIF1α polypeptide.

In certain aspects, the present disclosure provides assays to identify, optimize or otherwise assess active agents that either interfere with or promote complex formation between a UBX-polypeptide and a p97 polypeptide; optionally the complex may include at least one additional polypeptide selected from a NPL4 polypeptide, a UFD1 polypeptide, an E3-ligase, a subunit of an E3-ligase, or a binding substrate of an UBX-polypeptide (e.g., HIF1α).

In a preferred embodiment, the present disclosure provides assays to identify, optimize or otherwise assess active agents that either interfere with or promote complex formation between a UBXD7 polypeptide and a HIF1α polypeptide; optionally, the complex may include at least one additional polypeptide selected from a p97 polypeptide, a NPL4 polypeptide, a UFD1 polypeptide, and a CUL2 ubiquitin ligase or a subunit of a CUL2 ligase.

In certain aspects, the present disclosure further provides assays to identify, optimize or otherwise assess active agents that interfere with or promote expression of HIF1α-regulated genes.

Complexes of the disclosure may be generated in whole cells, taking advantage of cell culture techniques to support the subject assay. For example, the complex can be constituted in a eukaryotic cell culture system, including mammalian and yeast cells, or prokaryote cell cultures, including E. coli. Advantages to generating the subject assay in an intact cell include the ability to detect test agents, which modulate complex formation and/or activity, that are functional in an environment that more closely approximating one in which a therapeutic active agent would require, including the ability of the agent to gain entry into the cell.

The components of the complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

Agents to be tested can be produced, for example, by bacteria, yeast or other organisms (e.g., natural products), produced chemically (e.g., small molecules, including peptidomimetics), or produced recombinantly. In a preferred embodiment, the test agent is a small molecule, a polynucleotide, a polypeptide, an aptamer, or an antibody.

In certain embodiments, an assay comprises forming a reaction mixture of at least two selected polypeptides, as outlined above (e.g., a UBXD7 polypeptide and an HIF1α polypeptide), and a test agent. Additional components of the mixture may be selected to provide conditions that support protein-protein binding interactions between the selected polypeptides. One or more of a variety of parameters of the reaction mixture may be detected, such as test agent binding to the complex or selected polypeptide, complex stability, or complex or selected polypeptide activity (e.g., p97, UBXD7, or HIF1α polypeptide activity). The term "detect" is used herein to include a determination of the presence or absence of the subject of detection (e.g., complex stability, polypeptide stability, polypeptide or complex activity, etc.), a quantitative measure of the amount of the subject of detection, or a mathematical calculation of the presence, absence or amount of the subject of detection, based on the detection of other parameters. The term "detect" includes the situation wherein the subject of detection is determined to be absent or below the level of sensitivity. Detection may comprise detection of a label (e.g., fluorescent label, radioisotope label, and other described below), resolution and identification by size (e.g., SDS-PAGE, mass spectroscopy), purification and detection, and other methods that, in view of this specification, will be available to one of skill in the art. For instance, radioisotope labeling may be measured by scintillation counting, or by densitometry after exposure to a photographic emulsion, or by using a device such as a Phosphorimager. Likewise, densitometry may be used to measure a bound test agent or polypeptide to a complex following a reaction with an enzyme label substrate that produces an opaque product when an enzyme label is used.

Generally, a reaction mixture is prepared so as to favor polypeptide interaction and polypeptide-complex formation. Generally, this will be physiological conditions, such as 50-200 mM salt (e.g., NaCl, KCl), pH of between 5 and 9, and preferably between 6 and 8. Such conditions may be optimized through trial and error. Incubations may be performed at any temperature which facilitates optimal activity, typically between 4 and 40° C. Incubation periods are selected for optimum activity, but may also be optimized to facilitate rapid high through put screening. Typically, between 0.1 and 3 hours will be sufficient. A variety of other reagents may be included in the compositions. These include reagents like salts, solvents, buffers, neutral proteins, e.g., albumin, detergents, etc. which may be used to facilitate optimal polypeptide interaction or reporter activity and/or reduce non-specific or background interactions. Also reagents that otherwise improve the efficiency of the assay, such as protease inhibitors, nuclease inhibitors, anti-microbial agents, etc., may be used. The compositions may also include adenosine tri-phosphate (ATP). The components of the various assay mixtures provided herein may be combined in varying amounts. In some embodiments, the polypeptides of the present invention may be combined at a final concentration of from 0.1 ng to 10 mg per 100 µl reaction solution. Incubations are performed at any suitable temperature, typically between 4° C. and 40° C. Incubation periods are selected for optimum activity, but may also be optimized to facilitate rapid high-throughput screening.

In general, a test agent that modulates the interaction or activity of a protein complex or polypeptide of the invention-related activity may be used to modulate the function of the protein complex of polypeptide in vivo. A test agent that increases the interaction or activity of a protein complex or polypeptide of the invention-related activity may be used to stimulate these functions in vivo. Similarly, a test agent that inhibits the interaction or activity of a protein complex or polypeptide of the invention-related activity may be used to inhibit these functions in vivo. Test agent may be modified for use in vivo (e.g., by addition of a hydrophobic moiety, such as an ester).

An assay described herein may be used in a screening assay to identify agents that modulate any complex of the disclosure (e.g., UBXD7-HIF1α). A screening assay will generally involve adding a test agent to one of the reaction mixtures described herein, or any other assay designed to assess the stability or activity or a disclosed complex. The parameter(s) detected in a screening assay may be compared to a suitable reference. A suitable reference may be an assay run previously, in parallel or later that omits the test agent. A suitable reference may also be an average of previous measurements in the absence of the test agent.

In general the components of a screening assay mixture may be added in any order consistent with the overall activity to be assessed, but certain variations may be preferred. For example, in certain embodiments, it may be desirable to pre-incubate the test agent with one of the polypeptides (e.g., the UBXD7-polypeptide), followed by removing the test agent before the addition of other components or additional polypeptides to complete the assay (e.g., a HIF1α polypeptide). In this manner, the effects of the agent solely on one polypeptide may be assessed (e.g., the UBXD7).

In certain embodiments, the polypeptides of the assay are labeled, either directly or indirectly. This typically allows for easy and rapid detection and measurement of the polypeptides, making the assay useful for high-throughput screening applications. As descried above, certain embodiments may employ one or more tagged or labeled proteins. A "tag" is meant to include moieties that facilitate rapid isolation of the tagged polypeptide. A tag may be used to facilitate attachment of a polypeptide to a surface. A "label" is meant to include moieties that facilitate rapid detection of the labeled polypeptide. Certain moieties may be used both as a label and a tag (e.g., epitope tags that are readily purified and detected with a well-characterized antibody). Biotinylation of polypeptides is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known. Various labels include radioisotopes, fluorescers, chemiluminescers, enzymes, specific binding molecules, particles (e.g., magnetic particles) and the like. For the specific binding members, the complementary member would normally be labeled with a molecule that provides for detection, in accordance with known procedures.

Detection and quantification of complex stability provides a means for determining the test agents' efficacy at inhibiting or potentiating interaction between two or more polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Assaying complex stability or activity, in the presence and absence of a candidate test agent, can be accomplished in any vessel suitable for containing the reactants. Examples include microtitre plates, test tubes, and micro-centrifuge tubes.

In certain embodiments, an assay is performed in a high-throughput format. For example, one of the components of a reaction mixture may be affixed to a solid substrate and one or more of the other components is labeled. For example, the UBXD7 polypeptide may be affixed to a surface (e.g., a 96-well plate) while the labeled HIF1α is in solution. A test agent is added to the solution, and the formation of an UBXD7-HIF1α complex may be measured after washing the solid surface to remove uncomplexed HIF1α and detecting the HIF1α that remains bound (via the activity or presence of the label). Other variations may be used. For example, the complex formation may be assessed in the presence of at least one additional polypeptide selected from a p97 polypeptide, a NPL4 polypeptide, a UFD1 polypeptide, and a CUL2 ubiquitin ligase or a subunit of a CUL2 ligase. For multiple polypeptide interactions, more than one type or class of label may be used to detect the formation of a complex comprised of two or more polypeptides. In certain embodiments, the formation of complexes may be measured by an interactive technique, such as FRET, wherein a polypeptide (e.g., the UBXD7) is labeled with a first label and the desired complex partner (e.g., the HIF1α polypeptide) is labeled with a second label, wherein the first and second label interact when they come into close proximity to produce an altered signal. In FRET, the first and second labels are fluorophores. High-throughput screening may be achieved by performing an interactive assay, such as FRET or standard co-immunoprecipitation reactions, in solution as well, wherein the polypeptides or complex is freely diffusible in the solution (e.g., not bound to a solid surface). If a polypeptide in the mixture polypeptide, can be readily purified (e.g., with a specific antibody or via a tag such as biotin, FLAG, polyhistidine, etc.), the reaction may be performed in solution. The tagged polypeptide (e.g., UBXD7-His) can be rapidly isolated, along with any polypeptides (e.g., HIF1α) that are associated with the tagged polypeptide in the presence the test agent. Polypeptides present in the complex may also be resolved by SDS-PAGE for detection. Surface plasmon resonance systems, such as those available from Biacore International AB (Uppsala, Sweden), may also be used to detect protein-protein interaction In yet another embodiment, the interacting polypeptides of the complex can be used to generate an interaction trap assay for subsequently detecting agents which disrupt binding of the proteins to one another. (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In particular, the method makes use of chimeric genes which express hybrid proteins. To illustrate, a first hybrid gene comprises the coding sequence for a DNA-binding domain of a transcriptional activator can be fused in frame to the coding sequence for a UBXD7 polypeptide of sufficient length to bind to a potential interacting protein (e.g., HIF1α). The second hybrid protein encodes a transcriptional activation domain fused in frame to a gene encoding a HIF1α protein of sufficient length to interact with the UBXD7 polypeptide portion of the other fusion protein. If the UBXD7 polypeptide and HIF1α proteins are able to interact (e.g., form a complex), they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the UBXD7 and HIF1α polypeptides. Test agents can be added to this system to screen for active agents that decrease expression of the reporter gene, indicating that the test agent disrupts the interaction of the UBXD7-HIF1α polypeptide complex.

In certain embodiments, one or more polypeptides of the disclosure are bound to a bead, optionally with the assistance of a tag. Following ligation with the polypeptide, the beads may be separated from the unbound polypeptide(s) present in the reaction mixture, and the type or amount of bound polypeptide(s) can be measured. In certain embodiment, the beads with bound polypeptide(s) may be separated using a fluorescence-activated cell sorting (FACS) machine. Methods for such use are described in U.S. patent application Ser. No. 09/047,119, which is hereby incorporated in its entirety.

In a screening assay, the effect of a test agent may be assessed by, for example, assessing the effect of the test agent on kinetics, steady-state and/or endpoint of the reaction. In certain embodiments the reaction is complex formation. In certain embodiments, the reaction is a functional activity of at least one of the polypeptides present in the reaction mixture.

Certain embodiments of the disclosure relate to assays for identifying test agents that bind to an indicated complex (e.g., UBXD7-HIF1α). A wide variety of assays may be used for this purpose, including in vitro protein binding assays (e.g., saturation and competitive binding assays), electrophoretic mobility shift assays, immunoassays for protein binding, and the like.

A variety of assay formats are suitable for screening test agents and, in light of the present disclosure, those not expressly described herein will nevertheless be comprehended by one of ordinary skill in the art. Assay formats which approximate such conditions as formation of protein complexes, polypeptide activity, and even modulation HIF1α-regulated genes, may be generated in many different forms, and include assays based on cell-free systems (e.g., purified proteins or cell lysates), as well as cell-based assays which utilize intact cells. Simple binding assays can also be used to detect test agents which bind to polypeptides or protein complexes of the present invention. Such binding assays may also identify agents that act by disrupting the interaction between a polypeptide of a selected complex, or the binding of a complex to its complementary substrate.

In many drug screening programs which test libraries of compounds and natural extracts, high throughput assays are desirable in order to maximize the number of compounds surveyed in a given period of time. Assays of the disclosure that are performed in cell-free systems, such as may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assays instead being focused primarily on the effect of the drug on the molecular target as may be manifest in an alteration of binding affinity with other proteins or changes in enzymatic properties of the molecular target.

In preferred in vitro embodiments of the present assays, a reconstituted complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure complex assembly and/or disassembly.

In certain embodiments, a genetically modified cell is manipulated after incubation with a test agent and assayed for complex formation or polypeptide activity. In a specific embodiment, HIF1α activity is represented by the expression of a HIF1α-regulated gene. As demonstrated herein, an agent that disrupts UBXD7-HIF1α complex can cause a decrease in levels of HIF1α protein within a cell, and thereby decrease expression of a HIF1α-regulated gene. UBXS7-HIF1α complex formation in vivo may be assessed by immunoprecipitation techniques designed for determining in vivo cellular interactions. This technique can also be used to determine the in vivo stability of other complexes of the disclosure in the presence of a test agent. Fluorescence, Resonance Energy Transfer (FRET)-based assays or other energy transfer assays may also be used to determine complex formation within a cell.

In specific embodiment, the stability and/or activity of an UBXD7-HIF 1α complex may be determined in the presence of a test agent by measure the transcript levels of HIF1α-regulated genes. Transcript levels may be determined in any way known in the art, such as, for example, Northern blotting, RT-PCR, microarray, etc. Promoter regions for such HIF1α-regulated genes (or the minimal promoter region) may be operatively linked to a reporter gene and used in a reporter gene-based assay to detect test agents that enhance or diminish HIF1α-regulated gene expression.

In further embodiments, the disclosure provides methods for identifying targets for therapeutic intervention. A screen for test agent that modulates an UBXD7-HIF1α complex may be used to identify candidate therapeutics. Such active agents may be identified by screening for test agents that associated with an UBXD7-HIF1α complex by, for example, immunoprecipitation with an anti-UBXD7 or anti-HIF 1α antibody or an antibody that recognizes an UBXD7-HIF 1α complex, in silico analysis of high-throughput binding data, two-hybrid screens, and other protein-protein interaction assays described herein or otherwise known in the art in view of this disclosure. Agents that bind to such polypeptide targets or modulate polypeptide interactions thereof, or inhibit an activity of a polypeptide thereof may be used in such an assay. These include but are not limited to HIF1α and UBXD7 agonists and antagonist.

In certain embodiments, a test agent may be assessed for therapeutic activity by assessing effects on an HIF1α-regulation gene. The HIF-1α-regulated gene assessed maybe involved in a particular disorder (e.g., cancer, fibrosis, cardiovascular disease). Activity may be affected by a test agent that acts at one or more of the transcriptional, translational or post-translational stages. For example, an siRNA directed to a UBXD7 encoding gene will decrease activity, as will a small molecule that interferes with a binding activity of a UBXD7 polypeptide. In certain embodiments, the agent inhibits the activity of one or more polypeptides selected from: an UBXD7 polypeptide, a HIF1α polypeptide, a p97 polypeptide, a NPL4 polypeptide, a UFD1 polypeptide, and a CUL2/elongin BC/VHL ubiquitin ligase or a subunit of a CUL2/elongin/VHL ubiquitin ligase.

Exemplary Nucleic Acids and Expression Vectors

In certain aspects, the disclosure relates to nucleic acids encoding HIF1α, UBDX7, p97, NPL4, UFD1, CUL2, elongin B, elongin C, VHL, UBXD8, UBXD4, UBXD5, UBXD1, UBXD2, UBXD3, or UBXD6 polypeptides, such as, for example, SEQ ID NOs: 1, 3, 5, 7, 9, 11, 13, 15, 17, 19, 21, 23, 25, 27, and 29. Nucleic acids of the disclosure are further understood to include nucleic acids that comprise variants of SEQ ID NOs: 2, 4, 6, 8, 10, 12, 14, 16, 18, 20, 22, 24, 26, 28, and 30. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NOs: 2, 4, 6, 8, 10, 12, 14, 16, 18, 20, 22, 24, 26, 28, and 30, e.g., due to the degeneracy of the genetic code. In other embodiments, variants will also include sequences that will hybridize under highly stringent conditions to a nucleotide sequence of a coding sequence designated in any of SEQ ID NOs: 2, 4, 6, 8, 10, 12, 14, 16, 18, 20, 22, 24, 26, 28, and 30. Preferred nucleic acids of the disclosure are human HIF1α, UBDX7, p97, NPL4, UFD1, CUL2, elongin B, elongin C, VHL, UBXD8, UBXD4, UBXD5, UBXD1, UBXD2, UBXD3, or UBXD6 sequences, including, for example, SEQ ID NOs: 2, 4, 6, 8, 10, 12, 14, 16, 18, 20, 22, 24, 26, 28, and 30 and variants thereof and nucleic acids encoding an amino acid sequence selected from among SEQ ID NO: 1, 3, 5, 7, 9, 11, 13, 15, 17, 19, 21, 23, 25, 27, and 29.

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiment, the disclosure provides nucleic acids which hybridize under low stringency conditions of 6×SSC at room temperature followed by a wash at 2×SSC at room temperature.

Isolated nucleic acids which differ from the nucleic acid sequences of the disclosure due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of the disclosure.

Optionally, a nucleic acid of the disclosure will genetically complement a partial or complete loss of function phenotype in a cell. For example, a UBXD7 nucleic acid of the disclosure may be expressed in a cell in which endogenous UBXD7 has been reduced by RNAi, and the introduced UBXD7 nucleic acid will mitigate a phenotype resulting from the RNAi. In an exemplary embodiment, UBXD7 loss of function phenotype, as mediated by RNAi, results an observed decrease in levels of a HIF1α polypeptide.

Another aspect of the disclosure relates to nucleic acids that are used for antisense, RNAi or ribozymes. As used herein, nucleic acid construct can be administration to a cell for in situ generation of a nucleic acid or a derivative thereof which specifically hybridizes (e.g., binds) under cellular conditions with the cellular mRNA and/or genomic DNA encoding one of the HIF1α, p97, NPL4, UFD1, CUL2, elongin B, elongin C, VHL, UBX-polypeptides so as to inhibit production of that protein, e.g., by inhibiting transcription and/or translation. The binding may be by conventional base pair complementation, or, for example, in the case of binding to DNA duplexes, through specific interactions in the major groove of the double helix.

A nucleic acid construct of the disclosure can be delivered, for example, as an expression plasmid that, when transcribed in the cell, produces RNA, which is complementary to at least a unique portion of the cellular mRNA which encodes an indicated polypeptide. Alternatively, the construct is an oligonucleotide which is generated ex vivo and which, when introduced into the cell causes inhibition of expression by hybridizing with the mRNA and/or genomic sequences encoding a HIF1α, p97, NPL4, UFD1, CUL2, elongin B, elongin C, VHL, UBX-polypeptide. Such oligonucleotide probes are optionally modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in nucleic acid therapy have been reviewed, for example, by van der Krol et al., (1988) *Biotechniques* 6:958-976; and Stein et al., (1988) *Cancer Res* 48:2659-2668.

Accordingly, the modified oligomers of the disclosure are useful in therapeutic, diagnostic, and research contexts. In therapeutic applications, the oligomers are utilized in a manner appropriate for nucleic acid therapy in general.

The nucleic acid fragment used to transform the host cell may, optionally, include a Shine Dalgarno site (e.g., a ribosome binding site) and a start site (e.g., the codon ATG) to initiate translation of the transcribed message to produce the enzyme. It may, also optionally, include a termination sequence to end translation. A termination sequence is typically a codon for which there exists no corresponding aminoacetyl-tRNA, thus ending polypeptide synthesis. The nucleic acid fragment used to transform the host cell may optionally include a transcription termination sequence. The rrnB terminators, which is a stretch of DNA that contains two terminators, T1 and T2, is the most commonly used terminator that is incorporated into bacterial expression systems (J. Brosius et al., J. Mol. Biol., 148, 107-127 (1981)).

In another aspect of the disclosure, the subject nucleic acid is provided in an expression vector comprising a nucleotide sequence encoding a polypeptide of the disclosure operably linked to at least one regulatory sequence. Regulatory sequences are art-recognized and are selected to direct expression of any of the polypeptides of the disclosure. Accordingly, the term regulatory sequence includes promoters, enhancers and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding any of the polypeptide of the disclosure. Such useful expression control sequences, include, for example, the early and late promoters of SV40, tet promoter, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The nucleic acid fragment used to transform the host cell optionally may include one or more marker sequences. Generally speaking, suitable marker sequences typically encode a gene product, usually an enzyme that inactivates or otherwise detects or is detected by a compound in the growth medium. For example, the inclusion of a marker sequence may render the transformed cell resistant to an antibiotic, or it may confer compound-specific metabolism on the transformed cell. Examples of a suitable marker sequences that confer resistance include kanamycin, ampicillin, chloramphenicol and tetracycline. Alternatively, rather than selective pressure, a marker gene may be used that allows for detection of particular colonies containing the gene, such as beta-galactosidase, where a substrate is employed that provides for a colored product.

A variety of methods are suitable for transforming a cell of the present invention with an expression vector. Common transformation methods include electroporation, liposomal mediated transformation, calcium mediated transformation, and viral mediated transfection In certain aspects, when a host cell is transformed with the expression system of the present invention, the heterologous gene in said system can be integrated into the chromosomal DNA of the host cells by a so-called homologous recombination and the expression system will be carried stably in the host.

In order to integrate the expression system in the vector into chromosomal DNA of the host cells, an appropriate selection marker gene may be used wherein said marker gene has a sequence homologous to the gene on chromosomal DNA of the specific host cell. Selection markers for such a purpose can be easily selected by a skilled person. As an example, a preferred marker is a certain gene which exists on a chromosome and relates to the metabolism of the host cells. Namely, it is preferred to use a host which has been modified in such a manner that the above-mentioned gene on the chromosome will be inactivated by an appropriate means such as a mutation. The host can then be subjected to a homologous recombination with an expression vector containing the corresponding intact gene, whereupon only transformants which contain the normal metabolism gene can grow to be selected. Therefore, if such a marker gene has been introduced to the expression vector, a homologous recombination will take place between the marker gene in said expression vector and the corresponding portion of the chromosomal DNA, whereby the expression cassette of the heterologous gene will simultaneously be integrated into the chromosomal DNA.

As will be apparent, the subject gene constructs can be used to cause expression of polypeptides of the disclosure in cells propagated in culture, e.g., to produce proteins or polypeptides, including fusion proteins or polypeptides, for purification or to assay functional activity of the polypeptides.

This disclosure also pertains to a host cell transfected or transformed with a recombinant gene including a coding sequence for one or more polypeptides. The host cell may be any prokaryotic or eukaryotic cell. For example, a polypeptide of the disclosure may be expressed in bacterial cells such as *E. coli*, insect cells (e.g., using a baculovirus expression system), yeast, or mammalian cells. Other suitable host cells are known to those skilled in the art. Accordingly, the disclosure further pertains to methods of producing polypeptides. For example, a host cell transformed with an expression vector encoding a polypeptide of the disclosure can be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide. In a preferred embodiment, the polypeptide of the disclosure is a fusion protein containing a domain which facilitates its purification, such as a UBXD7-GST fusion protein, UBXD7-intein fusion protein, UBXD7-cellulose binding domain fusion protein, UBXD7-polyhistidine fusion protein, etc.

A preferred mammalian expression vectors may contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 3nd Ed., ed. by Sambrook, Fritsch and Maniatis (Cold Spring Harbor Laboratory Press, 2001), in particular Chapters 14-17. In some instances, it may be desirable to express the recombinant HIF1α, p97, NPL4, UFD1, CUL2, elongin B, elongin C, VHL, UBX-polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

Alternatively, the coding sequences for the polypeptide can be incorporated as a part of a fusion gene including a nucleotide sequence encoding a different polypeptide. In some embodiments, a fusion gene coding for a purification tag, such as a poly-(His)/enterokinase cleavage site sequence at the N-terminus of the desired portion of the recombinant protein, can allow purification of the expressed fusion protein by affinity chromatography using a $Ni^{2+}$ metal resin. The tagged sequence can then be subsequently removed by treatment with enterokinase to provide the purified HIF1α, p97, NPL4, UFD1, CUL2, elongin B, elongin C, VHL, UBX-polypeptide (see, e.g., Hochuli et al., (1987) J Chromatography 411:177; and Janknecht et al., *PNAS USA* 88:8972). Other common polypeptide purification tags useful in the current invention include, for example, streptavidin, biotin, glutathione-S-transferase (GST), maltose-binding domain, chitinase (e.g., chitin binding domain), cellulase (cellulose binding domain), thioredoxin, protein G, protein A, protein kinase inhibitor, or c-Myc.

In other embodiments, the fusion gene includes a nucleotide sequence encoding a reporter gene. Reporter genes are selected because the characteristics they confer on organisms expressing them are easily identified and measured. In the disclosure, reporter gene fusions allow one of skill in the art to quantify the expression of fusion gene (e.g., and HIF1α-regulated gene fused to a reporter). Commonly used reporter genes that induce visually identifiable characteristics usually involve fluorescent proteins; examples include the gene that encodes jellyfish green fluorescent protein (GFP), which causes cells that express it to glow green under UV light, and the enzyme luciferase, which catalyzes a reaction with a luciferin to produce light. Another common reporter in bacteria is the lac Z gene, which encodes the protein beta-galactosidase. This enzyme causes bacteria expressing the gene to appear blue when grown on a medium that contains the substrate analog X-gal (an inducer molecule such as IPTG is also needed under the native promoter). Other fusion genes include selectable-markers. An example of a selectable-marker reporter in bacteria is the chloramphenicol acetyl-transferase (CAT) gene, which confers resistance to the antibiotic chloramphenicol.

An amount of reporter gene can be assayed by any method for qualitatively or quantitatively determining presence or activity of the reporter gene product. The amount of reporter gene expression directed by each test promoter region fragment is compared to an amount of reporter gene expression to a control construct comprising the reporter gene in the absence of a promoter region fragment. A promoter region fragment is identified as having promoter activity when there is significant increase in an amount of reporter gene expression in a test construct as compared to a control construct. The term "significant increase", as used herein, refers to an quantified change in a measurable quality that is larger than the margin of error inherent in the measurement technique, in one example an increase by about 2-fold or greater relative to a control measurement, in another example an increase by about 5-fold or greater, and in yet another example an increase by about 10-fold or greater.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

Exemplary Polypeptides

In some embodiments, the disclosure relates to a HIF1α, UBDX7, p97, NPL4, UFD1, CUL2, elongin B, elongin C, VHL, UBXD8, UBXD4, UBXD5, UBXD1, UBXD2, UBXD3, or UBXD6 polypeptides, which are isolated from, or otherwise substantially free of, other intracellular proteins which might normally be associated with the protein or a particular complex including the protein. In other embodiments, the disclosure relates to a HIF1α, p97, NPL4, UFD1, CUL2, elongin BC, VHL, UBX-polypeptides, which are isolated from, or otherwise substantially free of, non-interacting intracellular proteins but may be isolated as a particular complex including one or more additional polypeptides. In certain embodiments, HIF1α, UBDX7, p97, NPL4, UFD1, CUL2, elongin B elongin C, VHL, UBXD8, UBXD4, UBXD5, UBXD1, UBXD2, UBXD3, or UBXD6 polypeptides have an amino acid sequence that is at least 60% identical to an amino acid sequence as set forth in any of SEQ ID Nos: 1, 3, 5, 7, 9, 11, 13, 15, 17, 19, 21, 23, 25, 27, and 29. In other embodiments, the polypeptide has an amino acid sequence at least 65%, 70%, 75%, 80%, 85%, 90%, 95%, 97%, 98%, 99% or 100% identical to an amino acid sequence as set forth in any of SEQ ID Nos: 1, 3, 5, 7, 9, 11, 13, 15, 17, 19, 21, 23, 25, 27, and 29.

Optionally, recombinant polypeptide of the disclosure will function in place of an endogenous polypeptide, for example by mitigating a partial or complete loss of function phenotype in a cell. For example, a UBXD7 polypeptide of the disclosure may be produced in a cell in which endogenous UBXD7 has been reduced by RNAi, and the introduced UBXD7 polypeptide will mitigate a phenotype resulting from the RNAi. In certain embodiments, a UBXD7 polypeptide, when produced at an effective level in a cell, promotes HIF1α stability and/or promotes expression of HIF1α-regulated genes.

In another aspect, the disclosure provides polypeptides that are agonists or antagonists of a HIF1α, p97, or UBX-polypeptide. Variants and fragments of these polypeptides may have a hyperactive or constitutive activity, or, alternatively, act to prevent a HIF1α, p97, or UBX-polypeptide from performing one or more functions. For example, a truncated form lacking one or more domain may have a dominant negative effect. In some embodiment, an agonist of a UBX-polypeptide is a truncated form of the same UBX-polypeptide that contains an active UBX-domain.

Another aspect of the disclosure relates to polypeptides derived from a full-length polypeptide of the disclosure. Isolated peptidyl portions of the subject proteins can be obtained by screening polypeptides recombinantly produced from the corresponding fragment of the nucleic acid encoding such polypeptides. In addition, fragments can be chemically synthesized using techniques known in the art such as conventional Merrifield solid phase f-Moc or t-Boc chemistry. For example, any one of the subject proteins can be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of the formation of a specific protein complex, or more generally of a complex comprising two or more polypeptides of the disclosure, such as by microinjection assays.

It is also possible to modify the structure of the polypeptides of the disclosure for such purposes as enhancing therapeutic or prophylactic efficacy, or stability (e.g., ex vivo shelf life and resistance to proteolytic degradation in vivo). Such modified polypeptides, when designed to retain at least one activity of the naturally occurring form of the protein, are considered functional equivalents of the polypeptides. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Conservative replacements are those that take place within a family of amino acids that are related in their side chains. Genetically encoded amino acids can be divided into four families (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a HIF 1α, p97, NPL4, UFD1, CUL2, elongin B, elongin C, VHL, UBX-polypeptide can be assessed, e.g., for their ability to bind to another polypeptide or assessed for a functional activity, e.g., modulation of the expression of a HIF1α-regulated gene. Polypeptides in which more than one replacement has taken place can readily be tested in the same manner.

Mutagenesis can give rise to homologs which have intracellular half-lives dramatically different than the corresponding wild-type protein. For example, the altered protein can be rendered either more stable or less stable to proteolytic degradation or other cellular process which result in destruction of, or otherwise inactivation of the polypeptide of interest. Such homologs, and the genes which encode them, can be utilized to alter polypeptide levels by modulating the half-life of the protein. For instance, a short half-life can give rise to more transient biological effects and, when part of an inducible expression system, can allow tighter control of recombinant polypeptide levels within the cell. In some embodiments, such proteins, and particularly their recombinant nucleic acid constructs, can be used in gene therapy protocols.

Treatment Methods

In certain aspects, the disclosure provides methods for treatment or prevention of hypoxia-associated diseases or conditions in a patient or a cell. Hypoxia-associated diseases that are amenable to treatment or prevention by the methods of the disclosure include disorders or conditions that are influenced by activity or expression level of HIF1, as well as by the expression of a HIF1α-regulated gene(s).

The regulation of HIF1-mediated transcription occurs via post-translational modifications of HIF1α that depend upon the oxygen status of the cell. In oxygenated (normoxic) cells, HIF1α subunits are hydroxylated by the enzyme prolyl-hydroxylase using molecular oxygen as the oxygen donor. This hydroxylation allows von Hippel-Lindau tumor suppressor (pVHL) and an E3 ubiquitin ligase component, which is normally present within the cell, to bind to HIF1α, forming a pVHL/HIF1α complex. The HIF1α is subject to ubiquitination and degradation by cellular proteasomes. Under hypoxic conditions, prolyl-hydroxylase activity is much lower due to the relative absence of the oxygen donor. Under these conditions, HIF1α is not hydroxylated, pVHL/HIF1α complexes do not form, and the steady state level of HIF1α within the cell increases. HIF1α is thus available to form active HIF1 by complexing with HIF1α, which results in accumulation of an active HIF1α/HIF1β complex in the nucleus. Within the nucleus, an active HIF1 complex binds to sequences called hypoxia responsive elements (HREs) that are present in the promoters of certain hypoxia responsive genes. The binding of HIF1 to an HRE-containing promoter results in up-regulated transcription of the associated gene. HIF1 binding results in increased expression of several genes, including transcription factors, growth factors, and cytokines, as well as genes involved in oxygen transport and iron metabolism, glycolysis and glucose uptake, and stress-response (Jiang et al. (1996) J Biol Chem 271:17771-17778; Iliopoulus et al. (1996) Proc Natl Acad Sci USA 93:10595-10599; Maxwell et al. (1999) Nature 399:271-275; Sutter et al. (2000) Proc Natl Acad Sci USA 97:4748-4753; Cockman et al. (2000) J Biol Chem 275:25733-25741; and Tanimoto et al. (2000) EMBO J. 19:4298-4309).

Levels of HIF1α protein are elevated in most cells in response to hypoxia, and HIF1α is induced in vivo when animals are subjected to anemia or hypoxia. HIF1α levels rise within a few hours after the onset of hypoxia and return to baseline under continued hypoxic conditions. HIF1α has been implicated in numerous cellular and developmental processes including cell proliferation, angiogenesis, and cell cycle arrest. HIF1α has also been associated with myocardial acute ischemia and early infarction, pulmonary hypertension, and inflammation. Hypoxic preconditioning, in which a target organ is subjected to brief periods of hypoxia, has been shown to protect both myocardium and brain against hypoxic-ischemic injury. HIF1α stabilization is closely associated with ischemia and is induced by preconditioning. (Wang and Semenza (1993) Proc Natl Acad Sci USA 90:4304-4308; Stroka et al. (2001) FASEB J 15:2445-2453; Semenza et al. (1997) Kidney Int 51:553-555; Carmeliet et al. (1998) Nature 394:485-490; Zhong et al. (1999) Cancer Res 59:5830-5835; Lee et al. (2000) N Engl J Med 343:148-149; Sharp et al. (2000) J Cereb Blood Flow Metab 20:1011-1032; Semenza et al. (2000) Adv Exp Med Biol 475:123-130; Thornton et al. (2000) Biochem J 350:307-312; Deindl and Schaper (1998) Mol Cell Biochem 186:43-51; Bergeron et al. (2000) Ann Neurol 48:285-296.)

In addition, hypoxia regulates cellular proliferation and migration related to angiogenesis. The vascular endothelial growth factor (VEGF) gene, the product of which is a critical regulatory factor in angiogenesis, contains an HRE in its promoter. HIF1 up-regulates the expression of VEGF and FLT-1, a VEGF receptor. Due to the high growth rate of the cells that make up a solid tumor, new blood vessels are constantly needed to provide rapidly growing tumor cells with adequate nutrients, including oxygen. These newly formed blood vessels frequently are characterized by abnormalities, such that it is very common to find areas of tumors in which individual cells fail to be oxygenated sufficiently. In fact, published data suggest that there are localized regions of hypoxia in virtually every tumor larger than 1 mm (Dachs & Tozer, 2000).

In the view of the teachings herein, one of skill in the art will understand that the methods of the disclosure are applicable to a wide range disorders associated with HIF1α regulation, including, for example, cell proliferation, apoptosis, glucose metabolism, pH regulation, erythopoiesis, iron metabolism, extracellular matrix metabolism, inflammation, angiogenesis and control of vascular tone. As such, the disclosure provides methods for treating or preventing hypoxia-associated diseases including, but not limited to, cancer, cardiovascular disease, heart disease, stroke, macular degeneration, diabetic retinopathy, arthritis, inflammation, sepsis, sepsis-induced shock, renal disease, tissue fibrosis, gastrointestinal disease, neurodegenerative disease, respiratory distress syndrome, bronchopulmonary displasia, pulmonary hypertension, hypoxic pulmonary hypertension, severe pulmonary hypertension, COPD, diabetic retinopathy, diabetes, corneal neovascularization, pathogenic blood vessel growth, musculoskeletal disorder, ischemic-reperfusion injury, myocardial hypoxia, or cardiac hypertrophy. In addition to treatment with an active agent that modulates the stability or activity of any of the HIF1α complexes of the disclosure, a patient or cell may be optionally treated with an additional active agent known in the art to modulate HIF1α stability or activity. In certain embodiments, the additional active agents may include active agents that modulate the activity of a HIF1α-prolyl-hydroxylase or a HIF-asparaginyl-hydroxylase. In certain embodiments, the additional active agent may be selected from iron chelators such as desferrioxamine (DFO), divalent metal salts such as $CoCl_2$, angiotensin II, thrombin, and platelet-derived growth factor.

In certain embodiment, the disclosure provides methods for treating or preventing cancer diseases. The terms "cancer", "tumor", and "neoplasia" are all used interchangeably herein. As used herein, a cancer is characterized by one or more of the following properties: cell growth that is not regulated by the normal biochemical and physical influences in the environment; anaplasia (e.g., lack of normal coordinated cell differentiation); and in some instances, metastasis. Cancer disease treatable by the methods herein include, for example, bladder cancer, breast cancer, colorectal cancer, endometrial cancer, head and neck cancer, lung cancer, leukemia, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, ependymoma, Ewing's sarcoma family of tumors, germ cell tumor, extracranial cancer, Hodgkin's disease, acute lymphoblastic leukemia, acute myelod leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, esophageal cancer, hairy cell leukemia, kidney cancer, multiple myeloma, oral cancer, pancreatic cancer, primary central nervous system lymphoma, or skin cancer.

In addition to treatment with an active agent that modulates the stability or activity of any one of the complexes of the disclosure, a patient or cell may be optionally treated with an additional anti-cancer therapeutic. Anti-cancer therapeutics are well known by one of skill in the art and include, for example, chemotherapy, radioimmunocojugation, other forms of radiopharmaceutical therapy, external beam therapy, surgery, and other anti-malignancy treatments. In certain aspects, the additional active agent is an anti-angiogen, including, for example, antagonists of EGF, VEGF, matrix metalloproteinase proteins, vascular targeting agents, and inegrins. Specific anti-angiogens known in the art include bevaizumab, angiostatin, endostatin, 2-methoxyestradiol, gefitinib, and thalidomide.

Treatment methods of the disclosure may be used to increases sensitivity of a cancer or tumor, delay the growth of a cancer or tumor, inhibit blood vessel growth within or in association with a cancer or a tumor, inhibit metastasis of a cancer or a tumor. In certain embodiments, the disclosure provides methods for the modulation of a HIF1α-regulated gene(s) (e.g., SNAI1, TCF3, ZEB1, or E-Cadherin) that prevents cancer cell or tumor cell detachment. In certain embodiments, the modulation of a HIF1α-regulated gene (e.g., c-Met, LOX, RhoA, CAIX, AMF, MMP2, TIMP-1/2, uPAR, or Cathepsin D) prevents tumor cell invasion. In certain embodiments, modulation of a HIF1α-regulated gene (e.g., VEGF, VEGF1/2, ANGPT1, ANGPT2, ANGPT4, PGF, or PDGF8) prevents cancer or tumor cell angiogenesis. In certain embodiments, modulation of a HIF1α-regulated gene (e.g., CXCR4 or SDF1) prevents cancer or tumor seeding.

In certain embodiments, the disclosure provides, in part, methods for treating renal diseases in a patient. Renal diseases treatable by the methods herein include, for example, renal ischemia, renal infarction, contrast nephropathy, hypoxic damage of isolated perfused kidneys, renal fibrosis, and cyst formation. In certain aspects, the disclosure provides methods for the modulation of a HIF1α-regulated gene(s) (e.g., metalloproteinases-1, plasminogen-activator-inhibitor-1, connective tissue growth factor, or TGFβ) to treat, inhibit, or prevent renal fibrosis. In addition to treatment with an active agent that modulates the stability or activity of any one of the complexes disclosed by the disclosure, a patient or cell may be optionally treated with an additional active agent used to treat renal disease.

In certain embodiments, the disclosure provides, in part, methods for treating neurodegenerative diseases in a patient. Neurodegenerative diseases treatable by the method herein include, for example, Parkinson's disease, Alzheimer's disease, multiple sclerosis, Friedreich's Ataxia, or other neurodegenerative disorders that result from a disruption of iron homeostasis. In certain aspects, the disclosure provides methods for the modulation of a HIF1α-regulated gene(s) (e.g., TfR or HO-1) to treat, inhibit, or prevent neurodegenerative disease in a patient. In addition to treatment with an active agent that modulates the stability or activity of any one of the complexes of the disclosure, a patient or cell may be optionally treated with an additional active agent used to treat a neurodegenerative disease. In some embodiments, the additional active agent is a pharmacological iron chelator (e.g., DFO or CG). In some embodiments, the additional active agent is ferritin.

In certain aspects, the disclosure provides methods for treatment of a ubiquitin proteasome-associated disease or condition in a patient or a cell. Ubiquitin proteasome-associated disease that are amenable to treatment by the methods of the disclosure include serpinopathies, hemolytic anemia, Huntington's Disease, cystic fibrosis, amyotrophic lateral sclerosis, and Parkinson disease, amyloid-related diseases, Alzheimer's disease, transmissible spongiform encephalopathies, Diabetes Type II, dialysis-related amyloidosis, secondary amyloidosis, cerebral amyloid angiopathy, inclusion body myositis, Down's syndrome and Age-Related Macular Degeneration, spinobulbar muscular atrophy or Kennedy's disease, spinocerebellar ataxia type 1; spinocerebellar ataxia type 2, Machado-Joseph disease, spinocerebellar ataxia type 6, spinocerebellar ataxia type 7, spinocerebellar ataxia type 17, dentatorubral-pallidolu-sian atrophy, dystrophia myotonica, Pick's Disease, corticobasal degeneration, progressive supranuclear palsy, amyotrophic lateral sclerosis/parkinsonism dementia complex, Friedreich's ataxia, fragile XE mental retardation, fragile X syndrome, Wilson's Disease, chronic liver diseases, and cataracts.

In certain aspects, the disclosure provides methods for treatment of an E3-ligase-associated disorder disease or condition in a patient or a cell. Ubiquitin proteasome-associated disease that are amenable to treatment by the methods of the disclosure include Angelman disease, Juvenile recessive Parkinson, the APECED form of autoimmune polyendocrinopathy syndrome, con Hippel-Lindau syndrome, cogentical polycytemia, Fanconi anemia, or breast or ovarian cancer.

Test Agents and Therapeutic Active Agents

In some embodiments, the disclosure provides active agents, which modify the stability or activity of an indicated complex, that are useful in the treatment of various disorders. In certain embodiments, the active agents may be characterized as agonists or antagonist of complex formation. In the present disclosure, agonists encompass all compounds and compositions that increase or otherwise promote stability or activity of an indicated complex. In contrast, antagonists encompass all compounds and compositions that decrease, block, or inhibit complex formation or activity. In some embodiments, agonists and antagonist include small molecules, polypeptides (including antibodies), or nucleic acids (including antisense nucleic acids, aptamers, ribozymes, and small interfering RNAs or siRNAs). Antagonists encompass any composition that modulates, affects, alters, inhibits or reduces the activity of any of the complexes described herein by at least 5, 10, 20, 30, 40, 50, 60, 70, 80, 90, 95, 97, 98, 99 or 100%. In specific embodiments, the agonist or antagonist effect is determined by measuring the stability or activity of the substrate of an UBX-polypeptide (e.g., HIF1α).

In certain embodiments, one or more of the UBX-polypeptide and/or p97 antagonists is an antisense nucleic acid that targets the expression of the target polypeptide. By "antisense nucleic acid," it is meant a non-enzymatic nucleic acid compound that binds to a target nucleic acid by means of RNA-RNA, RNA-DNA or RNA-PNA (protein nucleic acid) interactions and alters the activity of the target nucleic acid (for a review, see Stein and Cheng, 1993 Science 261, 1004 and Woolf et al., U.S. Pat. No. 5,849,902). Typically, antisense molecules are complementary to a target sequence along a single contiguous sequence of the antisense molecule. However, in certain embodiments, an antisense molecule can form a loop and binds to a substrate nucleic acid which forms a loop. Thus, an antisense molecule can be complementary to two (or more) non-contiguous substrate sequences, or two (or more) non-contiguous sequence portions of an antisense molecule can be complementary to a target sequence, or both. For a review of current antisense strategies, see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

In other embodiments, the UBX and/or p97 antagonist may be an siRNA. The term "short interfering RNA," "siRNA," or "short interfering nucleic acid," refers to any nucleic acid compound capable of mediating RNAi or gene silencing when processed appropriately by a cell. For example, the siRNA can be a double-stranded polynucleotide molecule comprising self-complementary sense and antisense regions, wherein the antisense region comprises complementarity to a target nucleic acid compound (e.g., UBX or p97). The siRNA can be a single-stranded hairpin polynucleotide having self-complementary sense and antisense regions, wherein the antisense region comprises complementarity to a target nucleic acid compound. The siRNA can be a circular single-stranded polynucleotide having two or more loop structures and a stem comprising self-complementary sense and antisense regions, wherein the antisense region comprises complementarity to a target nucleic acid compound, and wherein the circular polynucleotide can be processed either in vivo or in vitro to generate an active siRNA capable of mediating RNAi. The siRNA can also comprise a single stranded polynucleotide having complementarity to a target nucleic acid compound, wherein the single-stranded polynucleotide can further comprise a terminal phosphate group, such as a 5'-phosphate (see for example Martinez et al., 2002, Cell., 110, 563-574), or 5',3'-diphosphate.

As described herein, the subject siRNAs are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer. In certain embodiments, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides. The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Production of the subject siRNAs can be carried out by chemical synthetic methods or by recombinant nucleic acid techniques. Endogenous RNA polymerase of the treated cell may mediate transcription in vivo, or cloned RNA polymerase can be used for transcription in vitro. As used herein, siRNA molecules of the disclosure need not be limited to those molecules containing only RNA, but further encompasses chemically-modified nucleotides and non-nucleotides. For example, the dsRNAs may include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The dsRNAs may be produced enzymatically or by partial/total organic synthesis, any modified ribonucleotide can be introduced by in vitro enzymatic or organic synthesis. Methods of chemically modifying RNA molecules can be adapted for modifying dsRNAs (see, e.g., Heidenreich et al. (1997) Nucleic Acids Res, 25:776-780; Wilson et al. (1994) J Mol Recog 7:89-98; Chen et al. (1995) Nucleic Acids Res 23:2661-2668; Hirschbein et al. (1997) Antisense Nucleic Acid Drug Dev 7:55-61). Merely to illustrate, the backbone of a dsRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the disclosure lack 2'-hydroxy (2'-OH) containing nucleotides.

In a specific embodiment, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In certain embodiments, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythyinidine is tolerated and does not affect the efficiency of RNAi. The absence of a 2' hydroxyl significantly enhances the nuclease resistance of the overhang in tissue culture medium and may be beneficial in vivo.

In another specific embodiment, the subject dsRNA can also be in the form of a long double-stranded RNA. For example, the dsRNA is at least 25, 50, 100, 200, 300 or 400 bases. In some cases, the dsRNA is 400-800 bases in length. Optionally, the dsRNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In a further specific embodiment, the dsRNA is in the form of a hairpin structure (named as hairpin RNA or short hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In certain embodiments, antisense oligonucleotides comprise modification with Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($-CH_2-$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638.)

The synthesis and preparation of the LNA monomers adenine, cytosine, guanine, 5-methylcytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

In certain embodiments, an siRNA molecule of the invention comprises one or more (e.g., about 1, 2, 3, 4, 5, 6, 7, 8, 9, 10, or more) locked nucleic acid (LNA) nucleotides, for example, at the 5'-end, the 3'-end, both of the 5' and 3'-ends, or any combination thereof, of the siRNA molecule PCT application WO 01/77350 describes an exemplary vector for bi-directional transcription of a transgene to yield both sense and antisense RNA transcripts of the same transgene in a eukaryotic cell. Accordingly, in certain embodiments, the present disclosure provides a recombinant vector having the following unique characteristics: it comprises a viral replicon having two overlapping transcription units arranged in an opposing orientation and flanking a transgene for a dsRNA of interest, wherein the two overlapping transcription units yield both sense and antisense RNA transcripts from the same transgene fragment in a host cell.

In another embodiment, one or more UBX-polypeptide and/or p97 antagonists may be an enzymatic nucleic acid. By "enzymatic nucleic acid," it is meant a nucleic acid which has complementarity in a substrate binding region to a specified target gene, and also has an enzymatic activity which is active to specifically cleave a target nucleic acid. It is understood that the enzymatic nucleic acid is able to intermolecularly cleave a nucleic acid and thereby inactivate a target nucleic acid. These complementary regions allow sufficient hybridization of the enzymatic nucleic acid to the target nucleic acid and thus permit cleavage. One hundred percent complementarity (identity) is preferred, but complementarity as low as 50-75% can also be useful (see for example Werner and Uhlenbeck, 1995, Nucleic Acids Research, 23, 2092-2096; Hammann et al., 1999, Antisense and Nucleic Acid Drug Dev., 9, 25-31). The enzymatic nucleic acids can be modified at the base, sugar, and/or phosphate groups. As described herein, the term "enzymatic nucleic acid" is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acids with enzymatic activity. The specific enzymatic nucleic acids described herein are not meant to be limiting and those skilled in the art will recognize that all that is important in an enzymatic nucleic acid is that it has a specific substrate binding site which is complementary to one or more of the target nucleic acid regions, and that it have nucleotide sequences within or surrounding that substrate binding site which imparts a nucleic acid cleaving and/or ligation activity to the molecule (Cech et al., U.S. Pat. No. 4,987,071; Cech et al., 1988, 260 JAMA 3030). In certain embodiments, an enzymatic nucleic acid is a ribozyme designed to catalytically cleave an mRNA transcripts to prevent translation of mRNA (see, e.g., PCT International Publication WO90/11364, published Oct. 4, 1990; Sarver et al., 1990, Science 247:1222-1225; and U.S. Pat. No. 5,093,246). In another embodiment, an enzymatic nucleic acid is a DNA enzyme. Methods of making and administering DNA enzymes can be found, for example, in U.S. Pat. No. 6,110,462.

In certain embodiments, one or more of the UBX-polypeptide and/or p97 antagonists are scaffold-based binding proteins such as Nanobody, Evibody, Ankyrin repeat protein, Transbody, Anticalin, Microbody, AdNectin, Domain antibody, Affibody, Maxibody, Tetranectin, Affilin molecule, iMabs, and Monobody (Hey et al., Trends Biotechnol, 2005, 23: 514-522; Binz et al., Nat Biotechnol, 2005, 23: 1257-1268; Hosse, R. J., et al., Protein Science, 15:14-27 (2006)). In certain embodiments, the protein display scaffold is a fibronectin based "addressable" therapeutic binding molecule. The fibronectin domain III (FnIII) loops comprise regions that may be subjected to random mutation and directed evolutionary schemes of iterative rounds of target binding, selection, and further mutation in order to develop useful therapeutic tools. Exemplary fibronectin based protein therapeutics are Adnectins™ as described in PCT publications WO00/34784, WO01/64942, and WO02/032925.

In some embodiments, one or more of the UBX-polypeptide and/or p97 antagonists comprises an antibody or antigen binding fragment that binds to UBX-polypeptide or p97 or to UBX-polypeptide or p97 ligand protein. It is understood that antibodies may be Fab, Fv, scFv, Fab' and F(ab')$_2$, monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques.

In some embodiments, the antibody fragments provided are truncated chains (truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments This disclosure also provides fragments of anti-UBX-polypeptide or anti-p97 antibodies, which may comprise a portion of an intact antibody, such as for example, the antigen-binding or variable region of the intact antibody. Examples of antibody fragments include Fab, Fab', F(ab')$_2$, and Fv fragments; diabodies; linear antibodies (Zapata et al., Protein Eng. 1995; 8(10): 1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" usually refers to the minimum antibody fragment that contains a complete antigen-recognition and -binding site. This region consists of a dimer of one heavy- and one light-chain variable region in tight, non-covalent association. It is in this configuration that the three CDRs of each variable region interact to define an antigen-binding site on the surface of the $V_H$-$V_L$ dimer. Collectively, the CDRs confer antigen-binding specificity to the antibody. However, even a single variable region (or half of an Fv comprising three CDRs specific for an antigen) has the ability to recognize and bind antigen, although likely at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

SMIPs are a class of single-chain peptides engineered to include a target binding region and effector domain (CH2 and CH3 domains). See, e.g., U.S. Patent Application Publication No. 20050238646. The target binding region may be derived from the variable region or CDRs of an antibody, e.g., an anti-EphB4 antibody of the disclosure. Alternatively, the target binding region is derived from a protein that binds EphB4.

The term "diabodies" refers to small antibody fragments with two antigen-binding sites, which fragments comprise a heavy-chain variable region ($V_H$) connected to a light-chain variable region ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (Janeway et al., *Immunobiology* 5th edition, page 147, Garland Publishing (New York, 2001)).

The anti-UBX-polypeptide and/or anti-p97 antibodies of the disclosure include antibodies having all types of constant regions, including IgM, IgG, IgD, IgA and IgE, and any isotype, including IgG1, IgG2a, IgG2b, IgG3 and IgG4. The light chains of the antibodies can either be kappa light chains or lambda light chains.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al.

In some embodiments, the p97 and/or UBX-polypeptide agonist is an aptamer. Aptamers, are oligonucleotides, which can be synthetic or natural, that bind to a particular target molecule, such as a protein or metabolite. Typically, the binding is through interactions other than classic Watson-Crick base pairing. Aptamers represent a promising class of therapeutic agents currently in pre-clinical and clinical development. Like biologics, e.g., peptides or monoclonal antibodies, aptamers are capable of binding specifically to molecular targets and, through binding, inhibiting target function. A typical aptamer is 10-15 kDa in size (i.e., 30-45 nucleotides), binds its target with sub-nanomolar affinity, and discriminates among closely related targets (e.g., will typically not bind other proteins from the same gene family) (Griffin, et al. (1993), Gene 137(1): 25-31; Jenison, et al. (1998), Antisense Nucleic Acid Drug Dev. 8(4): 265-79; Bell, et al. (1999), In Vitro Cell. Dev. Biol. Anim. 35(9): 533-42; Watson, et al. (2000), Antisense Nucleic Acid Drug Dev. 10(2): 63-75; Daniels, et al. (2002), Anal. Biochem. 305(2): 214-26; Chen, et al. (2003), Proc. Natl. Acad. Sci. U.S.A. 100(16): 9226-31; Khati, et al. (2003), J. Virol. 77(23): 12692-8; Vaish, et al. (2003), Biochemistry 42(29): 8842-51).

Aptamers can be created by an entirely in vitro selection process (Systematic Evaluation of Ligands by Experimental Enrichment, i.e., SELEX™) from libraries of random sequence oligonucleotides as described in U.S. Pat. Nos. 5,475,096 and 5,270,163. Aptamers have been generated against numerous proteins of therapeutic interest, including growth factors, enzymes, immunoglobulins, and receptors (Ellington and Szostak (1990), Nature 346(6287): 818-22; Tuerk and Gold (1990), Science 249(4968): 505-510).

Aptamers have a number of attractive characteristics for use as therapeutics. In addition to high target affinity and specificity, aptamers have shown little or no toxicity or immunogenicity in standard assays (Wlotzka, et al. (2002), Proc. Natl. Acad. Sci. U.S.A. 99(13): 8898-902). Indeed, several therapeutic aptamers have been optimized and advanced through varying stages of pre-clinical development, including pharmacokinetic analysis, characterization of biological efficacy in cellular and animal disease models, and preliminary safety pharmacology assessment (Reyderman and Stavchansky (1998), Pharmaceutical Research 15(6): 904-10; Tucker et al., (1999), J. Chromatography B. 732: 203-212; Watson, et al. (2000), Antisense Nucleic Acid Drug Dev. 10(2): 63-75).

A suitable method for generating an aptamer to a target of interest is with the process entitled "Systematic Evolution of Ligands by EXponential Enrichment" ("SELEX™"). The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX™ method applied to the application of high affinity binding involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule. Systematic Evolution of Ligands by Exponential Enrichment, "SELEX™," is a method for making a nucleic acid ligand for any desired target, as described, e.g., in U.S. Pat. Nos. 5,475,096 and 5,270,163, and PCT/US91/04078, each of which is specifically incorporated herein by reference.

Pharmaceutical Preparations and Formulations

In certain embodiments, the methods described herein involve administration of an therapeutic-effective amount of an active agent to a subject to treat, inhibit or reduce a HIF1α-associated disorder or condition, a hypoxia-associated disorder or condition, a ubiquitin proteasome-associated disorder or condition, or an E3-ligase-associated disorder or condition in a patient. The therapeutic agents may be formulated in a conventional manner using one or more physiologically acceptable carriers or excipients. For example, therapeutic agents and their physiologically acceptable salts and solvates may be formulated for administration by, for example, injection (e.g., SubQ, IM, IP), inhalation or insufflation (either through the mouth or the nose) or oral, buccal, sublingual, transdermal, nasal, parenteral or rectal administration. In certain embodiments, therapeutic agents may be administered locally, at the site where the target cells are present, such as in a specific tissue, organ, or fluid (e.g., blood, cerebrospinal fluid, tumor mass, etc.).

Therapeutic agents can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), therapeutic agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

Therapeutic agents may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulator agents such as suspending, stabilizing and/or dispersing agents. Alternatively, the active ingredient may be in powder form for constitution with a suitable vehicle, e.g., sterile pyrogen-free water, before use.

In addition, therapeutic agents may also be formulated as a depot preparation. Such long acting formulations may be administered by implantation (for example subcutaneously or intramuscularly) or by intramuscular injection. Thus, for example, therapeutic agents may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

In certain embodiments, therapeutic agents are incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parade's, waxes, and the like.

Pharmaceutical compositions (including cosmetic preparations) may comprise from about 0.00001 to 100% such as from 0.001 to 10% or from 0.1% to 5% by weight of one or more Therapeutic agents described herein. In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of therapeutic agents, or by insertion of a sustained release device that releases therapeutic agents. Therapeutic agents may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds may be injected directly into the vitreous and aqueous humour. In a further alternative, the compounds may be administered systemically, such as by intravenous infusion or injection, for treatment of the eye.

Therapeutic agents described herein may be stored in oxygen free environment according to methods in the art.

In certain embodiments, therapeutic agents of the invention include nucleic acid compounds. Methods for delivering nucleic acid compounds are known in the art (see, e.g., Akhtar et al., 1992, Trends Cell Bio., 2, 139; and Delivery Strategies for Antisense Oligonucleotide Therapeutics, ed. Akhtar, 1995; Sullivan et al., PCT Publication No. WO 94/02595). These protocols can be utilized for the delivery of virtually any nucleic acid compound. Nucleic acid compounds can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to, oral (tablet or pill form) and/or intrathecal delivery (Gold, 1997, Neuroscience, 76, 1153-1158). Other approaches include the use of various transport and carrier systems, for example though the use of conjugates and biodegradable polymers. For a comprehensive review on drug delivery strategies, see Ho et al., 1999, Curr. Opin. Mol. Ther., 1, 336-343 and Jain, Drug Delivery Systems: Technologies and Commercial Opportunities, Decision Resources, 1998 and Groothuis et al., 1997, J. NeuroVirol., 3, 387-400. More detailed descriptions of nucleic acid delivery and administration are provided in Sullivan et al., supra, Draper et al., PCT WO93/23569, Beigelman et al., PCT Publication No. WO99/05094, and Klimuk et al., PCT Publication No. WO99/04819.

Antisense nucleotides, such as siRNA, may be delivered to cancer cells using a variety of methods. Cell-penetrating peptides (CPPs) having the ability to convey linked "cargo" molecules into the cytosol may be used (see Juliano, Ann N Y Acad. Sci. 2006 October; 1082:18-26). In certain embodiments, an atelocollagen-mediated oligonucleotide delivery system is used (Hanai et la. Ann N Y Acad. Sci. 2006 October; 1082:9-17). An LPD formulation (liposome-polycation-DNA complex) may be used to deliver siRNA to tumor cells. (Li et al. Ann N Y Acad. Sci. 2006 October; 1082:1-8). Complexation of siRNAs with the polyethylenimine (PEI) may also be sued to deliver siRNA into cells (Aigner, J Biomed Biotechnol. 2006; 2006(4):71659). siRNA may also be complexed with chitosan-coated polyisohexylcyanoacrylate (PIHCA) nanoparticles for in vivo delivery (see, e.g., Pille et al., Hum Gene Ther. 2006 October; 17(10):1019-26).

EXEMPLIFICATION

The disclosure now being generally described, it will be more readily understood by reference to the following examples, which are included merely for purposes of illustration of certain aspects and embodiments of the present disclosure, and are not intended to limit the disclosure.

The following antibodies are used in these examples: anti-Flag, anti-ubiquitin (Sigma), anti-p97 (Research Diagnostics), anti-NPL4 (Abnova), anti-UFD1, anti-CUL3 (BD Transduction Laboratories), anti-PLAP (Epitomics), anti-CUL1, anti-CUL2 (Zymed), anti-VHL (Santa Cruz Biotechnology), anti-UBR1 (courtesy of A. Varshavsky lab), anti-HIF1α (Novus), anti-UBXD7 (courtesy of Millipore), anti-UBXD8 (Imgenex), and anti-CA IX (courtesy of J. Pastorek and S. Pastorekova). MG132 was purchased from Biomol. The truncation mutants were obtained by site directed mutagenesis. STOP codons were placed at the corresponding position in the wild-type plasmid such that the Flag-UBXD7ΔUBX construct expresses UBXD7(1-400), Flag-UBA expresses UBXD7(1-62), and Flag-p47ΔUBX expresses p47(1-232). See Table 1 for the list of wild-type plasmids used in these examples.

TABLE 1

Plasmids Used in Examples

| RDB Number | Plasmid Name | Vector | ORF Source | Nucleotide Accession No. |
|---|---|---|---|---|
| 2155 | Flag-UBXD7 | pCMV5B | Kazusa DNA Research Institute | A B018337 |
| 2143 | Flag-UBXD8 | pCMV5B | Open Biosystems | BC014001 |
| 2151 | Flag-FAF1 | pLPC | Invitrogen | BC004970 |
| 2150 | Flag-SAKS1 | pLPC | Invitrogen | BC000902 |
| 2148 | Flag-p47 | pCMV5B | G. Warren lab | AB002086 |
| 2152 | Flag-UBXD1 | pLPC | GeneCopoeia | NM_025241 |
| 2153 | Flag-UBXD2 | pLPC | GeneCopoeia | BC035594 |
| 2149 | Flag-UBXD3 | pLPC | Invitrogen | BC036417 |
| 2146 | Flag-UBXD5 | pCMV2 | H. Katoh lab | BC078730 |
| 2145 | Flag-UBXD6 | pCMV2 | Open Biosystems | BC020694 |
| 2144 | Flag-ASPL | pCMV2 | Open Biosystems | BC018722 |
| 2154 | Flag-NPL4 | pCMV2 | G. Warren lab | BC101887 |
| 2147 | p97-Myc | pCMV5B | G. Warren lab | BC049114 |

Example 1

Mammalian p97 Interacts with Multiple UBX Domain-Containing Cofactors

Applicants analyzed p97-Myc immunoprecipitates from human 293 cells by MudPIT (Multidimensional Protein Identification Technology) (Link et al., 1999), searching for new p97 cofactors.

For immunoprecipitation experiments, the cells were lysed in buffer A (50 mM HEPES/KOH, pH 7.5; 5 mM Mg(OAc)$_2$; 70 mM KOAc; 0.2% Triton X-100; 10% glycerol; 0.2 mM EDTA; protease inhibitors) and incubated with anti-Flag agarose beads (Sigma) or anti-Myc sepharose beads (Covance).

Mass spectrometrical sample analysis was performed as described previously (Graumann et al., 2004) using a high-pressure liquid chromatography pump (Agilent) in line to a LCQ DecaXP electrospray ion trap mass spectrometer (ThermoFinnigan). In brief, 2-4 mg of protein extract were incubated with anti-Flag or anti-Myc beads and the immunoprecipitated proteins were eluted with saturated urea. The eluates were then proteolytically digested using sequentially endoproteinase Lys-C and trypsin. The resulting peptide mixtures were pressure-loaded onto triphasic microcapillary columns and sample separation was achieved using a chromatography program consisting of six salt steps, each followed by an organic gradient. The eluting peptides were electrosprayed into the mass spectrometer and the column eluate was continuously analyzed. One full-range mass scan (400-1400 nm/z) was followed by three data-dependent tandem mass spectrometry (MS/MS) spectra. Sequence database matching was performed against the IPI human database (Kersey et al., 2004) version 3.15.1 using Sequest (Eng et al., 1994) and the results were filtered with DTASelect (Tabb et al., 2002), using the parameters indicated in Graumann et al. (2004). This analysis revealed eight p97 binding partners (Table 2), all containing a UBX (structurally similar to ubiquitin) domain in their C-terminal region (FIG. 1A).

Figure 1B:
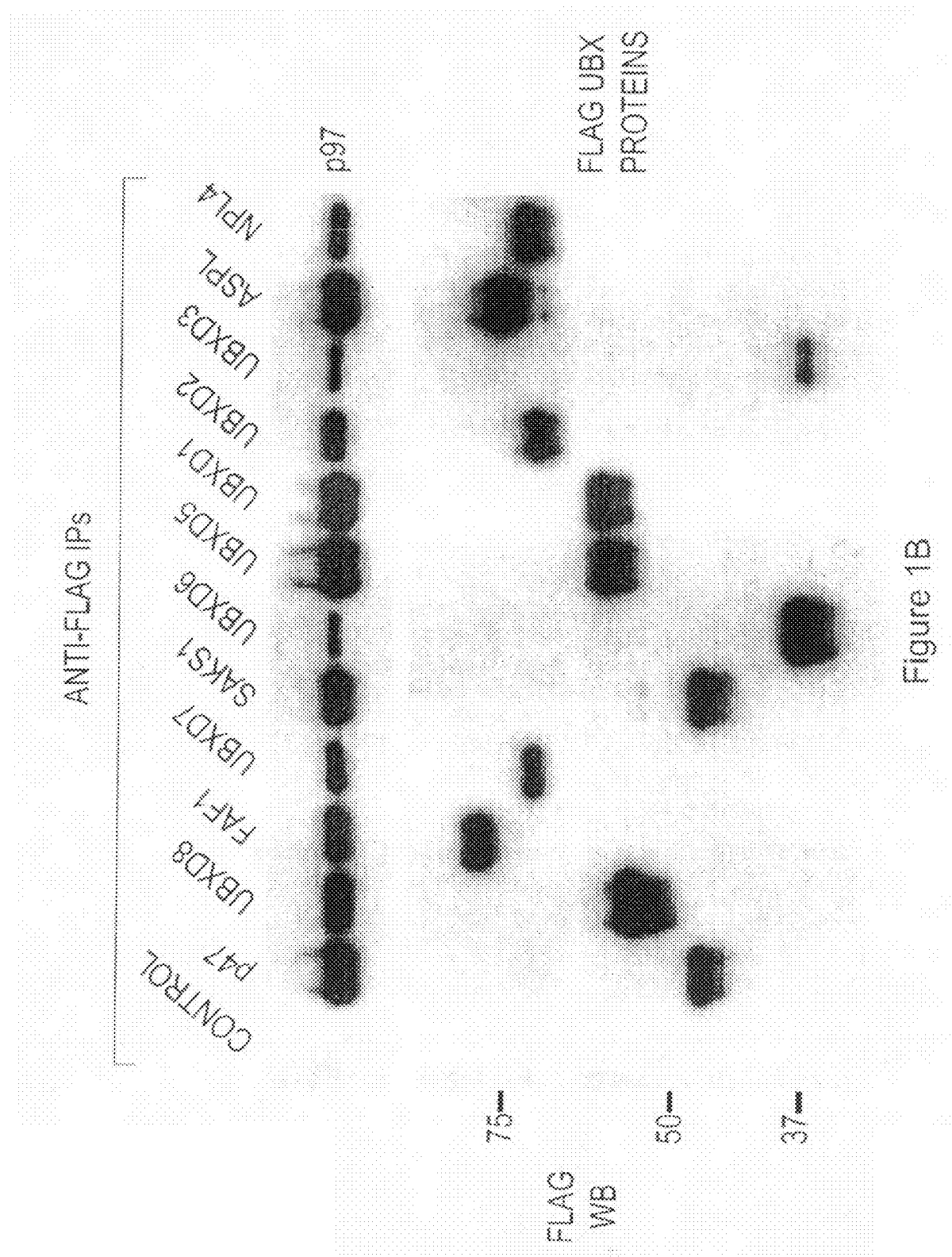

The human proteome includes at least thirteen different UBX proteins (FIG. 1A), some of which were not identified in the initial analysis. At least three of those, UBXD1 (Carim-Todd et al., 2001), Socius/UBXD5 (Katoh et al., 2002), and Rep-8/UBXD6 (Yamabe et al., 1997), are mainly expressed in the reproductive organs and might be expressed poorly in the 293 kidney cell line used for immunoprecipitation. Upon expressing their Flag-tagged versions in 293 cells, it was confirmed that eleven mammalian UBX domain-containing proteins (five of which were absent in the original p97 immunoprecipitates) coimmunoprecipitated endogenous p97 (FIG. 1B; Table 3) together the mass spectrometry and immunoprecipitation/Western analyses confirmed that all thirteen mammalian UBX proteins bound p97. Given that UBX proteins invariably bind p97/Cdc48, UBX emerges as a signature domain for p97 binding partners across species.

TABLE 2

UBX-Domain Proteins Identified by Mass Spectrometry in p97-Myc Immunoprecipitates

| Protein Name | MW (Da) | Sequence count | Spectrum count | Sequence coverage |
|---|---|---|---|---|
| p47 | 40573 | 19 | 153 | 52.2% |
| UBXD8 | 52624 | 11 | 12 | 33.7% |
| p37 | 37077 | 6 | 7 | 32.3% |
| UBXD7 | 54862 | 8 | 12 | 29.0% |
| SAKS1 | 33325 | 2 | 2 | 19.5% |
| UBXD4 | 29278 | 4 | 5 | 19.3% |
| ASPL | 60183 | 7 | 13 | 17.2% |
| FAF1 | 73954 | 7 | 11 | 8.2% |

The number of unique peptides identified (sequence count) is indicated, as is the total number of peptides (spectrum count), which takes into account that some peptides were identified multiple times.

TABLE 3

Known p97 Cofactors Identified by Mass Spectrometry in Flag-UBX Protein Immunoprecipitates

| Protein Name | NPL4 69461[a] | UFD1 38725a | PLAP 87099[a] | VCIP135 134320[a] | p97 | Flag Protein |
|---|---|---|---|---|---|---|
| p47 | 2(2) 6.0% | | 27(38) 42.9% | 14(15) 17.6% | 172(1611) 82.7% | 30(164) 47.6% |
| UBXD8 | 11(209) 20.6% | 7(82) 29.4% | 10(15) 20.1% | 11(12) 14.1% | 48(3090) 57.6% | 23(664) 44.3% |
| FAF1 | 22(46) 36.3% | 13(15) 35.3% | 2(2) 4.8% | 5(5) 5.9% | 84(539) 68.9% | 30(205) 34.2% |
| UBXD7 | 14(33) 24.5% | 4(4) 12.5% | 2(2) 4.0% | | 77(375) 61.2% | 38(224) 51.3% |
| SAKS1 | 7(30) 20.1% | | 26(90) 32.1% | 2(2) 2.9% | 68(663) 57.4% | 7(26) 32.0% |
| UBXD6 | 9(16) 16.5% | 4(5) 19.2% | | 2(2) 2.7% | 55(212) 59.5% | 17(94) 47.0% |
| UBXD5 | 2(3) 5.2% | | 6(6) 11.6% | 20(25) 27.5% | 124(783) 75.5% | 5(16) 9.4% |
| UBXD1 | | | 3(3) 7.5% | 2(2) 2.5% | 159(1134) 84.3% | 45(119) 66.9% |
| UBXD2 | | | | | 27(958) 41.1% | 11(36) 34.3% |
| UBXD3 | 7(9) 14.1% | 3(3) 12.2% | | | 57(254) 64.5% | 17(33) 48.9% |
| ASPL | | | 10(10) 22.8% | | 154(1445) 78.5% | 114 (661) 78.8% |
| NPL4 | 49(387) 51.2% | 14(22) 37.9% | | 2(2) 2.5% | 79(414) 70.4% | 49(387) 51.2% |

[a]Molecular weight of the respective protein in Da.
The sequence count, the spectrum count (in parenthesis), and the corresponding percentage of sequence coverage are indicated for each interacting protein. The results obtained for p97 and the UBX protein itself are shown as a reference.

Example 2

Figure 1C:
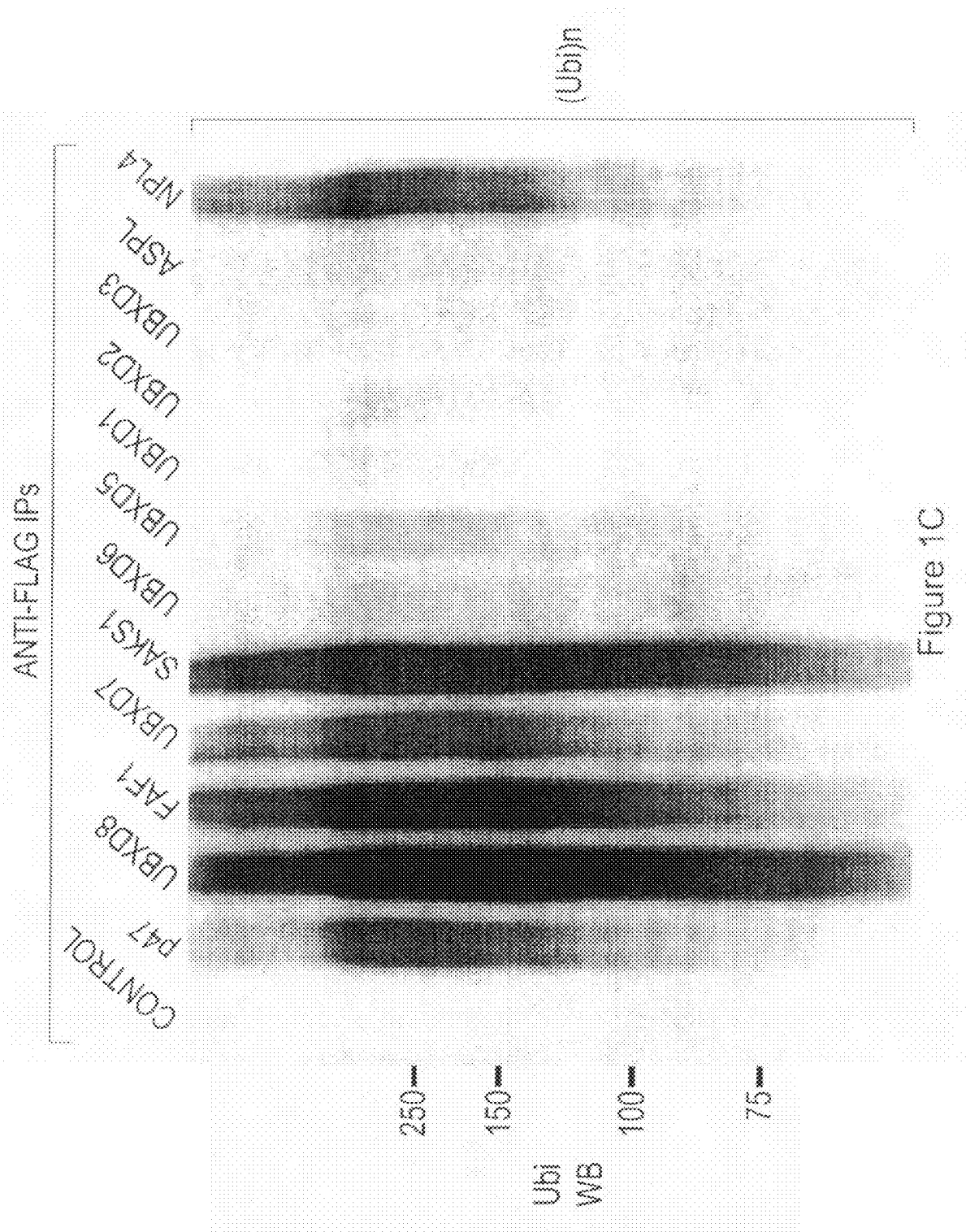

There are Two Classes of UBX Domain-Containing Proteins Based on their Ability to Bind Ubiquitinated Substrates Based on their domain composition, the human UBX proteins can be divided into two main groups (FIG. 1A). The first group includes the UBA-UBX proteins (UBXD7, UBXD8, FAF1, SAKS1, and p47), characterized by the presence of an UBA (ubiquitin-associated) domain at their N-termini. The UBA domain binds ubiquitin (Hurley et al., 2006) and Flag-tagged UBA-UBX proteins coimmunoprecipitated (preformed using a similar method described in Example 1) endogenous ubiquitin conjugates (FIG. 1C). The amount of ubiquitinated proteins present in UBA-UBX protein immunoprecipitates was amplified by proteasome inhibition with MG132 (incubating cells with 20 μM MG132 for 2 hr), suggesting that at least some of them are UPS substrates (FIG. 2A). The second group includes the UBX-only proteins, which lack the UBA domain (FIG. 1A) and the ability to bind ubiquitinated substrates (FIG. 1C).

To establish what type of ubiquitin chains are recognized by mammalian UBA-UBX proteins, Applicants searched the mass spectrometry data for ubiquitin tryptic peptides bearing GG signatures (Parker et al., 2005). Multiple spectra corresponding to ubiquitin peptides carrying a GG signature at K48 were identified, as expected for proteins targeted for proteasomal degradation (Pickart, 1997). However, it came as a surprise that a higher number of peptides carried GG signatures attached to K11. The detection of GG signature peptides by mass spectrometry is most efficient for K48 and less effective for K11 (Kirkpatrick et al., 2006), suggesting that the actual ratio of K11- to K48-linked chains could be even higher than indicated by the spectrum counts shown in FIG. 3A. It is interesting to note that K1-linked chains were detected in immunoprecipitates of all UBA-UBX proteins.

Example 3

General Features of the UBX Protein Interaction Networks

As the biological functions for most UBX proteins are largely unknown (Schuberth and Buchberger, 2008), Applicants performed a comparative MudPIT analysis of Flag-UBX protein immunoprecipitates from transiently transfected 293 cells (similar to the method described in Example 1). The resulting datasets were mined to identify interacting partners that are shared among multiple UBX protein complexes, as well as partners that are specific to a certain UBX protein.

Applicants first focused attention on known components of the p97 network. NPL4/UFD1 and p47 use a similar bipartite mechanism for binding the N-terminal domain of p97 and compete for p97 binding in vitro (Bruderer et al., 2004; Meyer et al., 2000). This led to the hypothesis that the interaction of NPL4/UFD1 and UBX proteins with p97 might be mutually exclusive. However, the bipartite p97-binding motif seems to be conserved only in SEP-UBX proteins like p47 (Bruderer et al., 2004) and p37 (Uchiyama et al., 2006), leaving open the possibility that other UBX-domain proteins use a different binding mode. Applicants confirmed both by mass spectrometry (Table 3) and by immunoblotting of Flag-p47 immunoprecipitates (FIG. 1D, 2A) that, for the most part, p47 does not form complexes with NPL4/UFD1 (using similar methods as described in Example 1). That seems to be an exception rather than the rule, as the other UBA-UBX proteins coimmunoprecipitated NPL4 and UFD1. Conversely, Flag-NPL4 coimmunoprecipitated UBA-UBX proteins, with most peptides identified for the UBA-UAS-UBX proteins, UBXD8, UBXD7, and FAF1.

Figure 1D:
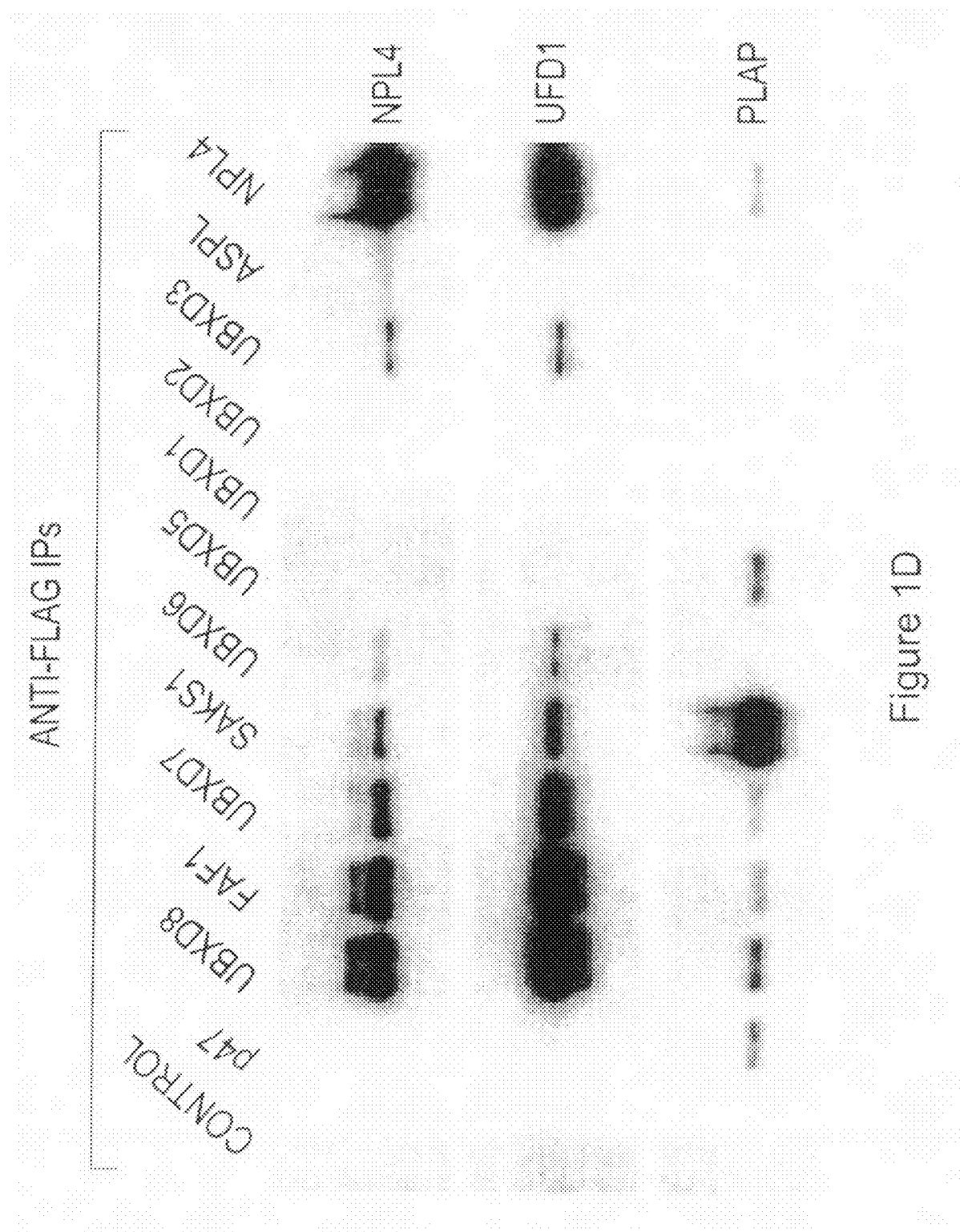

Applicants also compared the ability of UBX proteins to interact with substrate-processing cofactors of p97. VCIP135 seems to interact preferentially with SEP-UBX proteins like p47 and UBXD5 (Table 3). Indeed, two SEP-UBX proteins, p37 and p47, both require VCIP135 for their function (Uchiyama et al., 2006). PLAP, known as Ufd3/Doa1 in budding yeast, has a strong preference for co-assembling with SAKS1 (FIG. 1D). Intriguingly, even though yeast Npl4/Ufd1 and Ufd3 bind to distinct regions of Cdc48 (Rumpf and Jentsch, 2006), in our analysis the complexes that are richest in NPL4/UFD1 are poorest in PLAP and vice versa (FIG. 1D, Table 3). With the exception of a few peptides identified in SAKS1 and p47 immunoprecipitates UBE4B, the human ortholog of yeast Ufd2, was largely absent from the UBA-UBX protein and p97 immunoprecipitates (Table 3).

It has been proposed that yeast Cdc48 functions in series with other targeting factors like Rad23 to mediate processing of ubiquitin conjugates and their eventual presentation to the proteasome (Medicherla et al., 2004; Richly et al., 2005). Although this model contemplates the formation of ternary complexes, Applicants found that RAD23 and ubiquilins were largely absent from our UBX protein and p97 immunoprecipitates. However, Applicants did identify multiple proteasome subunits, most frequently the proteasome base subunits PSMC3, PSMC4, and PSMD1, which suggests that in human cells p97-substrate complexes might directly dock onto the proteasome base without another targeting factor acting as an intermediary.

Example 4

UBA-UBX Proteins Interact with a Large Variety of E3 Ubiquitin Ligases

Figure 3:
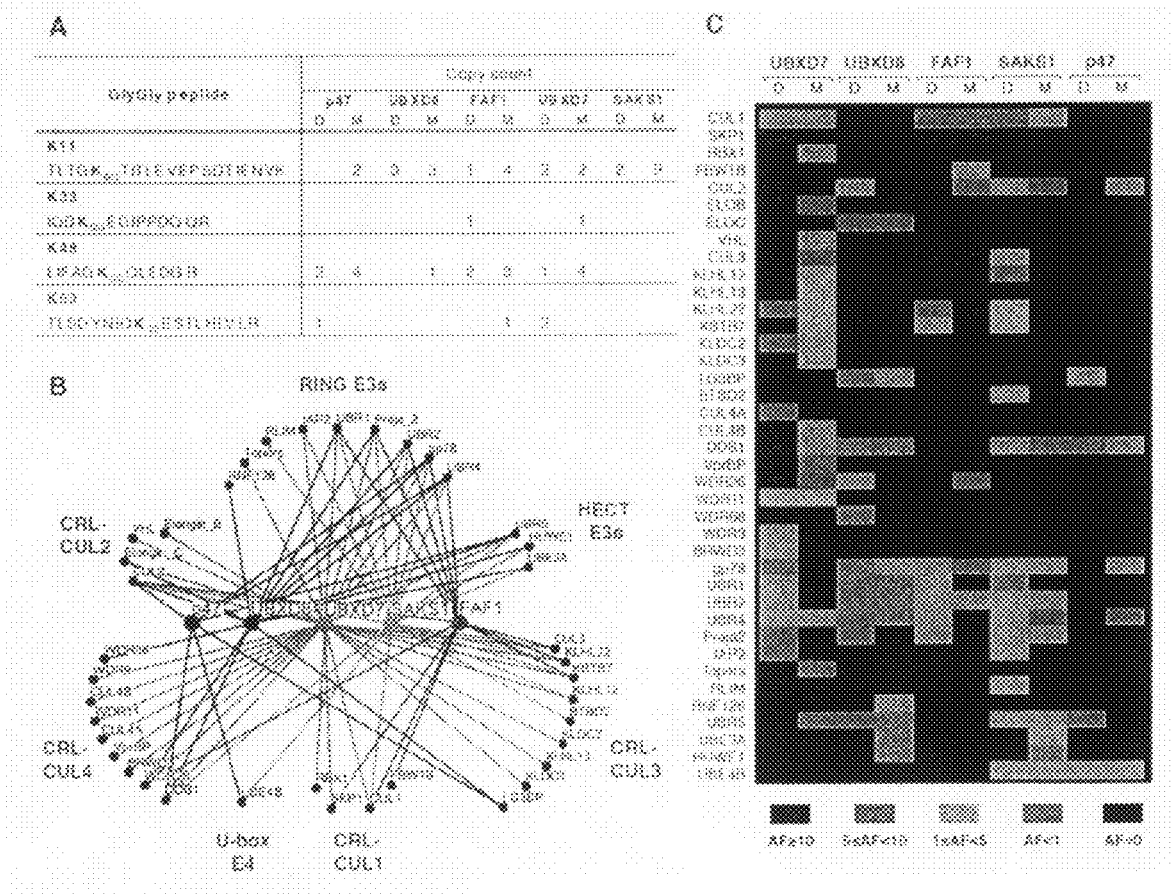
FIG. 3 shows the E3 interaction network for UBA-UBX proteins. (A) The number and type of GG signature peptides identified by mass spectrometry in Flag-UBA-UBX) immunoprecipitates is indicated. D—DMSO; M—MG132 (B) Osprey diagram illustrating the set of E3 ligases interacting with each UBA-UBX protein. (C) Quantitative representation of the interactions shown in B, obtained by calculating for each E3 ligase the abundance factor (AF) relative to p97. For details see Table 4 and its legend.

A striking observation from the comparative MudPIT analysis of Flag-(UBA-UBX) protein immunoprecipitates was their ability to interact with numerous E3 ligases as indicated qualitatively in FIG. 3B. Applicants identified multiple components of cullin-RING E3 ligase (CRL) complexes, but also single subunit RING- and HECT-domain E3s. Of these 38 ubiquitin ligases, more than a third were also identified in p97 immunoprecipitates (marked a in Table 4), confirming they belong to the p97 network.

Individual UBA-UBX proteins did not exhibit strict specificity for particular E3 ligases, but at least some E3s seemed to be enriched in certain UBA-UBX protein immunoprecipitates (FIG. 3C). Most notably, UBXD7 showed a remarkable ability to coimmunoprecipitate CUL2. Moreover, we also identified RBX1, elongin B, elongin C, and VHL in UBXD7 immunoprecipitates. In general, UBXD7 was the UBA-UBX protein that showed the most extensive interaction with CRL subunits (FIG. 2B, 3C). An UBXD7 mutant lacking the UBX domain lost the ability to interact not only with p97, but also with ubiquitinated substrates (FIG. 2C). Despite that, truncated UBXD7 largely retained its capacity to bind CUL1 and CUL2. In contrast, a p47 mutant lacking the C-terminal region could still pull down ubiquitinated proteins, but did not exhibit significant binding of cullins. This lack of correlation between ubiquitin and E3 binding, together with semi-quantitative analysis of the MudPIT data (FIG. 3C), suggest that the interaction between UBA-UBX proteins and E3 ligases is specific and not simply mediated by the ubiquitinated substrate binding to the UBA domain.

TABLE 4

Ubiquitin Ligases Identified by Mass Spectrometry in Flag-(UBA-UBX) Protein Immunoprecipitates

| PROTEIN NAME | IPI Identifier | MW (Da) | UBXD7 D | UBXD7 M | UBXD8 D | UBXD8 M | FAF1 D | FAF1 M | SAKS1 D | SAKS1 M | p47 D | p47 M |
|---|---|---|---|---|---|---|---|---|---|---|---|---|
| $CRL^{Cul1}$ components | | | | | | | | | | | | |
| Cullin 1[a] | 00014310 | 87388 | 3(3) 4.9 | 6(10) 2.9 | | | 6(8) 9.1 | 5(7) 8.4 | 5(7) 6.5 | 2(3) 1.5 | | |
| SKP1[a,c] | 00301364 | 18658 | 3(4) 30.7 | | | | 2(2) 10.7 | 4(6) 33.6 | | | | |
| RING-box protein 1, RBX1[c] | 00003386 | 12274 | | 2(2) 4.1 | | | | | | | | |
| F-box//WD-repeat protein 1B, FBW1B[a] | 00328796 | 62091 | | | | | | 2(2) 3.4 | | | | |
| $CRL^{Cul2}$ components | | | | | | | | | | | | |
| Cullin 2[a] | 00014311 | 86983 | 12(16) 26.3 | 23(199) 57.0 | 4(12) 2.4 | 8(38) 10.3 | | 6(6) 7.2 | 3(4) 3.7 | 4(11) 5.5 | | 2(2) 1.0 |
| Elongin B[a] | 00410162 | 17911 | 2(2) 16.0 | 5(7) 9.7 | | | | | | | | |
| Elongin C[a] | 00300341 | 12473 | | 8(10) 20.0 | 2(5) 7.0 | 2(3) 5.7 | | | | | | |
| Von Hippel-Lindau disease tumor suppressor, VHL | 00027969 | 24153 | | 2(2) 2.1 | | | | | | | | |
| $CRL^{Cul3}$ components | | | | | | | | | | | | |
| Cullin 3[a] | 00014312 | 88930 | 13(23) 37.0 | 16(30) 8.4 | | | 15(22) 24.6 | 12(12) 14.1 | 3(3) 2.7 | | | |
| CUL3-interacting protein I, KLHL12[a] | 00642182 | 63277 | 6(8) 18.1 | 3(3) 1.2 | | | | | 2(5) 6.4 | | | |

TABLE 4-continued

Ubiquitin Ligases Identified by Mass Spectrometry in Flag-(UBA-UBX) Protein Immunoprecipitates

| PROTEIN NAME | IPI Identifier | MW (Da) | UBXD7 D | UBXD7 M | UBXD8 D | UBXD8 M | FAF1 D | FAF1 M | SAKS1 D | SAKS1 M | p47 D | p47 M |
|---|---|---|---|---|---|---|---|---|---|---|---|---|
| BTB and Kelch domain-containing protein 2, KLHL13 | 00002398 | 73908 | | 4(4) 1.4 | | | | | | | | |
| Kelch-like protein 22. KLEIL22[b] | 00156791 | 71667 | 3(3) 6.0 | 8(8) 2.8 | | | 6(6) 8.3 | 8(8) 11.7 | 2(2) 2.3 | | | |
| Kelch repeat and BTB domain-containing protein 7, KBTB[7] | 00383044 | 77163 | | 3(3) 1.0 | | | 2(2) 2.6 | | 2(2) 2.1 | | | |
| Kelch domain-containing protein 2, KLDC2[b] | 00003793 | 46099 | 2(3) 9.3 | 4(6) 3.2 | | | | | | | | |
| Kelch domain-containing protein 3, KLDC3[b] | 00062558 | 43828 | | 3(3) 1.7 | | | | | | | | |
| Galectin-3 binding protein. LG3BP b | 00023673 | 65331 | | | 2(3) 0.8 | 2(3) 1.1 | | | | | 3(3) 1.5 | |
| BTB/POZ domain-containing protein 2. BTBD2[b] | 00022826 | 55931 | | | | | | | 2(2) 2.9 | | | |
| CRL[Cul4] components | | | | | | | | | | | | |
| Cullin 4A | 00419273 | 87722 | 5(6) 9.8 | | | | | | | | | |
| Cullin 4B | 00643885 | 102756 | 7(9) 12.5 | 10(11) 2.7 | | | | | | | | |
| DNA damage-binding protein I. DDB1[a] | 00293464 | 127030 | 11(11) 12.4 | 13(13) 2.6 | 2(2) 0.3 | 3(4) 0.7 | | | 2(2) 1.3 | 2(2) 0.7 | 2(2) 0.5 | 3(3) 1.0 |
| DDB1- and CUL4-associated factor I. VprBP | 00329528 | 168936 | | 3(4) 0.6 | | | | | | | | |
| CUL4- and DDB I-associated WDR protein 2, WDR26[a] | 00414197 | 58604 | 12(19) 46.4 | 9(17) 7.2 | 2(4) 1.2 | | | 5(5) 8.9 | | | | |
| Bromodomain and WD-repeat domain-containing protein 2, WDR 1 I | 00412224 | 136685 | 2(2) 2.1 | 5(7) 1.3 | | | | | | | | |
| WD repeat protein Anti homolog. WDR68 | 00006754 | 38926 | | | 2(2) 0.9 | | | | | | | |
| Bromodomain and WD-repeat domain-containing protein 1. WDR9[b] | 00250716 | 257221 | 3(4) 2.2 | | | | | | | | | |
| Bromodomain and WD-repeat domain-containing protein 3, BRWD3[b] | 00167547 | 203596 | 2(2) 1.4 | | | | | | | | | |
| Other RING-type E3 ligases | | | | | | | | | | | | |
| gp78[a] | 00423874 | 72996 | 3(3) 5.9 | | 2(2) 0.5 | 4(6) 1.9 | 2(2) 2.7 | 4(6) 8.6 | 3(3) 3.3 | 3(6) 3.6 | 3(3) 1.7 | |
| UBR1 | 00217405 | 200209 | 2(2) 1.4 | | 3(3) 0.3 | 3(3) 0.4 | 2(2) 1.0 | | 2(2) 0.8 | | | |
| UBR2 | 00217407 | 200539 | 2(3) 2.1 | | 3(5) 0.4 | 2(2) 0.2 | 4(4) 2.0 | 2(2) 1.0 | 5(7) 2.8 | 3(6) 1.3 | | |
| Retinoblastoma-associated factor 600, UBR4[a] | 00643014 | 573849 | 12(18) 4.5 | 41(49) 2.1 | 3(5) 0.2 | 6(6) 0.3 | 9(9) 1.6 | 47(56) 10.2 | 18(27) 3.8 | 30(74) 5.7 | 2(3) 0.2 | |
| Praja 2[a] | 00006557 | 78242 | 2(3) 5.5 | | 3(3) 0.7 | | 3(3) 3.8 | | 3(3) 3.1 | 2(2) 1.1 | | |
| Baculoviral IAP repeat-containing protein 2, IAP2 | 00013418 | 69900 | 3(3) 6.1 | | | | | | 2(2) 2.3 | | | |
| E3 ubiquitin-protein ligase Topors | 00396077 | 119198 | | 3(3) 0.6 | | | | | | | | |
| RING finger protein 12. RLIM | 00386464 | 68549 | | | | | | | 2(3) 3.5 | | | |
| RING finger protein 126. RNE126[b] | 00155562 | 33862 | | | 2(2) 1.4 | | | | | | | |

TABLE 4-continued

Ubiquitin Ligases Identified by Mass Spectrometry in Flag-(UBA-UBX) Protein Immunoprecipitates

| PROTEIN NAME | IPI Identifier | MW (Da) | UBXD7 D | UBXD7 M | UBXD8 D | UBXD8 M | FAF1 D | FAF1 M | SAKS1 D | SAKS1 M | p47 D | p47 M |
|---|---|---|---|---|---|---|---|---|---|---|---|---|
| HECT E3 ligases | | | | | | | | | | | | |
| EDD1/UBR[5] | 00026320 | 309352 | 2(2) 0.2 | 3(3) 0.2 | 9(10) 0.8 | | | | 9(10) 2.6 | 9(14) 2.0 | 2(2) 0.2 | |
| E6AP ubiquitin-protein ligase, UBE3A | 00011609 | 100646 | | | 2(2) 0.5 | | | | | 4(5) 2.2 | | |
| E3 ubiquitin-protein ligase1-HUWE1 | 00456919 | 481896 | | | 6(6) 0.3 | | | | | 4(7) 0.6 | | |
| U-box E4 ligase | | | | | | | | | | | | |
| Ubiquitin conjugation factor E4 B, UBE4B (Ufd2ortholog) | 00005715 | 146184 | | | | | | | 2(2) 1.1 | 5(5) 1.5 | 5(5) 1.1 | 5(5) 1.4 |

[a]E3 ligases/subunits identified also in p97-Myc immunoprecipitates by one spectral count or more.
[b]Putative E3 ligases/subunits that have not been yet demonstrated to possess ubiquitin-ligase activity or to be part of an E3 ligase complex. They were included in the list because their domain composition suggests they are likely to perform such function.
[c]SKP I and RBX I can form CRL-type of complexes with multiple cullins.

The corresponding International Protein Index (IPI) identifiers are specified and further information about the respective proteins can be found at http://www.ebi.ac.uk/IPI/IPIhelp.html. Whenever multiple isoforms were identified, the MW of the longest isoform is shown. The sequence count, the spectrum count (in parenthesis) and the abundance factor (bold) are indicated for each interacting protein. The exact sequence of the peptides identified is available upon request.
D—DMSO,
M—MG 132.
The abundance factors (AF) were calculated by normalizing the spectrum count for the each E3 I igase to the spectrum count for p97 in the respective immunoprecipitate using the following formula: AF = 100 × (Spectrum count E3/MW E3)/(Spectrum count p97/6 × MW p97)
The molecular weight for p97 has been amplified by six, because p97 exists as hexamers.

Example 5

UBXD7 Interacts with HIF1α in a Manner that is Largely Independent of p97 p97 cofactors like p47 and NPL4/UFD1 mediate the interaction between p97 and its ubiquitinated targets (Ye, 2006). By MudPIT analysis of individual UBX-protein immunoprecipitates, Applicants sought to identify p97 targets specific for these cofactors, and thereby unravel which p97 functions they regulate. Therefore, it was interesting to identify eight distinct HIF1α peptides in Flag-UBXD7 immunoprecipitates from cells in which the proteasome activity was inhibited with MG132 (FIG. 4A). HIF1, a heterodimeric transcription factor that consists of HIF1α and HIF1α subunits, regulates transcription in response to changes in $O_2$ concentration. $O_2$-dependent degradation of HIF1α is mediated by prolyl-hydroxylase, the CUL2/VHL ubiquitin ligase, and the proteasome (Ivan and Kaelin, 2001). Thus, Applicants decided to pursue HIF1α as a potential p97/UBXD7 substrate.

Among the UBA-UBX proteins, UBXD7 was by far the most efficient in coimmunoprecipitating endogenous HIF1α, which was detected as a ubiquitinated ladder using anti-HIF1α antibodies (FIG. 4B). HIF1α is scarce in normoxia (Huang et al., 1996), hence the interaction between UBXD7 and HIF1α was only detectable after MG132 treatment, which causes accumulation of ubiquitinated HIF1α. Applicants confirmed the specificity of the HIF1α antibodies by comparing the signal in total cell extracts from cells treated or not with HIF1α siRNA, both in the presence and in the absence of MG132 (FIG. 4C). This indicated the presence of a cross-reacting band that partially overlaps with full length HIF1α, marked with * in all the panels showing HIF1α in total cell extracts. The cross-reacting band was absent from immunoprecipitates (FIG. 4D). Proteasome inhibition also caused accumulation of HIF1α partial degradation products (FIG. 4C) that migrated faster than expected for the full-length protein (92.7 kDa), some of which also coimmunoprecipitated with UBXD7 (FIG. 4B).

Total extracts of cells treated with siRNA were prepared using buffer B (50 mM HEPES/KOH, pH 7.2; 400 mM NaCl; 1% NP-40; 0.2 mM EDTA; 10% glycerol; protease inhibitors) to enable extraction of nuclear HIF1α. siRNA oligonucleotides purchased from Dharmacon were transfected into HeLa cells using Oligofectamine (Invitrogen) and the protocol suggested by the manufacturer. See Table 5 for a list of the siRNAs used. The cells were lysed 48 hours after siRNA transfection.

Applicants next tested whether the interaction between UBXD7 and HIF1α depends on p97. Depletion of p97 by siRNA did not alter significantly the interaction of UBXD7 with HIF1α or cullins, but it drastically reduced the association of UBXD7 with NPL4 and UFD1 (FIG. 4D). We therefore conclude that UBXD7 interaction with the substrate and E3s does not depend on p97/NPL4/UFD1.

TABLE 5 siRNAs Used in this Study

| Target gene | Dharmacon Catalog No. | Name/Sense Sequence |
|---|---|---|
| HIF1ct α[a] | | CUGAUGACCAGCAACUUGAdTdT (SEQ ID NO: 33) |
| Luciferase | P-002099-01 | CAUUCUAUCCUCUAGAGGAUGdTdT (SEQ ID NO: 34) |
| p97 | M-008727-01 | siGENOME SMART pool, Human VCP |
| UBXD7 | M-023533-00 | siGENOME SMART pool, Human UBXD7 |
| UBXD8 | D-010649-03 | siGENOME duplex, Human UBXD8 |

[a]Elvidge, G. P., Glenny, L., Appelhoff, R. J., Ratcliffe, P. J., Ragoussis. J., and Gleadle, J. M. (2006). Concordant regulation of gene expression by hypoxia and 2-oxoglutarate-dependent dioxygenase inhibition: the role of HIF-1 alpha.HIF-2alpha, and other pathways. J Biol Chem 281, 15215-15226.

Example 6

UBXD7 Recruits p97 to HIF1α

To validate that the interaction of UBXD7 with HIF1α occurs within the p97 network, we showed that p97 itself coimmunoprecipitated endogenous HIF1α (FIG. 5A). Interestingly, the HIF1α that immunoprecipitated with p97 was more extensively polyubiquitinated than the pool bound to UBXD7 (compare FIG. 5A, B with FIG. 4B, D). The accumulation of ubiquitinated HIF1α in p97 immunoprecipitates after proteasome inhibition correlated with increased amounts of endogenous UBXD7 bound to p97 (FIG. 5A), suggesting that UBXD7 binding to p97 might depend on the availability of substrate. Further support for this idea came from gel filtration experiments of HeLa cell extracts in which all proteins were expressed endogenously (FIG. 5C).

HeLa cell lysates in buffer C (50 mM HEPES/KOH, pH 7.2; 5 mM Mg(OAc)$_2$; 70 mM KOAc; 0.2% Triton X-10; 5% glycerol; 0.2 mM EDTA; protease inhibitors) were fractionated on a Superdex 200 column (GE Healthcare). The collected fractions were concentrated by TCA precipitation prior to western blot analysis. The molecular weight standards were Thyroglobulin (670 kDa; Bio-Rad), Apoferritin (443 kDa; Sigma), and β-globulin (158 kDa; Bio-Rad).

Applicants observed two fractionation peaks for endogenous UBXD7, only one of which overlapped with p97. In contrast, NPL4 and UFD1 fractionation closely resembled p97. This fractionation pattern indicated that the default state for NPL4/UFD1 was p97-bound, whereas only a fraction of UBXD7 was p97-bound, possibly in response to a stimulus such as interaction with a substrate. Indeed, the accumulation of ubiquitinated substrates upon proteasome inhibition by MG 132 resulted in a shift of UBXD7 towards p97-positive fractions (FIG. 7A), a phenomenon that was reverted upon p97 depletion (FIG. 7B).

If the substrate-ligase complex binds UBXD7, which in turn binds p97, HIF1α association with p97 should depend on UBXD7. Indeed, the ability of p97 to coimmunoprecipitate endogenous HIF1α-ubiquitin conjugates was lost in cells treated with UBXD7 siRNA, using similar method as described in Example 5 (FIG. 5B). In contrast, UBXD7 depletion had no significant effect on NPL4, UFD1 or polyubiquitin binding to p97. While CUL1 binding to p97 was also unaffected by UBXD7 depletion, we observed a significant reduction of CUL2 binding (FIG. 5B), consistent with UBXD7 being the best CUL2 binder among UBA-UBX proteins (FIG. 2B). This suggests that the UBA-UBX adaptor mediates p97 interaction with the substrate and the corresponding E3 ligase.

Example 7

HIF1α is a p97 Substrate

The endogenous HIF1α that interacted with both UBXD7 and p97 was mainly ubiquitinated and accumulated upon proteasome inhibition (FIG. 4B, 4D, 5A), supporting the idea that it was destined for UPS-dependent degradation.

To test whether p97 regulates HIF1α degradation, we performed siRNA-mediated depletion experiments (using similar methods as described in Example 5). FIG. 6A shows the effect of various siRNA pools on HIF1α levels in total cell extracts. p97 depletion caused accumulation of endogenous HIF1α as species>100 kDa and >>250 kDa, and this effect was amplified by brief exposure to MG132 (FIG. 6A, compare lane 1 with 2 and lane 8 with 9). However, p97 depletion did not promote HIF1α accumulation as effectively as proteasome inactivation. This could be due to various reasons: i) the low amounts of p97 that remain in the cell after siRNA treatment may be sufficient to promote HIF1α degradation, ii) other targeting factors, like Rpn10/PSMD4, RAD23, or ubiquilins may be able to partially compensate for the lack of p97, or iii) only a subset of ubiquitinated HIF1α molecules depend on p97 for degradation. p97 depletion also caused a mild increase in the total pool of ubiquitinated proteins (FIG. 6A, compare lane 1 with 2). The p97 siRNA pool did not alter HIF1α mRNA levels (FIG. 6B), indicating that the observed effects at the protein level were most likely due to perturbations in HIF1α degradation.

As a measure of HIF1α activity, Applicants analyzed the levels of carbonic anhydrase IX (CA IX), an established target of HIF1α transcriptional activity (Wykoff et al., 2000). CA 1× protein levels were very low in normoxia (FIG. 6A, lane 1), but accumulated in cells depleted of p97 (FIG. 6A, lanes 2 and 9). It has been reported by several groups that HIF1α that accumulates in the presence of MG132 is transcriptionally inactive (Kaluz et al., 2007) and this explains why MG132 had a major effect on HIF1α levels, but little effect on CA IX levels.

Applicants next confirmed that individual p97 siRNA oligonucleotides behaved similar to the p97 siRNA pool (FIG. 6C, lanes 8-12). Even if the amplitude of the effect varied among siRNAs, the general trend was the same that p97 depletion led to HIF1α accumulation. Taken together these results suggest that efficient HIF1α degradation depends on p97, thereby establishing HIF1α as the first endogenous substrate of mammalian p97 that is not associated with the ER.

Given that UBXD7 recruits HIF1α to p97 (FIG. 5B), it seemed likely that UBXD7 depletion would phenocopy p97 depletion. Thus, it was unexpected to see that UBXD7 depletion caused a reduction in both full length and ubiquitinated HIF1α (FIG. 6A). The contrast between p97 and UBXD7 depletion was most obvious upon brief treatment with MG132 (FIG. 6A, lanes 9-11). This result was confirmed by three of the four siRNA oligonucleotides in the UBXD7 siRNA pool (FIG. 6C, compare lane 2 with lanes 3, 4, 6, 7). Moreover, when the cells were treated with a combination of UBXD7 and p97 siRNAs, UBXD7 depletion seemed to partially offset the lack of p97 (FIG. 6A, FIG. 8). This suggests that in the absence of UBXD7, HIF1α does not engage the p97 network and is more readily available to alternative proteasome receptors.

The protein levels of CA IX perfectly mimicked those of HIF1α (FIG. 6A); they were highest in cells depleted of p97 (lanes 2 and 9), lowest in cells depleted of UBXD7 (lanes 3-5 and 10, 11), and intermediate in cells depleted of both UBXD7 and p97 (lanes 6 and 12). As for p97, the UBXD7 siRNA pool did not have a significant effect on HIF1α mRNA levels (FIG. 6B; Primers in Table 6).

TABLE 6

Primers Used for RT-PCR

| Name | Sequence | SEQ ID NO: |
|---|---|---|
| HIF1α forward | 5'-GAT GTA ATG CTC CCC TCA CCC AAC-3' | 35 |
| HIF1α reverse | 5'-CAC TGG GAC TAT TAG GCT CAG GTG-3' | 36 |
| 18S rRNA forward | 5'-CGG ACA CGG ACA GGA TTG ACA GAT TG-3' | 37 |
| 18S rRNA revers | 5'-GCA CAC GCT GAG CCA GTC AGT GTA G-3' | 38 |

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A method for identifying an active agent that regulates a complex comprising a UBXD7 polypeptide and a HIF1 α polypeptide, the method comprising:
   (i) providing an isolated UBXD7 polypeptide and an isolated HIF1 α polypeptide in a reaction mixture;
   (ii) adding a test agent to the reaction mixture; and
   (iii) determining whether the test agent interferes with or promotes complex formation between the UBXD7 polypeptide and the HIF1 α polypeptide.

2. The method of claim 1, wherein the complex further comprises a p97 polypeptide.

3. The method of claim 1, wherein the complex further comprises a CUL2 ubiquitin ligase or a subunit of a CUL2 ubiquitin ligase.

4. The method of claim 1, wherein the complex further comprises a NPL4 polypeptide and an UFD1 polypeptide.

5. The method of claim 1, wherein the step of determining whether the test agent interferes with or promotes complex formation is selected from FRET, FACS, a surface plasmon resonance system, a electrophoretic mobility shift assay, an immunoassay for protein binding, and other protein-protein binding assays.

6. The method of claim 1, wherein the test agent is selected from a small molecule, an aptamer, a polypeptide, a polynucleotide, or an antibody.

7. A method for identifying an active agent that regulates a HIF1 α activity in a cell, the method comprising:
   (i) providing a cell, wherein the cell is genetically modified to provide exogenous expression of an UBXD7 polypeptide and a HIF1 α polypeptide;
   (ii) contacting the cell with a test agent; and
   (iii) determining whether the test agent inhibits or promotes an activity of HIF1 α in the cell.

8. The method of claim 7, wherein the cell is further modified to provide exogenous expression of a p97 polypeptide.

9. The method of claim 7, wherein the cell is further modified to provide exogenous expression of a CUL2 ubiquitin ligase or a subunit of a CUL2 ubiquitin ligase.

10. The method of claim 7, wherein the cell is further modified to provide exogenous expression of a NPL4 polypeptide and an UFD1 polypeptide.

11. The method of claim 7, wherein the step of determining whether the test agent inhibits or promotes HIF1 α activity comprises measuring the expression of an HIF1 α-regulated gene.

12. The method of claim 7, wherein the test agent is selected from a small molecule, an aptamer, a polynucleotide, a polypeptide, and antibody, or an siRNA construct.

* * * * *

SEQUENCE LISTING

<160> NUMBER OF SEQ ID NOS: 46

<210> SEQ ID NO 1
<211> LENGTH: 826
<212> TYPE: PRT
<213> ORGANISM: Homo sapiens

<400> SEQUENCE: 1

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

-continued

```
Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575
```

```
Phe Asp Gln Leu Ser Pro Leu Glu Ser Ser Ala Ser Pro Glu Ser
            580                 585                 590
Ala Ser Pro Gln Ser Thr Val Thr Val Phe Gln Gln Thr Gln Ile Gln
        595                 600                 605
Glu Pro Thr Ala Asn Ala Thr Thr Thr Ala Thr Thr Asp Glu Leu
    610                 615                 620
Lys Thr Val Thr Lys Asp Arg Met Glu Asp Lys Ile Leu Ile Ala
625                 630                 635                 640
Ser Pro Ser Pro Thr His Ile His Lys Glu Thr Ser Ala Thr Ser
                645                 650                 655
Ser Pro Tyr Arg Asp Thr Gln Ser Arg Thr Ala Ser Pro Asn Arg Ala
            660                 665                 670
Gly Lys Gly Val Ile Glu Gln Thr Glu Lys Ser His Pro Arg Ser Pro
        675                 680                 685
Asn Val Leu Ser Val Ala Leu Ser Gln Arg Thr Thr Val Pro Glu Glu
    690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Gly Thr
                725                 730                 735
Leu Leu Gln Gln Pro Asp Asp His Ala Ala Thr Thr Ser Leu Ser Trp
            740                 745                 750
Lys Arg Val Lys Gly Cys Lys Ser Ser Glu Gln Asn Gly Met Glu Gln
        755                 760                 765
Lys Thr Ile Ile Leu Ile Pro Ser Asp Leu Ala Cys Arg Leu Leu Gly
    770                 775                 780
Gln Ser Met Asp Glu Ser Gly Leu Pro Gln Leu Thr Ser Tyr Asp Cys
785                 790                 795                 800
Glu Val Asn Ala Pro Ile Gln Gly Ser Arg Asn Leu Leu Gln Gly Glu
                805                 810                 815
Glu Leu Leu Arg Ala Leu Asp Gln Val Asn
            820                 825

<210> SEQ ID NO 2
<211> LENGTH: 2481
<212> TYPE: DNA
<213> ORGANISM: Homo sapiens

<400> SEQUENCE: 2
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc tttatttga agccttgga tggttttgtt      300 atggttctca gagatgatgg tgacatgatt tacatttctg ataatgtgaa caaatacatg     360
ggattaactc agtttgaact aactggacac agtgtgtttg atttactca tccatgtgac     420 catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca cagtaaccaa acctcagtgt gggtataaga aaccaccat gacctgcttg      660 gtgctgattt gtgaacccat tcctcaccca tcaaatattg aaattccttt agatagcaag     720
```

```
actttcctca gtcgacacag cctggatatg aaattttctt attgtgatga aagaattacc    780
gaattgatgg gatatgagcc agaagaactt ttaggccgct caatttatga atattatcat    840
gctttggact ctgatcatct gaccaaaact catcatgata tgtttactaa aggacaagtc    900
accacaggac agtacaggat gcttgccaaa agaggtggat atgtctgggt tgaaactcaa    960
gcaactgtca tatataacac caagaattct caaccacagt gcattgtatg tgtgaattac   1020
gttgtgagtg gtattattca gcacgacttg attttctccc ttcaacaaac agaatgtgtc   1080
cttaaaccgg ttgaatcttc agatatgaaa atgactcagc tattccaccaa agttgaatca   1140
gaagatacaa gtagcctctt tgacaaactt aagaaggaac ctgatgcttt aactttgctg   1200
gccccagccg ctggagacac aatcatatct ttagattttg gcagcaacga cacagaaact   1260
gatgaccagc aacttgagga agtaccatta tataatgatg taatgctccc ctcacccaac   1320
gaaaaattac agaatataaa tttggcaatg tctccattac ccaccgctga acgccaaag    1380
ccacttcgaa gtagtgctga ccctgcactc aatcaagaag ttgcattaaa attagaacca   1440
aatccagagt cactggaact ttcttttacc atgccccaga ttcaggatca gacacctagt   1500
ccttccgatg gaagcactag acaaagttca cctgagccta atagtcccag tgaatattgt   1560
ttttatgtgg atagtgatat ggtcaatgaa ttcaagttgg aattggtaga aaacttttt    1620
gctgaagaca cagaagcaaa gaacccattt tctactcagg acacagattt agacttggag   1680
atgttagctc cctatatccc aatgatgat gacttccagt tacgttcctt cgatcagttg    1740
tcaccattag aaagcagttc cgcaagccct gaaagcgcaa gtcctcaaag cacagttaca   1800
gtattccagc agactcaaat acaagaacct actgctaatg ccaccactac cactgccacc   1860
actgatgaat taaaacagt gacaaaagac cgtatggaag acattaaaat attgattgca    1920
tctccatctc ctaccacat acataaagaa actactagtg ccacatcatc accatataga    1980
gatactcaaa gtcggacagc ctcaccaaac agagcaggaa aaggagtcat agaacagaca   2040
gaaaaatctc atccaagaag ccctaacgtg ttatctgtcg ctttgagtca agaactaca    2100
gttcctgagg aagaactaaa tccaaagata ctagctttgc agaatgctca gagaaagcga   2160
aaaatggaac atgatggttc actttttcaa gcagtaggaa ttggaacatt attacagcag   2220
ccagacgatc atgcagctac tacatcactt tcttggaaac gtgtaaaagg atgcaaatct   2280
agtgaacaga atggaatgga gcaaaagaca attattttaa taccctctga tttagcatgt   2340
agactgctgg ggcaatcaat ggatgaaagt ggattaccac agctgaccag ttatgattgt   2400
gaagttaatg ctcctataca aggcagcaga aacctactgc agggtgaaga attactcaga   2460
gctttggatc aagttaactg a                                             2481
```

<210> SEQ ID NO 3
<211> LENGTH: 489
<212> TYPE: PRT
<213> ORGANISM: Homo sapiens

<400> SEQUENCE: 3

Met Ala Ala His Gly Gly Ser Ala Ala Ser Ala Leu Lys Gly Leu
1               5                   10                  15

Ile Gln Gln Phe Thr Thr Ile Thr Gly Ala Ser Glu Ser Val Gly Lys
            20                  25                  30

His Met Leu Glu Ala Cys Asn Asn Leu Glu Met Ala Val Thr Met
        35                  40                  45

```
Phe Leu Asp Gly Gly Gly Ile Ala Glu Glu Pro Ser Thr Ser Ser Ala
 50                  55                  60

Ser Val Ser Thr Val Arg Pro His Thr Glu Glu Val Arg Ala Pro
 65                  70                  75                  80

Ile Pro Gln Lys Gln Glu Ile Leu Val Glu Pro Glu Pro Leu Phe Gly
                 85                  90                  95

Ala Pro Lys Arg Arg Arg Pro Ala Arg Ser Ile Phe Asp Gly Phe Arg
            100                 105                 110

Asp Phe Gln Thr Glu Thr Ile Arg Gln Glu Gln Glu Leu Arg Asn Gly
        115                 120                 125

Gly Ala Ile Asp Lys Lys Leu Thr Thr Leu Ala Asp Leu Phe Arg Pro
    130                 135                 140

Pro Ile Asp Leu Met His Lys Gly Ser Phe Glu Thr Ala Lys Glu Cys
145                 150                 155                 160

Gly Gln Met Gln Asn Lys Trp Leu Met Ile Asn Ile Gln Asn Val Gln
                165                 170                 175

Asp Phe Ala Cys Gln Cys Leu Asn Arg Asp Val Trp Ser Asn Glu Ala
            180                 185                 190

Val Lys Asn Ile Ile Arg Glu His Phe Ile Phe Trp Gln Val Tyr His
        195                 200                 205

Asp Ser Glu Glu Gly Gln Arg Tyr Ile Gln Phe Tyr Lys Leu Gly Asp
    210                 215                 220

Phe Pro Tyr Val Ser Ile Leu Asp Pro Arg Thr Gly Gln Lys Leu Val
225                 230                 235                 240

Glu Trp His Gln Leu Asp Val Ser Ser Phe Leu Asp Gln Val Thr Gly
                245                 250                 255

Phe Leu Gly Glu His Gly Gln Leu Asp Gly Leu Ser Ser Ser Pro Pro
            260                 265                 270

Lys Lys Cys Ala Arg Ser Glu Ser Leu Ile Asp Ala Ser Glu Asp Ser
        275                 280                 285

Gln Leu Glu Ala Ala Ile Arg Ala Ser Leu Gln Glu Thr His Phe Asp
    290                 295                 300

Ser Thr Gln Thr Lys Gln Asp Ser Arg Ser Asp Glu Glu Ser Glu Ser
305                 310                 315                 320

Glu Leu Phe Ser Gly Ser Glu Glu Phe Ile Ser Val Cys Gly Ser Asp
                325                 330                 335

Glu Glu Glu Glu Val Glu Asn Leu Ala Lys Ser Arg Lys Ser Pro His
            340                 345                 350

Lys Asp Leu Gly His Arg Lys Glu Glu Asn Arg Arg Pro Leu Thr Glu
        355                 360                 365

Pro Pro Val Arg Thr Asp Pro Gly Thr Ala Thr Asn His Gln Gly Leu
    370                 375                 380

Pro Ala Val Asp Ser Glu Ile Leu Glu Met Pro Pro Glu Lys Ala Asp
385                 390                 395                 400

Gly Val Val Glu Gly Ile Asp Val Asn Gly Pro Lys Ala Gln Leu Met
                405                 410                 415

Leu Arg Tyr Pro Asp Gly Lys Arg Glu Gln Ile Thr Leu Pro Glu Gln
            420                 425                 430

Ala Lys Leu Leu Ala Leu Val Lys His Val Gln Ser Lys Gly Tyr Pro
        435                 440                 445

Asn Glu Arg Phe Glu Leu Leu Thr Asn Phe Pro Arg Arg Lys Leu Ser
    450                 455                 460
```

His Leu Asp Tyr Asp Ile Thr Leu Gln Glu Ala Gly Leu Cys Pro Gln
465                 470                 475                 480

Glu Thr Val Phe Val Gln Glu Arg Asn
                485

<210> SEQ ID NO 4
<211> LENGTH: 1470
<212> TYPE: DNA
<213> ORGANISM: Homo sapiens

<400> SEQUENCE: 4

| | | |
|---|---|---|
| atggctgccc acggggctc cgcggcgtcc tcggcgctga aggggttaat tcaacagttc | 60 |
| accaccatta ccggtgcaag tgaaagtgta ggaaaacata tgcttgaagc gtgcaacaat | 120 |
| aatctggaaa tggcagtcac tatgttttg gatggtggag gaatcgctga agagcccagt | 180 |
| accagttcag caagtgtctc tactgtcaga ccacacacag aagaagaagt tcgtgcccca | 240 |
| attcctcaaa agcaggaaat actggtgaa ccagaaccat tatttggtgc tcctaaaaga | 300 |
| cgacggcctg cacgttcaat ttttgatggt ttccgggatt ttcagactga aactattcgg | 360 |
| caagaacaag aattaagaaa tggaggagct atcgataaga aattaactac ccttgcagat | 420 |
| ctattccggc cacccattga tttgatgcat aaaggcagct ttgaaacagc caaagagtgt | 480 |
| ggccagatgc aaaataagtg gctgatgata acattcaaa atgttcaaga ctttgcatgt | 540 |
| cagtgcctca accgcgatgt gtggagcaac gaagctgtga gaatattat ccgggaacat | 600 |
| ttcattttct ggcaggttta tcatgacagt gaggaaggtc agagatacat acagtttat | 660 |
| aagttagggg atttccccta tgtttccata ttggacccac ggacaggtca gaagctagta | 720 |
| gaatggcacc agttagatgt atcttctttc ttggaccaag tgacgggatt tctgggtgaa | 780 |
| catggacaac tggatggact ttctagcagt cccccccaaaa aatgtgcccg ttcagagagc | 840 |
| cttatagatg caagtgaaga cagccagcta gaagctgcca tcagagcctc cttacaagaa | 900 |
| acacattttg attcaacaca gacaaaacag gatagccgct cagatgaaga atctgaatct | 960 |
| gaacttttt ctggcagtga ggagttcata tccgtttgtg ctctgatga agaagaagag | 1020 |
| gtagagaatc ttgccaagtc cagaaagtct ccccacaaag atttggggca tagaaaagag | 1080 |
| gagaatagaa ggccgctgac tgagccacca gtcagaactg atcctggaac agccacaaac | 1140 |
| caccaaggat tgccagctgt ggattcagag atactggaga tgccacctga aaaagcagat | 1200 |
| ggagtagtgg aggggataga tgtaaatgga ccaaaagcac agctgatgtt gcggtatcca | 1260 |
| gatggaaaaa gggaacagat cactcttcca gagcaagcta aactgctagc tttggtgaag | 1320 |
| cacgtgcagt ctaaaggata cccaaatgaa cgttttgaac ttctcaccaa ctttcctcga | 1380 |
| aggaaattat ctcatctgga ctatgatatt acattgcaag aggcaggcct ttgtcctcaa | 1440 |
| gagactgtct ttgtacagga agaaattaa | 1470 |

<210> SEQ ID NO 5
<211> LENGTH: 907
<212> TYPE: PRT
<213> ORGANISM: Homo sapiens

<400> SEQUENCE: 5

Met Glu Ser Ala Ile Ala Glu Gly Gly Ala Ser Arg Phe Ser Ala Ser
1               5                   10                  15

Ser Gly Gly Gly Gly Ser Arg Gly Ala Pro Gln His Tyr Pro Lys Thr
            20                  25                  30

-continued

```
Ala Gly Asn Ser Glu Phe Leu Gly Lys Thr Pro Gly Gln Asn Ala Gln
         35                  40                  45

Lys Trp Ile Pro Ala Arg Ser Thr Arg Arg Asp Asp Asn Ser Ala Ala
 50                  55                  60

Asn Asn Ser Ala Asn Glu Lys Glu Arg His Asp Ala Ile Phe Arg Lys
 65                  70                  75                  80

Val Arg Gly Ile Leu Asn Lys Leu Thr Pro Glu Lys Phe Asp Lys Leu
                 85                  90                  95

Cys Leu Glu Leu Leu Asn Val Gly Val Glu Ser Lys Leu Ile Leu Lys
                100                 105                 110

Gly Val Ile Leu Leu Ile Val Asp Lys Ala Leu Glu Pro Lys Tyr
             115                 120                 125

Ser Ser Leu Tyr Ala Gln Leu Cys Leu Arg Leu Ala Glu Asp Ala Pro
    130                 135                 140

Asn Phe Asp Gly Pro Ala Ala Glu Gly Gln Pro Gly Gln Lys Gln Ser
145                 150                 155                 160

Thr Thr Phe Arg Arg Leu Leu Ile Ser Lys Leu Gln Asp Glu Phe Glu
                165                 170                 175

Asn Arg Thr Arg Asn Val Asp Val Tyr Asp Lys Arg Glu Asn Pro Leu
                180                 185                 190

Leu Pro Glu Glu Glu Gln Arg Ala Ile Ala Lys Ile Lys Met Leu
            195                 200                 205

Gly Asn Ile Lys Phe Ile Gly Glu Leu Gly Lys Leu Asp Leu Ile His
            210                 215                 220

Glu Ser Ile Leu His Lys Cys Ile Lys Thr Leu Leu Glu Lys Lys Lys
225                 230                 235                 240

Arg Val Gln Leu Lys Asp Met Gly Glu Asp Leu Glu Cys Leu Cys Gln
                245                 250                 255

Ile Met Arg Thr Val Gly Pro Arg Leu Asp His Glu Arg Ala Lys Ser
                260                 265                 270

Leu Met Asp Gln Tyr Phe Ala Arg Met Cys Ser Leu Met Leu Ser Lys
            275                 280                 285

Glu Leu Pro Ala Arg Ile Arg Phe Leu Leu Gln Asp Thr Val Glu Leu
            290                 295                 300

Arg Glu His His Trp Val Pro Arg Lys Ala Phe Leu Asp Asn Gly Pro
305                 310                 315                 320

Lys Thr Ile Asn Gln Ile Arg Gln Asp Ala Val Lys Asp Leu Gly Val
                325                 330                 335

Phe Ile Pro Ala Pro Met Ala Gln Gly Met Arg Ser Asp Phe Phe Leu
            340                 345                 350

Glu Gly Pro Phe Met Pro Arg Met Lys Met Asp Arg Asp Pro Leu
            355                 360                 365

Gly Gly Leu Ala Asp Met Phe Gly Gln Met Pro Gly Ser Gly Ile Gly
    370                 375                 380

Thr Gly Pro Gly Val Ile Gln Asp Arg Phe Ser Pro Thr Met Gly Arg
385                 390                 395                 400

His Arg Ser Asn Gln Leu Phe Asn Gly His Gly Gly His Ile Met Pro
                405                 410                 415

Pro Thr Gln Ser Gln Phe Gly Glu Met Gly Gly Lys Phe Met Lys Ser
            420                 425                 430

Gln Gly Leu Ser Gln Leu Tyr His Asn Gln Ser Gln Gly Leu Leu Ser
            435                 440                 445
```

-continued

```
Gln Leu Gln Gly Gln Ser Lys Asp Met Pro Pro Arg Phe Ser Lys Lys
    450                 455                 460
Gly Gln Leu Asn Ala Asp Glu Ile Ser Leu Arg Pro Ala Gln Ser Phe
465                 470                 475                 480
Leu Met Asn Lys Asn Gln Val Pro Lys Leu Gln Pro Gln Ile Thr Met
                485                 490                 495
Ile Pro Pro Ser Ala Gln Pro Pro Arg Thr Gln Thr Pro Pro Leu Gly
                500                 505                 510
Gln Thr Pro Gln Leu Gly Leu Lys Thr Asn Pro Pro Leu Ile Gln Glu
            515                 520                 525
Lys Pro Ala Lys Thr Ser Lys Lys Pro Pro Ser Lys Glu Glu Leu
    530                 535                 540
Leu Lys Leu Thr Glu Thr Val Val Thr Glu Tyr Leu Asn Ser Gly Asn
545                 550                 555                 560
Ala Asn Glu Ala Val Asn Gly Val Arg Glu Met Arg Ala Pro Lys His
                565                 570                 575
Phe Leu Pro Glu Met Leu Ser Lys Val Ile Ile Leu Ser Leu Asp Arg
                580                 585                 590
Ser Asp Glu Asp Lys Glu Lys Ala Ser Ser Leu Ile Ser Leu Leu Lys
            595                 600                 605
Gln Glu Gly Ile Ala Thr Ser Asp Asn Phe Met Gln Ala Phe Leu Asn
    610                 615                 620
Val Leu Asp Gln Cys Pro Lys Leu Glu Val Asp Ile Pro Leu Val Lys
625                 630                 635                 640
Ser Tyr Leu Ala Gln Phe Ala Ala Arg Ala Ile Ile Ser Glu Leu Val
                645                 650                 655
Ser Ile Ser Glu Leu Ala Gln Pro Leu Glu Ser Gly Thr His Phe Pro
            660                 665                 670
Leu Phe Leu Leu Cys Leu Gln Gln Leu Ala Lys Leu Gln Asp Arg Glu
    675                 680                 685
Trp Leu Thr Glu Leu Phe Gln Gln Ser Lys Val Asn Met Gln Lys Met
690                 695                 700
Leu Pro Glu Ile Asp Gln Asn Lys Asp Arg Met Leu Glu Ile Leu Glu
705                 710                 715                 720
Gly Lys Gly Leu Ser Phe Leu Phe Pro Leu Leu Lys Leu Glu Lys Glu
                725                 730                 735
Leu Leu Lys Gln Ile Lys Leu Asp Pro Ser Pro Gln Thr Ile Tyr Lys
            740                 745                 750
Trp Ile Lys Asp Asn Ile Ser Pro Lys Leu His Val Asp Lys Gly Phe
    755                 760                 765
Val Asn Ile Leu Met Thr Ser Phe Leu Gln Tyr Ile Ser Ser Glu Val
770                 775                 780
Asn Pro Pro Ser Asp Glu Thr Asp Ser Ser Ala Pro Ser Lys Glu
785                 790                 795                 800
Gln Leu Glu Gln Glu Lys Gln Leu Leu Ser Phe Lys Pro Val Met
                805                 810                 815
Gln Lys Phe Leu His Asp His Val Asp Leu Gln Val Ser Ala Leu Tyr
            820                 825                 830
Ala Leu Gln Val His Cys Tyr Asn Ser Asn Phe Pro Lys Gly Met Leu
    835                 840                 845
Leu Arg Phe Phe Val His Phe Tyr Asp Met Glu Ile Ile Glu Glu Glu
850                 855                 860
```

| Ala | Phe | Leu | Ala | Trp | Lys | Glu | Asp | Ile | Thr | Gln | Glu | Phe | Pro | Gly | Lys |
|-----|-----|-----|-----|-----|-----|-----|-----|-----|-----|-----|-----|-----|-----|-----|-----|
| 865 |     |     |     | 870 |     |     |     |     | 875 |     |     |     |     |     | 880 |

| Gly | Lys | Ala | Leu | Phe | Gln | Val | Asn | Gln | Trp | Leu | Thr | Trp | Leu | Glu | Thr |
|-----|-----|-----|-----|-----|-----|-----|-----|-----|-----|-----|-----|-----|-----|-----|-----|
|     |     |     |     | 885 |     |     |     | 890 |     |     |     |     |     | 895 |     |

| Ala | Glu | Glu | Glu | Glu | Ser | Glu | Glu | Glu | Ala | Asp |
|-----|-----|-----|-----|-----|-----|-----|-----|-----|-----|-----|
|     | 900 |     |     |     |     | 905 |     |     |     |     |

<210> SEQ ID NO 6
<211> LENGTH: 2724
<212> TYPE: DNA
<213> ORGANISM: Homo sapiens

<400> SEQUENCE: 6

```
gtggagagtg cgattgcaga aggggtgct tctcgtttca gtgcttcttc gggcggagga      60
ggaagtaggg gtgcacctca gcactatccc aagactgctg caacagcga gttcctgggg    120
aaaaccccag ggcaaaacgc tcagaaatgg attcctgcac gaagcactag acgagatgac    180
aactccgcag caaacaactc cgcaaacgaa aagaacgac atgatgcaat cttcaggaaa    240
gtaagaggca tactaaataa gcttactcct gaaaagtttg acaagctatg ccttgagctc    300
ctcaatgtgg gtgtagagtc taaactcatc cttaaagggg tcatactgct gattgtggac    360
aaagccctag aagagccaaa gtatagctca ctgtatgctc agctatgtct gcgattggca    420
gaagatgcac caaactttga tggcccagca gcagagggtc aaccaggaca gaagcaaagc    480
accacattca gacgcctcct aatttccaaa ttacaagatg aatttgaaaa ccgaactaga    540
aatgttgatg tctatgataa gcgtgaaaat cccctcctcc ccgaggagga ggaacagaga    600
gccattgcta agatcaagat gttgggaaac atcaaattca ttggagagct tggcaagctt    660
gatcttattc acgaatctat ccttcataag tgcatcaaaa cacttttgga aaagaagaag    720
agagtccaac tcaaagatat gggagaggat ttggagtgcc tctgtcagat aatgaggaca    780
gtgggaccta gattagacca tgaacgagcc aagtccttaa tggatcagta ctttgcccga    840
atgtgctcct tgatgttaag taaggaattg ccagcaagga ttcgtttcct gctgcaggat    900
accgtagagt tgcgagaaca ccattgggtt cctcgcaagg cttttcttga caatggacca    960
aagacgatca atcaaattcg tcaagatgca gtaaaagatc tagggtgtt tattcctgct   1020
cctatggctc aagggatgag aagtgacttc tttctggagg accgttcat gccacccagg   1080
atgaaaatgg atagggaccc acttggagga cttgctgata tgtttggaca aatgccaggt   1140
agcggaattg gtactggtcc aggagttatc caggatagat tttcacccac catgggacgt   1200
catcgttcaa atcaactctt caatggccat ggggacaca tcatgcctcc cacacaatcg   1260
cagtttggag agatgggagg caagtttatg aaaagccagg ggctaagcca gctctaccat   1320
aaccagagtc agggactctt atcccagctg caaggacagt cgaaggatat gccacctcgg   1380
ttttctaaga aaggacagct taatgcagat gagattagcc tgaggcctgc tcagtcgttc   1440
ctaatgaata aaaatcaagt gccaaagctt cagccccaga taactatgat tcctcctagt   1500
gcacaaccac cacgcactca acaccacct ctgggacaga cacctcagct tggtctcaaa   1560
actaatccac cacttatcca ggaaaagcct gccaagacca gcaaaaagcc accacgtca   1620
aaggaagaac tccttaaact aactgaaact gttgtgactg aatatctaaa tagtggaaat    1680
gcaaatgagg ctgtcaatgg tgtaagagaa atgggctc taaacactt tcttcctgag   1740
atgttaagca agtaatcat cctgtcacta gatagaagcg atgaagataa agaaaaagca   1800
agttctttga tcagtttact caaacaggaa gggatagcca caagtgacaa cttcatgcag   1860
```

-continued

```
gctttcctga atgtattgga ccagtgtccc aaactggagg ttgacatccc tttggtgaaa    1920
tcctatttag cacagtttgc agctcgtgcc atcatttcag agctggtgag catttcagaa    1980
ctagctcaac cactagaaag tggcacccat tttcctctct tcctactttg tcttcagcag    2040
ttagctaaat tacaagatcg agaatggtta acagaacttt ttcaacaaag caaggtcaat    2100
atgcagaaaa tgctcccaga aattgatcag aataaggacc gcatgttgga gattttggaa    2160
ggaaagggac tgagtttctt attcccactc ctcaaattgg agaaggaact gttgaagcaa    2220
ataaagttgg atccatcccc tcaaaccata tataaatgga ttaaagataa catctctccc    2280
aaacttcatg tagataaagg atttgtgaac atcttaatga ctagcttctt acagtacatt    2340
tctagtgaag taaccccccc cagcgatgaa acagattcat cctctgctcc ttccaaagaa    2400
cagttagagc aggaaaaaca actactacta tctttcaagc cagtaatgca gaaatttctt    2460
catgatcacg ttgatctaca agtcagtgcc ctgtatgctc tccaggtgca ctgctataac    2520
agcaacttcc caaaaggcat gttacttcgc ttttttgtgc acttctatga catggaaatt    2580
attgaagaag aagctttctt ggcttggaaa gaagatataa cccaagagtt tccgggaaaa    2640
ggcaaggctt tgttccaggt gaatcagtgg ctaacctggt tagaaactgc tgaagaagaa    2700
gaatcagagg aagaagctga ctaa                                          2724
```

<210> SEQ ID NO 7
<211> LENGTH: 445
<212> TYPE: PRT
<213> ORGANISM: Homo sapiens

<400> SEQUENCE: 7

```
Met Ala Ala Pro Glu Glu Arg Asp Leu Thr Gln Glu Gln Thr Glu Lys
1               5                   10                  15

Leu Leu Gln Phe Gln Asp Leu Thr Gly Ile Glu Ser Met Asp Gln Cys
            20                  25                  30

Arg His Thr Leu Glu Gln His Asn Trp Asn Ile Glu Ala Ala Val Gln
        35                  40                  45

Asp Arg Leu Asn Glu Gln Glu Gly Val Pro Ser Val Phe Asn Pro Pro
    50                  55                  60

Pro Ser Arg Pro Leu Gln Val Asn Thr Ala Asp His Arg Ile Tyr Ser
65                  70                  75                  80

Tyr Val Val Ser Arg Pro Gln Pro Arg Gly Leu Leu Gly Trp Gly Tyr
                85                  90                  95

Tyr Leu Ile Met Leu Pro Phe Arg Phe Thr Tyr Tyr Thr Ile Leu Asp
            100                 105                 110

Ile Phe Arg Phe Ala Leu Arg Phe Ile Arg Pro Asp Pro Arg Ser Arg
        115                 120                 125

Val Thr Asp Pro Val Gly Asp Ile Val Ser Phe Met His Ser Phe Glu
    130                 135                 140

Glu Lys Tyr Gly Arg Ala His Pro Val Phe Tyr Gln Gly Thr Tyr Ser
145                 150                 155                 160

Gln Ala Leu Asn Asp Ala Lys Arg Glu Leu Arg Phe Leu Leu Val Tyr
                165                 170                 175

Leu His Gly Asp Asp His Gln Asp Ser Asp Glu Phe Cys Arg Asn Thr
            180                 185                 190

Leu Cys Ala Pro Glu Val Ile Ser Leu Ile Asn Thr Arg Met Leu Phe
        195                 200                 205

Trp Ala Cys Ser Thr Asn Lys Pro Glu Gly Tyr Arg Val Ser Gln Ala
    210                 215                 220
```

```
Leu Arg Glu Asn Thr Tyr Pro Phe Leu Ala Met Ile Met Leu Lys Asp
225                 230                 235                 240
Arg Arg Met Thr Val Val Gly Arg Leu Glu Gly Leu Ile Gln Pro Asp
            245                 250                 255
Asp Leu Ile Asn Gln Leu Thr Phe Ile Met Asp Ala Asn Gln Thr Tyr
        260                 265                 270
Leu Val Ser Glu Arg Leu Glu Arg Glu Arg Asn Gln Thr Gln Val
    275                 280                 285
Leu Arg Gln Gln Gln Asp Glu Ala Tyr Leu Ala Ser Leu Arg Ala Asp
290                 295                 300
Gln Glu Lys Glu Arg Lys Arg Glu Arg Glu Arg Lys Arg Arg
305                 310                 315                 320
Lys Glu Glu Glu Val Gln Gln Gln Lys Leu Ala Glu Glu Arg Arg
                325                 330                 335
Gln Asn Leu Gln Glu Glu Lys Glu Arg Lys Leu Glu Cys Leu Pro Pro
            340                 345                 350
Glu Pro Ser Pro Asp Asp Pro Glu Ser Val Lys Ile Ile Phe Lys Leu
        355                 360                 365
Pro Asn Asp Ser Arg Val Glu Arg Arg Phe His Phe Ser Gln Ser Leu
    370                 375                 380
Thr Val Ile His Asp Phe Leu Phe Ser Leu Lys Glu Ser Pro Glu Lys
385                 390                 395                 400
Phe Gln Ile Glu Ala Asn Phe Pro Arg Arg Val Leu Pro Cys Ile Pro
                405                 410                 415
Ser Glu Glu Trp Pro Asn Pro Pro Thr Leu Gln Glu Ala Gly Leu Ser
            420                 425                 430
His Thr Glu Val Leu Phe Val Gln Asp Leu Thr Asp Glu
        435                 440                 445

<210> SEQ ID NO 8
<211> LENGTH: 1338
<212> TYPE: DNA
<213> ORGANISM: Homo sapiens

<400> SEQUENCE: 8
atggcggcgc ctgaggagcg ggatctaacc caggagcaga cagagaagct gctgcagttt      60
caggatctca ctggcatcga atctatggat cagtgtcgcc ataccttgga acagcataac     120
tggaacatag aggctgctgt acaggacaga ttgaatgagc aagagggcgt acctagtgtt     180
ttcaacccac ctccatcacg accctgcag gttaatacag ctgaccacag gatctacagc     240
tatgttgtct caagacctca accaaggggg ctgcttggat ggggttatta cttgataatg     300
cttccattcc ggtttaccta ttacacgata cttgatatat ttaggtttgc tcttcgtttt     360
atacggcctg accctcgcag ccgggtcact gaccccgttg ggacattgt ttcatttatg     420 cactcttttg aagagaaata tgggagggca caccctgtct ctaccaggg aacgtacagc     480 caggcactta cgatgccaa agggagctt cgctttcttt tggtttatct tcatggagat     540
gatcaccagg actctgatga gttttgtcgc aacacactct gtgcacctga agttatttca     600
ctaataaaca ctaggatgct cttctgggca tgctctacaa acaaacctga gggatacagg     660
gtctcacagg ctttacgaga gaacacctat ccattcctgg ccatgattat gctgaaggat     720
cgaaggatga ctgtggtggg acggctagaa ggcctcattc aacctgatga cctcattaac     780
caactgacat ttatcatgga tgctaaccag acttacctgg tgtcagaacg cctagaaagg     840
```

```
gaagaaagaa accagaccca agtgctgaga caacagcagg atgaggccta cctggcctct    900
ctcagagctg accaggagaa agaaagaaag aaacgggagg agcgggagcg taagcggcgg    960
aaggaggagg aggtgcaaca gcaaaagttg gcagaggaga gacggcggca gaatttacag   1020
gaggaaaagg aaaggaagtt ggaatgcctg ccccctgaac cttcccctga tgaccctgaa   1080
agtgtcaaga tcatcttcaa attacctaat gattctcgag tagagagacg attccacttt   1140
tcacagtctc taacagtaat ccacgacttc ttattctcct tgaaggaaag cccagaaaag   1200
tttcagattg aagccaattt tcccaggcga gtgctgccct gcatcccttc agaggagtgg   1260
cccaatcccc ctacgctaca ggaggccgga ctcagccaca cagaagttct ttttgttcag   1320
gacctaactg acgaatga                                                 1338
```

<210> SEQ ID NO 9
<211> LENGTH: 259
<212> TYPE: PRT
<213> ORGANISM: Homo sapiens

<400> SEQUENCE: 9

```
Met Lys Asp Val Asp Asn Leu Lys Ser Ile Lys Glu Glu Trp Val Cys
1               5                   10                  15
Glu Thr Gly Ser Asp Asn Gln Pro Leu Gly Asn Asn Gln Ser Asn
            20                  25                  30
Cys Glu Tyr Phe Val Asp Ser Leu Phe Glu Glu Ala Gln Lys Val Ser
        35                  40                  45
Ser Lys Cys Val Ser Pro Ala Glu Gln Lys Lys Gln Val Asp Val Asn
    50                  55                  60
Ile Lys Leu Trp Lys Asn Gly Phe Thr Val Asn Asp Asp Phe Arg Ser
65                  70                  75                  80
Tyr Ser Asp Gly Ala Ser Gln Gln Phe Leu Asn Ser Ile Lys Lys Gly
                85                  90                  95
Glu Leu Pro Ser Glu Leu Gln Gly Ile Phe Asp Lys Glu Glu Val Asp
            100                 105                 110
Val Lys Val Glu Asp Lys Lys Asn Glu Ile Cys Leu Ser Thr Lys Pro
        115                 120                 125
Val Phe Gln Pro Phe Ser Gly Gln Gly His Arg Leu Gly Ser Ala Thr
    130                 135                 140
Pro Lys Ile Val Ser Lys Ala Lys Asn Ile Glu Val Glu Asn Lys Asn
145                 150                 155                 160
Asn Leu Ser Ala Val Pro Leu Asn Asn Leu Glu Pro Ile Thr Asn Ile
                165                 170                 175
Gln Ile Trp Leu Ala Asn Gly Lys Arg Ile Val Gln Lys Phe Asn Ile
            180                 185                 190
Thr His Arg Val Ser His Ile Lys Asp Phe Ile Glu Lys Tyr Gln Gly
        195                 200                 205
Ser Gln Arg Ser Pro Pro Phe Ser Leu Ala Thr Ala Leu Pro Val Leu
    210                 215                 220
Arg Leu Leu Asp Glu Thr Leu Thr Leu Glu Glu Ala Asp Leu Gln Asn
225                 230                 235                 240
Ala Val Ile Ile Gln Arg Leu Gln Lys Thr Ala Ser Phe Arg Glu Leu
                245                 250                 255
Ser Glu His
```

<210> SEQ ID NO 10
<211> LENGTH: 780

<212> TYPE: DNA
<213> ORGANISM: Homo sapiens

<400> SEQUENCE: 10

```
atgaaagacg tagataacct caaaagtata aagaagaat gggtttgtga aacaggatct      60
gataatcaac ctcttggtaa taatcaacaa tcaaattgtg aatattttgt tgatagcctt    120
tttgaggaag ctcagaaggt tagttccaaa tgtgtgtctc ccgctgaaca gaagaaacag    180
gtagatgtaa atataaaatt atggaaaaac ggattcaccg tcaacgacga tttcagaagt    240
tattccgatg gtgccagtca gcagttttg aactccatca aaaggggga attaccttca     300
gaattacagg gaattttga taagaagag gtggacgtta aagttgaaga caagaaaaat     360
gaaatatgtt tgtctacgaa gcctgtgttc cagccctttt caggacaggg tcacagacta    420
ggaagtgcca caccaaaaat tgtttctaaa gcaaagaata ttgaagttga aaataaaaat    480
aatttgtctg ctgttccact gaacaacttg gaacccatta ctaatataca gatctggttg    540
gccaatggaa aaggattgt ccagaaattt aacattactc atagagtaag ccatatcaaa    600
gacttcattg aaaaatacca aggatctcaa agaagtcctc cgttttccct ggcaacagct    660
cttcctgtcc tcaggttgct agatgagaca ctcacactgg aagaagcaga tttacagaat    720
gctgtcatca ttcagagact ccaaaaaact gcatctttta gagaactttc agagcactga    780
```

<210> SEQ ID NO 11
<211> LENGTH: 520
<212> TYPE: PRT
<213> ORGANISM: Homo sapiens

<400> SEQUENCE: 11

```
Met Ser Ser Pro Leu Ala Ser Leu Ser Lys Thr Arg Lys Val Pro Leu
1               5                   10                  15

Pro Ser Glu Pro Met Asn Pro Gly Arg Arg Gly Ile Arg Ile Tyr Gly
            20                  25                  30

Asp Glu Asp Glu Val Asp Met Leu Ser Asp Gly Cys Gly Ser Glu Glu
        35                  40                  45

Lys Ile Ser Val Pro Ser Cys Tyr Gly Gly Ile Gly Ala Pro Val Ser
    50                  55                  60

Arg Gln Val Pro Ala Ser His Asp Ser Glu Leu Met Ala Phe Met Thr
65                  70                  75                  80

Arg Lys Leu Trp Asp Leu Glu Gln Gln Val Lys Ala Gln Thr Asp Glu
                85                  90                  95

Ile Leu Ser Lys Asp Gln Lys Ile Ala Ala Leu Glu Asp Leu Val Gln
            100                 105                 110

Thr Leu Arg Pro His Pro Ala Glu Ala Thr Leu Gln Arg Gln Glu Glu
        115                 120                 125

Leu Glu Thr Met Cys Val Gln Leu Gln Arg Gln Val Arg Glu Met Glu
    130                 135                 140

Arg Phe Leu Ser Asp Tyr Gly Leu Gln Trp Val Gly Glu Pro Met Asp
145                 150                 155                 160

Gln Glu Asp Ser Glu Ser Lys Thr Val Ser Glu His Gly Glu Arg Asp
                165                 170                 175

Trp Met Thr Ala Lys Lys Phe Trp Lys Pro Gly Asp Ser Leu Ala Pro
            180                 185                 190

Pro Glu Val Asp Phe Asp Arg Leu Leu Ala Ser Leu Gln Asp Leu Ser
        195                 200                 205
```

```
Glu Leu Val Glu Gly Asp Thr Gln Val Thr Pro Val Pro Gly Gly
    210                 215                 220

Ala Arg Leu Arg Thr Leu Glu Pro Ile Pro Leu Lys Leu Tyr Arg Asn
225                 230                 235                 240

Gly Ile Met Met Phe Asp Gly Pro Phe Gln Pro Phe Tyr Asp Pro Ser
                245                 250                 255

Thr Gln Arg Cys Leu Arg Asp Ile Leu Asp Gly Phe Phe Pro Ser Glu
            260                 265                 270

Leu Gln Arg Leu Tyr Pro Asn Gly Val Pro Phe Lys Val Ser Asp Leu
        275                 280                 285

Arg Asn Gln Val Tyr Leu Glu Asp Gly Leu Asp Pro Phe Pro Gly Glu
    290                 295                 300

Gly Arg Val Val Gly Arg Gln Leu Met His Lys Ala Leu Asp Arg Val
305                 310                 315                 320

Glu Glu His Pro Gly Ser Arg Met Thr Ala Glu Lys Phe Leu Asn Arg
                325                 330                 335

Leu Pro Lys Phe Val Ile Arg Gln Gly Glu Val Ile Asp Ile Arg Gly
            340                 345                 350

Pro Ile Arg Asp Thr Leu Gln Asn Cys Cys Pro Leu Pro Ala Arg Ile
        355                 360                 365

Gln Glu Ile Val Val Glu Thr Pro Thr Leu Ala Ala Glu Arg Glu Arg
    370                 375                 380

Ser Gln Glu Ser Pro Asn Thr Pro Ala Pro Pro Leu Ser Met Leu Arg
385                 390                 395                 400

Ile Lys Ser Glu Asn Gly Glu Gln Ala Phe Leu Leu Met Met Gln Pro
                405                 410                 415

Asp Asn Thr Ile Gly Asp Val Arg Ala Leu Leu Ala Gln Ala Arg Val
            420                 425                 430

Met Asp Ala Ser Ala Phe Glu Ile Phe Ser Thr Phe Pro Pro Thr Leu
        435                 440                 445

Tyr Gln Asp Asp Thr Leu Thr Leu Gln Ala Ala Gly Leu Val Pro Lys
    450                 455                 460

Ala Ala Leu Leu Leu Arg Ala Arg Arg Ala Pro Lys Ser Ser Leu Lys
465                 470                 475                 480

Phe Ser Pro Gly Pro Cys Pro Gly Pro Gly Pro Ser Pro Gly
                485                 490                 495

Pro Gly Pro Gly Pro Ser Pro Gly Pro Gly Pro Ser Pro Cys
            500                 505                 510

Pro Gly Pro Ser Pro Ser Pro Gln
        515                 520

<210> SEQ ID NO 12
<211> LENGTH: 1563
<212> TYPE: DNA
<213> ORGANISM: Homo sapiens

<400> SEQUENCE: 12
atgagctcac ctttggcctc ccttagcaag acccgaaaag tgccccctgcc ctcggagcct      60 atgaatcctg ggaggcgagg aatccgcatc tatggagatg aagatgaggt ggacatgttg     120
agtgatgggt gtggctcaga agaaaagatc tcagtcccct cctgctatgg cggcataggt     180
gcccctgtga gtcggcaagt ccctgcatcc catgactcgg agctgatggc cttcatgacg     240
aggaagttgt gggacctgga gcagcaggta aaggcccaga ctgatgagat actgtccaag     300
gatcagaaga tagcggccct agaggacctg gtgcagaccc tccggccaca cccagccgag     360
```

```
gcaaccctgc agcggcagga ggaactggag acgatgtgtg tgcagctgca gcggcaggtc    420
agggagatgg agcggttcct cagtgactat ggcctgcagt gggtgggcga gcccatggac    480
caggaggact cagagagcaa gacagtctca gagcatggcg agagggactg gatgacagcc    540
aagaagttct ggaagccagg ggactcattg gcgccccctg aggtggactt tgacaggctg    600
ctggccagcc tgcaggatct tagtgagctg gtggtagagg gtgacaccca agtgacacca    660
gtgcccggcg gggcacggct gcgtaccctc gagcccatcc cgctgaagct ctaccggaat    720
ggcatcatga tgttcgacgg gcccttccag cccttctacg atccctccac acagcgctgc    780
ctccgagaca tattggatgg cttctttccc tcagagctcc agcgactgta ccccaatggg    840
gtccccttta aggtgagtga cttgcgcaat caggtctacc tggaggatgg actggacccc    900
ttcccaggcg agggccgtgt ggtgggcagg cagctgatgc acaaggcctt ggacagggtg    960
gaggagcacc caggctccag gatgactgct gagaaatttc tgaacaggct ccccaagttt   1020
gtgatccggc aaggcgaggt gattgacatc cggggcccca tcaggacac cttgcagaac   1080
tgctgcccat gcctgcccg gatccaggag attgtggtgg agacgcccac cttggccgct   1140
gagcgagaga ggagccagga gtcacccaac acgccggcac ccccgctctc catgctgcgc   1200
atcaagtctg agaatgggga acaggccttc ctactgatga tgcagcctga caacaccatt   1260
ggggacgtgc gagctctgct agcgcaggcc agggtcatgg atgcctctgc ctttgagatc   1320
ttcagcacat tcccgcccac cctctaccag gacgatacac tcacgctgca ggctgcaggc   1380
cttgtgccca aagcagcact gctgctgcgg gcacgccgag ccccgaagtc cagcctgaaa   1440
ttcagtcctg gtccctgtcc cggtcccggt cccggcccca gtcccggtcc cggtcccggc   1500
cccagtcccg gtcccggtcc cggccccagt ccctgtcctg acccagtccc agcccccaa   1560
taa                                                                  1563
```

<210> SEQ ID NO 13
<211> LENGTH: 441
<212> TYPE: PRT
<213> ORGANISM: Homo sapiens

<400> SEQUENCE: 13

```
Met Lys Lys Phe Phe Gln Glu Phe Lys Ala Asp Ile Lys Phe Lys Ser
1               5                   10                  15

Ala Gly Pro Gly Gln Lys Leu Lys Glu Ser Val Gly Glu Lys Ala His
            20                  25                  30

Lys Glu Lys Pro Asn Gln Pro Ala Pro Arg Pro Arg Gln Gly Pro
        35                  40                  45

Thr Asn Glu Ala Gln Met Ala Ala Ala Ala Leu Ala Arg Leu Glu
    50                  55                  60

Gln Lys Gln Ser Arg Ala Trp Gly Pro Thr Ser Gln Asp Thr Ile Arg
65                  70                  75                  80

Asn Gln Val Arg Lys Glu Leu Gln Ala Glu Ala Thr Val Ser Gly Ser
                85                  90                  95

Pro Glu Ala Pro Gly Thr Asn Val Val Ser Glu Pro Arg Glu Glu Gly
            100                 105                 110

Ser Ala His Leu Ala Val Pro Gly Val Tyr Phe Thr Cys Pro Leu Thr
        115                 120                 125

Gly Ala Thr Leu Arg Lys Asp Gln Arg Asp Ala Cys Ile Lys Glu Ala
    130                 135                 140
```

Ile Leu Leu His Phe Ser Thr Asp Pro Val Ala Ala Ser Ile Met Lys
145                 150                 155                 160

Ile Tyr Thr Phe Asn Lys Asp Gln Asp Arg Val Lys Leu Gly Val Asp
            165                 170                 175

Thr Ile Ala Lys Tyr Leu Asp Asn Ile His Leu His Pro Glu Glu Glu
        180                 185                 190

Lys Tyr Arg Lys Ile Lys Leu Gln Asn Lys Val Phe Gln Glu Arg Ile
        195                 200                 205

Asn Cys Leu Glu Gly Thr His Glu Phe Phe Glu Ala Ile Gly Phe Gln
210                 215                 220

Lys Val Leu Leu Pro Ala Gln Asp Gln Glu Asp Pro Glu Glu Phe Tyr
225                 230                 235                 240

Val Leu Ser Glu Thr Thr Leu Ala Gln Pro Gln Ser Leu Glu Arg His
                245                 250                 255

Lys Glu Gln Leu Leu Ala Ala Glu Pro Val Arg Ala Lys Leu Asp Arg
                260                 265                 270

Gln Arg Arg Val Phe Gln Pro Ser Pro Leu Ala Ser Gln Phe Glu Leu
            275                 280                 285

Pro Gly Asp Phe Phe Asn Leu Thr Ala Glu Glu Ile Lys Arg Glu Gln
290                 295                 300

Arg Leu Arg Ser Glu Ala Val Glu Arg Leu Ser Val Leu Arg Thr Lys
305                 310                 315                 320

Ala Met Arg Glu Lys Glu Gln Arg Gly Leu Arg Lys Tyr Asn Tyr
                325                 330                 335

Thr Leu Leu Arg Val Arg Leu Pro Asp Gly Cys Leu Leu Gln Gly Thr
            340                 345                 350

Phe Tyr Ala Arg Glu Arg Leu Gly Ala Val Tyr Gly Phe Val Arg Glu
            355                 360                 365

Ala Leu Gln Ser Asp Trp Leu Pro Phe Glu Leu Leu Ala Ser Gly Gly
        370                 375                 380

Gln Lys Leu Ser Glu Asp Glu Asn Leu Ala Leu Asn Glu Cys Gly Leu
385                 390                 395                 400

Val Pro Ser Ala Leu Leu Thr Phe Ser Trp Asp Met Ala Val Leu Glu
                405                 410                 415

Asp Ile Lys Ala Ala Gly Ala Glu Pro Asp Ser Ile Leu Lys Pro Glu
                420                 425                 430

Leu Leu Ser Ala Ile Glu Lys Leu Leu
            435                 440

<210> SEQ ID NO 14
<211> LENGTH: 1326
<212> TYPE: DNA
<213> ORGANISM: Homo sapiens

<400> SEQUENCE: 14
atgaagaaat ctttcagga gttcaaggcc gacatcaagt tcaagagcgc gggacccggt    60
cagaagctca aagagtccgt gggggaaaag gcccacaaag agaagcccaa ccagccagcc   120
cccaggccgc cccgccaggg acccaccaat gaggcacaga tggcagccgc tgctgcccta   180
gcccggctgg agcagaagca gtcccgggcc tggggcccca tcgcagga caccatccga    240 aaccaggtga gaaggaact tcaagccgaa gccaccgtca gcgggagccc cgaggcccca   300
gggaccaacg tggtatctga gcccagagag aaggctctg cccacctggc tgtgcctggc   360
gtgtacttca cctgtccgct cactggggcc accctgagga aggaccagcg ggacgcctgc   420

```
atcaaggagg ccattctctt gcacttctcc accgacccag tggccgcctc catcatgaag    480
atctacacgt tcaacaaaga ccaggaccgg gtgaagctgg gtgtggacac cattgccaag    540
tacctggaca acatccacct gcaccccgag gaggagaagt accggaagat caagctgcag    600
aacaaggtgt tcaggagcg cattaactgc ctggaaggga cccacgagtt ttttgaggcc     660
attgggttcc agaaggtgtt gcttcccgcc caggatcagg aggaccccga ggagttctac    720
gtgctgagcg agaccacctt ggcccagccc cagagcctgg agaggcacaa gaacagctg    780 ctggctgcgg agcccgtgcg cgccaagctg gacaggcagc gccgcgtctt ccagccctcg    840
cccctggcct cgcagttcga actgcctggg gacttcttca acctcacagc agaggagatc    900
aagcgggagc agaggctcag gtccgaggcg gtggagcggc tgagcgtgct gcggaccaag    960
gccatgcggg agaaggagga gcagcggggg ctgcgcaagt acaactacac gctgctgcgc   1020
gtgcgcctcc ccgatggctg cctcctgcag gcactttct acgctcggga cggctgggg    1080 gcggtgtacg ggttcgtccg ggaggccctg cagagcgact ggctgccttt tgagctgctg   1140
gcctcgggag ggcagaagct gtccgaggac gagaacctgg ccttgaacga gtgcgggctg   1200
gtgccctctg ccctcctgac cttctcgtgg gacatggctg tgctggagga catcaaggcc   1260
gcgggggccg agccggactc catcctgaaa cccgagctcc tgtcagccat cgagaagctc   1320
ttgtga                                                              1326
```

<210> SEQ ID NO 15  
<211> LENGTH: 508  
<212> TYPE: PRT  
<213> ORGANISM: Homo sapiens

<400> SEQUENCE: 15

```
Met Leu Trp Phe Gln Gly Ala Ile Pro Ala Ala Ile Ala Thr Ala Lys
1               5                   10                  15

Arg Ser Gly Ala Val Phe Val Val Phe Val Ala Gly Asp Asp Glu Gln
            20                  25                  30

Ser Thr Gln Met Ala Ala Ser Trp Glu Asp Asp Lys Val Thr Glu Ala
        35                  40                  45

Ser Ser Asn Ser Phe Val Ala Ile Lys Ile Asp Thr Lys Ser Glu Ala
    50                  55                  60

Cys Leu Gln Phe Ser Gln Ile Tyr Pro Val Val Cys Val Pro Ser Ser
65                  70                  75                  80

Phe Phe Ile Gly Asp Ser Gly Ile Pro Leu Glu Val Ile Ala Gly Ser
                85                  90                  95

Val Ser Ala Asp Glu Leu Val Thr Arg Ile His Lys Val Arg Gln Met
            100                 105                 110

His Leu Leu Lys Ser Glu Thr Ser Val Ala Asn Gly Ser Gln Ser Glu
        115                 120                 125

Ser Ser Val Ser Thr Pro Ser Ala Ser Phe Glu Pro Asn Asn Thr Cys
    130                 135                 140

Glu Asn Ser Gln Ser Arg Asn Ala Glu Leu Cys Glu Ile Pro Pro Thr
145                 150                 155                 160

Ser Asp Thr Lys Ser Asp Thr Ala Thr Gly Gly Glu Ser Ala Gly His
                165                 170                 175

Ala Thr Ser Ser Gln Glu Pro Ser Gly Cys Ser Asp Gln Arg Pro Ala
            180                 185                 190

Glu Asp Leu Asn Ile Arg Val Glu Arg Leu Thr Lys Lys Leu Glu Glu
        195                 200                 205
```

```
Arg Arg Glu Glu Lys Arg Lys Glu Glu Glu Gln Arg Glu Ile Lys Lys
    210                 215                 220
Glu Ile Glu Arg Arg Lys Thr Gly Lys Glu Met Leu Asp Tyr Lys Arg
225                 230                 235                 240
Lys Gln Glu Glu Leu Thr Lys Arg Met Leu Glu Gly Arg Asn Arg
                245                 250                 255
Glu Lys Ala Glu Asp Arg Ala Ala Arg Glu Arg Ile Lys Gln Gln Ile
            260                 265                 270
Ala Leu Asp Arg Ala Glu Arg Ala Ala Arg Phe Ala Lys Thr Lys Glu
                275                 280                 285
Glu Val Glu Ala Ala Lys Ala Ala Leu Leu Ala Lys Gln Ala Glu
290                 295                 300
Met Glu Val Lys Arg Glu Ser Tyr Ala Arg Glu Arg Ser Thr Val Ala
305                 310                 315                 320
Arg Ile Gln Phe Arg Leu Pro Asp Gly Ser Ser Phe Thr Asn Gln Phe
                325                 330                 335
Pro Ser Asp Ala Pro Leu Glu Glu Ala Arg Gln Phe Ala Ala Gln Thr
                340                 345                 350
Val Gly Asn Thr Tyr Gly Asn Phe Ser Leu Ala Thr Met Phe Pro Arg
                355                 360                 365
Arg Glu Phe Thr Lys Glu Asp Tyr Lys Lys Lys Leu Leu Asp Leu Glu
            370                 375                 380
Leu Ala Pro Ser Ala Ser Val Val Leu Leu Pro Ala Gly Arg Pro Thr
385                 390                 395                 400
Ala Ser Ile Val His Ser Ser Ser Gly Asp Ile Trp Thr Leu Leu Gly
                405                 410                 415
Thr Val Leu Tyr Pro Phe Leu Ala Ile Trp Arg Leu Ile Ser Asn Phe
                420                 425                 430
Leu Phe Ser Asn Pro Pro Thr Gln Thr Ser Val Arg Val Thr Ser
            435                 440                 445
Ser Glu Pro Pro Asn Pro Ala Ser Ser Ser Lys Ser Glu Lys Arg Glu
            450                 455                 460
Pro Val Arg Lys Arg Val Leu Glu Lys Arg Gly Asp Asp Phe Lys Lys
465                 470                 475                 480
Glu Gly Lys Ile Tyr Arg Leu Arg Thr Gln Asp Asp Gly Glu Asp Glu
                485                 490                 495
Asn Asn Thr Trp Asn Gly Asn Ser Thr Gln Gln Met
                500                 505

<210> SEQ ID NO 16
<211> LENGTH: 1527
<212> TYPE: DNA
<213> ORGANISM: Homo sapiens

<400> SEQUENCE: 16
atgctgtggt tccagggcgc cattccggcc gccatcgcga cggccaaaag gagcggcgcg      60
gtcttcgtgg tgttcgtggc aggtgatgat gaacagtcta cacagatggc tgcaagttgg     120
gaagatgata agttacagaa agcatcttca aacagttttg ttgctattaa atcgataca      180 aaaagtgaag cctgcctaca gttttcacaa atctatcctg tagtgtgtgt tccatccagt     240
ttctttattg gagacagtgg aattcccttg gaagtaatag caggaagtgt ttctgcagat     300
gaacttgtta caagaattca caggtccga cagatgcatt tgctaaaaag tgaaacatca     360
gtagcaaatg gcagtcagtc agaaagttca gtgtctactc catctgcgtc atttgaacct     420
```

-continued

```
aacaacactt gtgaaaactc tcagtccaga aatgcagagc tttgtgagat accacccact    480
tctgatacaa agtcagatac tgcaacagga ggagaaagtg caggccatgc cacttcctct    540
caggagccta gtggatgctc agatcagaga cctgcagagg acctcaacat ccgagtggaa    600
agactaacaa aaaacttga agaaggaga gaagagaaaa gaaagagga agaacagaga       660 gaaattaaga aggaaattga gaggagaaaa actggaaaag aaatgttgga ttataaaaga    720
aaacaagaag aagaattaac aaaaagaatg ctggaggaaa gaaacagaga aaagcagaa     780 gatagggcag ctcgagaacg tataaaacag cagattgcat tggaccgtgc agagagagct    840
gctcgttttg caaagacaaa ggaagaagta gaggctgcca agctgctgc cttgctagca     900 aaacaggcag aaatggaagt caagagggaa tcttatgcaa gagaaagaag cactgttgca    960
agaattcaat tccgtcttcc tgatggttct tcctttacaa atcagttccc ttctgatgct   1020
cctctagaag aggcaaggca gtttgctgca cagactgttg gcaacactta cggtaatttt   1080
tcgttagcaa ccatgtttcc caggagggaa tttaccaaag aagattataa aaagaagtta   1140
ctggatttgg aacttgcccc aagcgcttcg gtggtactgt tgccagcagg aagaccaact   1200
gcatccattg tacactcttc cagcggagac atttggacct tgttgggaac agtgctttat   1260
ccattccttg ccatctggag attaattagc aatttcttgt ttagtaatcc gcctcccaca   1320
cagacttcag tgagagtaac atcgtcagaa cccccaaacc ctgcatcatc tagcaaatca   1380
gaaaaaaggg aaccagtgag aaaaagagtg ctggaaaaac gtggagacga ctttaaaaag   1440 gagggggaaaa tttatagatt aaggactcaa gatgatggtg aagatgaaaa caacacttgg   1500
aatggaaatt ccactcaaca gatgtag                                       1527
```

<210> SEQ ID NO 17
<211> LENGTH: 280
<212> TYPE: PRT
<213> ORGANISM: Homo sapiens

<400> SEQUENCE: 17

```
Met Ala Thr Glu Ala Pro Val Asn Ile Ala Pro Glu Cys Ser Thr
1               5                  10                  15

Val Val Ser Thr Ala Val Asp Ser Leu Ile Trp Gln Pro Asn Ser Leu
            20                  25                  30

Asn Met His Met Ile Arg Pro Lys Ser Ala Lys Gly Arg Thr Arg Pro
        35                  40                  45

Ser Leu Gln Lys Ser Gln Gly Val Glu Val Cys Ala His His Ile Pro
    50                  55                  60

Ser Pro Pro Ala Ile Pro Tyr Glu Leu Pro Ser Ser Gln Lys Pro
65                  70                  75                  80

Gly Ala Cys Ala Pro Lys Ser Pro Asn Gln Gly Ala Ser Asp Glu Ile
                85                  90                  95

Pro Glu Leu Gln Gln Gln Val Pro Thr Gly Ala Ser Ser Ser Leu Asn
            100                 105                 110

Lys Tyr Pro Val Leu Pro Ser Ile Asn Arg Lys Asn Leu Glu Glu Glu
        115                 120                 125

Ala Val Glu Thr Val Ala Lys Lys Ala Ser Ser Leu Gln Leu Ser Ser
    130                 135                 140

Ile Arg Ala Leu Tyr Gln Asp Glu Thr Gly Thr Met Lys Thr Ser Glu
145                 150                 155                 160

Glu Asp Ser Arg Ala Arg Ala Cys Ala Val Glu Arg Lys Phe Ile Val
                165                 170                 175
```

Arg Thr Lys Lys Gln Gly Ser Ser Arg Ala Gly Asn Leu Glu Glu Pro
            180                 185                 190

Ser Asp Gln Glu Pro Arg Leu Leu Leu Ala Val Arg Ser Pro Thr Gly
            195                 200                 205

Gln Arg Phe Val Arg His Phe Arg Pro Thr Asp Leu Gln Thr Ile
    210                 215                 220

Val Ala Val Ala Glu Gln Lys Asn Lys Thr Ser Tyr Arg His Cys Ser
225                 230                 235                 240

Ile Glu Thr Met Glu Val Pro Arg Arg Phe Ser Asp Leu Thr Lys
                245                 250                 255

Ser Leu Gln Glu Cys Arg Ile Pro His Lys Ser Val Leu Gly Ile Ser
            260                 265                 270

Leu Glu Asp Gly Glu Gly Trp Pro
            275                 280

<210> SEQ ID NO 18
<211> LENGTH: 843
<212> TYPE: DNA
<213> ORGANISM: Homo sapiens

<400> SEQUENCE: 18
atggccacag aagcccctgt gaatatagca ccacctgagt gtagcactgt tgtcagcaca      60
gcagttgaca gcctcatttg gcagccaaac tcactaaata tgcacatgat aaggcccaag     120
tccgccaagg gacggacaag accgagtctg cagaaatccc agggcgtgga ggtgtgcgct     180
catcatatac catctccgcc tccagccatt ccctatgagt tgccaagcag ccaaaaacca     240
ggagcctgtg cacccaaatc tccaaaccag ggagcttctg atgagatccc tgagctgcag     300
cagcaagtac ccactggggc ttcctcttct ctcaataagt atccagtcct tccttccatc     360
aacagaaaga acctggagga ggaggctgtg gaaaccgttg ccaaaaaggc cagctcactg     420
caactgagca gtatccgggc tctttaccaa gacgagacgg gcaccatgaa acaagtgaa     480
gaagattcca gagctcgagc ttgtgccgtg gagaggaaat tcatcgtccg aaccaagaaa     540
cagggctctt ccaggctgg aaatctggag gaaccatcgg accaagaacc aaggttgctg     600
cttgctgtta gatcaccaac aggccaaagg tttgtacgcc atttccggcc aacagatgat     660
ttgcaaacca tgttgctgt ggccgaacag aaaaacaaaa cctcctaccg acactgcagc     720
attgaaacaa tggaggtgcc aggaggcga ttttctgacc tcaccaaatc tctgcaagag     780
tgcagaatcc cccacaagtc tgtgctgggc atctcactgg aagatgggga agggtggccc     840
tga                                                                   843

<210> SEQ ID NO 19
<211> LENGTH: 270
<212> TYPE: PRT
<213> ORGANISM: Homo sapiens

<400> SEQUENCE: 19

Met Ala Ser Arg Gly Val Val Gly Ile Phe Phe Leu Ser Ala Val Pro
1               5                   10                  15

Leu Val Cys Leu Glu Leu Arg Arg Gly Ile Pro Asp Ile Gly Ile Lys
            20                  25                  30

Asp Phe Leu Leu Leu Cys Gly Arg Ile Leu Leu Leu Ala Leu Leu
        35                  40                  45

Thr Leu Ile Ile Ser Val Thr Thr Ser Trp Leu Asn Ser Phe Lys Ser
    50                  55                  60

```
Pro Gln Val Tyr Leu Lys Glu Glu Glu Lys Asn Glu Lys Arg Gln
 65                  70                  75                  80

Lys Leu Val Arg Lys Gln Gln Glu Ala Gln Gly Glu Lys Ala Ser
             85                  90                  95

Arg Tyr Ile Glu Asn Val Leu Lys Pro His Gln Glu Met Lys Leu Arg
            100                 105                 110

Lys Leu Glu Glu Arg Phe Tyr Gln Met Thr Gly Glu Ala Trp Lys Leu
        115                 120                 125

Ser Ser Gly His Lys Leu Gly Gly Asp Glu Gly Thr Ser Gln Thr Ser
    130                 135                 140

Phe Glu Thr Ser Asn Arg Glu Ala Ala Lys Ser Gln Asn Leu Pro Lys
145                 150                 155                 160

Pro Leu Thr Glu Phe Pro Ser Pro Ala Glu Gln Pro Thr Cys Lys Glu
                165                 170                 175

Ile Pro Asp Leu Pro Glu Glu Pro Ser Gln Thr Ala Glu Val Val
            180                 185                 190

Thr Val Ala Leu Arg Cys Pro Ser Gly Asn Val Leu Arg Arg Phe
            195                 200                 205

Leu Lys Ser Tyr Ser Ser Gln Val Leu Phe Asp Trp Met Thr Arg Ile
    210                 215                 220

Gly Tyr His Ile Ser Leu Tyr Ser Leu Ser Thr Ser Phe Pro Arg Arg
225                 230                 235                 240

Pro Leu Ala Val Glu Gly Gly Gln Ser Leu Glu Asp Ile Gly Ile Thr
                245                 250                 255

Val Asp Thr Val Leu Ile Leu Glu Glu Lys Glu Gln Thr Asn
                260                 265                 270

<210> SEQ ID NO 20
<211> LENGTH: 1442
<212> TYPE: DNA
<213> ORGANISM: Homo sapiens

<400> SEQUENCE: 20
caggcgcttc cgccaccatg gcttcacgtg gggttgttgg catttttcttc ctctctgctg      60 tcccccttgt gtgtctggag ctccggcgtg ggatcccgga tataggaatc aaggattttc     120
ttttgctttg tggccggatt ttgctactgc ttgctcttct tactttaatt atttctgtga     180
ctacctcatg gcttaactca tttaaatctc cccaagttta tctgaaggaa gaagaagaaa     240
agaatgagaa aagacaaaaa cttgtgagaa aaaacaaca agaagcacaa ggagagaagg      300
ccagcagata catagagaat gttttaaaac ctcaccagga aatgaaattg agaaaactgg     360
aggagcgctt ttatcaaatg acgggtgaag cctggaaatt aagcagtggt cacaaacttg     420
ggggtgatga aggtacaagt cagacatctt ttgaaacatc aaacagagaa gcagcaaaga     480
gccagaactt gcctaaacct ttaactgaat tccgtctcc tgctgaacag cccacatgca     540
aggagattcc tgatttacct gaagaaccct ctcaaacagc agaagaagta gttactgttg     600
ctctccgatg tcccagtggg aatgtcctga ggagaaggtt tttgaagtcc tacagctcac     660
aggtcttatt tgactggatg acgagaattg ggtaccacat atctctatac agcctttcta     720
cttcctttcc cagacggcct ctggcagtgg agggaggcca gtcgctgag gacataggaa      780 taactgtgga cactgtactc atcctggagg agaaggagca gaccaactag gaaagaaggg     840
agagctccct gtttgcatga agtcagttat gctatgacct tctggcacaa taaaggcttc     900
actttcaaat cacactatac cttgattgag ctcatggcag taaactttga acattgatat     960
```

-continued

```
ccatgggaat aggattagaa aaggattgct ttctatatat aataatctgt ggactgtgcc    1020
attttacagt gtaccaaatg agaatgaggt tgaaatgtat gcagtaaggt actcagtaat    1080
taattggtat tttttcccag ctgacatgat ttctcagtgt tagaaaacaa acccttagaa    1140
ctttcctttc tgcctcttca atccatctta ccacacaata tttcatgatt caaattcttc    1200
aaagtcttat acgcaggaat gtttattctg ctgtatttct gtgaaattaa aaacttggaa    1260
gaagcttcaa agctcttgga ggctttaaag ttctttctgt tgggtgtgca ttacagttta    1320
cttaactgat gtttgcgatt tatataattt tgccttgtat taaatgttac aaagttccaa    1380
atgaatcagt atttaaaaa ataaaactat gaaagcatta aatataggt gaatttttaa     1440 aa                                                                   1442
```

<210> SEQ ID NO 21
<211> LENGTH: 608
<212> TYPE: PRT
<213> ORGANISM: Homo sapiens

<400> SEQUENCE: 21

```
Met Ala Glu Ser Ile Ile Ile Arg Val Gln Ser Pro Asp Gly Val Lys
1               5                   10                  15

Arg Ile Thr Ala Thr Lys Arg Glu Thr Ala Ala Thr Phe Leu Lys Lys
            20                  25                  30

Val Ala Lys Glu Phe Gly Phe Gln Asn Asn Gly Phe Ser Val Tyr Ile
        35                  40                  45

Asn Arg Asn Lys Thr Gly Glu Ile Thr Ala Ser Asn Lys Ser Leu
    50                  55                  60

Asn Leu Leu Lys Ile Lys His Gly Asp Leu Leu Phe Leu Phe Pro Ser
65                  70                  75                  80

Ser Leu Ala Gly Pro Ser Ser Glu Met Glu Thr Ser Val Pro Pro Gly
                85                  90                  95

Phe Lys Val Phe Gly Ala Pro Asn Val Val Asp Glu Ile Asp Gln
            100                 105                 110

Tyr Leu Ser Lys Gln Asp Gly Lys Ile Tyr Arg Ser Arg Asp Pro Gln
        115                 120                 125

Leu Cys Arg His Gly Pro Leu Gly Lys Cys Val His Cys Val Pro Leu
    130                 135                 140

Glu Pro Phe Asp Glu Asp Tyr Leu Asn His Leu Glu Pro Pro Val Lys
145                 150                 155                 160

His Met Ser Phe His Ala Tyr Ile Arg Lys Leu Thr Gly Gly Ala Asp
                165                 170                 175

Lys Gly Lys Phe Val Ala Leu Gly Asn Ile Ser Cys Lys Ile Lys Ser
            180                 185                 190

Gly Cys Glu Gly His Leu Pro Trp Pro Asn Gly Ile Cys Thr Lys Cys
        195                 200                 205

Gln Pro Ser Ala Ile Thr Leu Asn Arg Gln Lys Tyr Arg His Val Asp
    210                 215                 220

Asn Ile Met Phe Glu Asn His Thr Val Ala Asp Arg Phe Leu Asp Phe
225                 230                 235                 240

Trp Arg Lys Thr Gly Asn Gln His Phe Gly Tyr Leu Tyr Gly Arg Tyr
                245                 250                 255

Thr Glu His Lys Asp Ile Pro Leu Gly Ile Arg Ala Glu Val Ala Ala
            260                 265                 270

Ile Tyr Glu Pro Pro Gln Ile Gly Thr Gln Asn Ser Leu Glu Leu Leu
        275                 280                 285
```

```
Glu Asp Pro Lys Ala Glu Val Val Asp Glu Ile Ala Ala Lys Leu Gly
    290                 295                 300

Leu Arg Lys Val Gly Trp Ile Phe Thr Asp Leu Val Ser Glu Asp Thr
305                 310                 315                 320

Arg Lys Gly Thr Val Arg Tyr Ser Arg Asn Lys Asp Thr Tyr Phe Leu
                325                 330                 335

Ser Ser Glu Glu Cys Ile Thr Ala Gly Asp Phe Gln Asn Lys His Pro
            340                 345                 350

Asn Met Cys Arg Leu Ser Pro Asp Gly His Phe Gly Ser Lys Phe Val
        355                 360                 365

Thr Ala Val Ala Thr Gly Gly Pro Asp Asn Gln Val His Phe Glu Gly
    370                 375                 380

Tyr Gln Val Ser Asn Gln Cys Met Ala Leu Val Arg Asp Glu Cys Leu
385                 390                 395                 400

Leu Pro Cys Lys Asp Ala Pro Glu Leu Gly Tyr Ala Lys Glu Ser Ser
                405                 410                 415

Ser Glu Gln Tyr Val Pro Asp Val Phe Tyr Lys Asp Val Asp Lys Phe
            420                 425                 430

Gly Asn Glu Ile Thr Gln Leu Ala Arg Pro Leu Pro Val Glu Tyr Leu
        435                 440                 445

Ile Ile Asp Ile Thr Thr Thr Phe Pro Lys Asp Pro Val Tyr Thr Phe
    450                 455                 460

Ser Ile Ser Gln Asn Pro Phe Pro Ile Glu Asn Arg Asp Val Leu Gly
465                 470                 475                 480

Glu Thr Gln Asp Phe His Ser Leu Ala Thr Tyr Leu Ser Gln Asn Thr
                485                 490                 495

Ser Ser Val Phe Leu Asp Thr Ile Ser Asp Phe His Leu Leu Leu Phe
            500                 505                 510

Leu Val Thr Asn Glu Val Met Pro Leu Gln Asp Ser Ile Ser Leu Leu
        515                 520                 525

Leu Glu Ala Val Arg Thr Arg Asn Glu Glu Leu Ala Gln Thr Trp Lys
    530                 535                 540

Arg Ser Glu Gln Trp Ala Thr Ile Glu Gln Leu Cys Ser Thr Val Gly
545                 550                 555                 560

Gly Gln Leu Pro Gly Leu His Glu Tyr Gly Ala Val Gly Gly Ser Thr
                565                 570                 575

His Thr Ala Thr Ala Ala Met Trp Ala Cys Gln His Cys Thr Phe Met
            580                 585                 590

Asn Gln Pro Gly Thr Gly His Cys Glu Met Cys Ser Leu Pro Arg Thr
        595                 600                 605

<210> SEQ ID NO 22
<211> LENGTH: 1827
<212> TYPE: DNA
<213> ORGANISM: Homo sapiens

<400> SEQUENCE: 22
atggccgaga gcatcataat tcgtgtccag tccccggatg gagtgaagcg gatcacagca      60
acaaagagag aaacagcagc aacattttg aaaaaggttg caaggagtt tggcttccaa       120 aataatggct ctcggtttta catcaataga aacaagactg gagagataac agcctcctcc     180
aacaaatccc tcaacttgct aaaaatcaag catggcgatt tgttgttcct gtttccctcg     240
agccttgctg ggccctcatc tgaaatggag acgtcagttc caccgggctt caaagtcttt    300
```

| | |
|---|---|
| ggcgctccca acgtggtgga ggatgagatt gatcagtacc tcagcaaaca ggacgggaag | 360 |
| atttacagaa gccgagaccc acagctatgc cgccacggcc ctttggggaa atgcgtgcac | 420 |
| tgcgtccctc tagagccatt cgatgaggac tatctaaacc atctcgagcc tcccgtgaag | 480 |
| cacatgtcct tccacgccta catccggaag ctgactggag gggctgacaa ggggaagttt | 540 |
| gttgccctgg agaacatcag ctgcaagatt aagtcagggt gcgaggggca cctcccgtgg | 600 |
| ccgaatggca tctgtactaa gtgccagccg agcgccatca cgctgaacag acagaagtac | 660 |
| aggcatgtgg acaatatcat gtttgagaat cacaccgtcg ctgaccgctt tcttgacttc | 720 |
| tggagaaaga cagggaacca gcattttggg tacttatacg acggtacac ggagcacaaa | 780 |
| gacattcccc ttggcatcag ggctgaagtg gctgcgattt atgagccacc tcagattggt | 840 |
| acacagaaca gcttggagct tcttgaggat ccaaaagctg aagtggtcga tgaaattgct | 900 |
| gccaaacttg gcctgcggaa ggttggctgg atatttacag acctcgtctc agaagatacc | 960 |
| cgaaagggta ccgtccgcta cagtcgaaat aaggacacct atttcctaag ttcagaagag | 1020 |
| tgcatcactg caggagactt ccagaacaag catcccaaca tgtgccggct ctctccagac | 1080 |
| ggacattttg gatccaagtt tgttactgca gtggctacag tggtcctga caaccaagtc | 1140 |
| cactttgaag ggtaccaggt gtccaatcag tgtatggcac tggtccgtga tgagtgtttg | 1200 |
| ctgccatgca aggacgcccc ggagcttggc tacgccaagg agtctagcag tgagcagtac | 1260 |
| gtgcctgatg tgtttttataa ggacgtagac aagtttggca acgagatcac ccagctggcc | 1320 |
| cggcccctgc ctgtggagta tctcatcata gacatcacaa caactttccc caaggatcca | 1380 |
| gtttacactt tttctatttc gcaaaatcca tttcctattg aaaaccggga tgtattgggt | 1440 |
| gagacacagg acttccatag cttggccacc tatttgtctc agaatacctc atctgtgttc | 1500 |
| ttggatacca tctcagattt ccacctcttg ctgttcctgg tcaccaatga agttatgcct | 1560 |
| ctgcaggaca gcatcagctt gctgctggag gccgtgcgga ccagaaatga ggagctcgcc | 1620 |
| cagacatgga agaggtctga gcagtgggcc accatcgagc agctgtgcag cacagttggc | 1680 |
| gggcagctcc caggtctcca tgagtacggc gccgtcgggg gctccacaca cacggccact | 1740 |
| gcagccatgt gggcctgtca gcactgcacg ttcatgaacc agccaggcac aggccactgc | 1800 |
| gagatgtgca gcctccccag gacctag | 1827 |

<210> SEQ ID NO 23
<211> LENGTH: 307
<212> TYPE: PRT
<213> ORGANISM: Homo sapiens

<400> SEQUENCE: 23

Met Phe Ser Phe Asn Met Phe Asp His Pro Ile Pro Arg Val Phe Gln
1               5                   10                  15

Asn Arg Phe Ser Thr Gln Tyr Arg Cys Phe Ser Val Ser Met Leu Ala
            20                  25                  30

Gly Pro Asn Asp Arg Ser Asp Val Glu Lys Gly Lys Ile Ile Met
        35                  40                  45

Pro Pro Ser Ala Leu Asp Gln Leu Ser Arg Leu Asn Ile Thr Tyr Pro
    50                  55                  60

Met Leu Phe Lys Leu Thr Asn Lys Asn Ser Asp Arg Met Thr His Cys
65                  70                  75                  80

Gly Val Leu Glu Phe Val Ala Asp Glu Gly Ile Cys Tyr Leu Pro His
                85                  90                  95

```
Trp Met Met Gln Asn Leu Leu Leu Glu Glu Gly Gly Leu Val Gln Val
            100                 105                 110

Glu Ser Val Asn Leu Gln Val Ala Thr Tyr Ser Lys Phe Gln Pro Gln
        115                 120                 125

Ser Pro Asp Phe Leu Asp Ile Thr Asn Pro Lys Ala Val Leu Glu Asn
    130                 135                 140

Ala Leu Arg Asn Phe Ala Cys Leu Thr Thr Gly Asp Val Ile Ala Ile
145                 150                 155                 160

Asn Tyr Asn Glu Lys Ile Tyr Glu Leu Arg Val Met Glu Thr Lys Pro
                165                 170                 175

Asp Lys Ala Val Ser Ile Ile Glu Cys Asp Met Asn Val Asp Phe Asp
            180                 185                 190

Ala Pro Leu Gly Tyr Lys Glu Pro Glu Arg Gln Val Gln His Glu Glu
        195                 200                 205

Ser Thr Glu Gly Glu Ala Asp His Ser Gly Tyr Ala Gly Glu Leu Gly
    210                 215                 220

Phe Arg Ala Phe Ser Gly Ser Gly Asn Arg Leu Asp Gly Lys Lys Lys
225                 230                 235                 240

Gly Val Glu Pro Ser Pro Ser Pro Ile Lys Pro Gly Asp Ile Lys Arg
                245                 250                 255

Gly Ile Pro Asn Tyr Glu Phe Lys Leu Gly Lys Ile Thr Phe Ile Arg
            260                 265                 270

Asn Ser Arg Pro Leu Val Lys Lys Val Glu Glu Asp Glu Ala Gly Gly
        275                 280                 285

Arg Phe Val Ala Phe Ser Gly Glu Gly Gln Ser Leu Arg Lys Lys Gly
    290                 295                 300

Arg Lys Pro
305

<210> SEQ ID NO 24
<211> LENGTH: 924
<212> TYPE: DNA
<213> ORGANISM: Homo sapiens

<400> SEQUENCE: 24
atgttctctt tcaacatgtt cgaccaccct attcccaggg tcttccaaaa ccgcttctcc     60
acacagtacc gctgcttctc tgtgtccatg ctagcagggc ctaatgacag gtcagatgtg    120
gagaaaggag ggaagataat tatgccaccc tcggccctgg accaactcag ccgacttaac    180
attacctatc ccatgctgtt caaactgacc aataagaatt cggaccgcat gacgcattgt    240
ggcgtgctgg agtttgtggc tgatgagggc atctgctacc tcccacactg gatgatgcag    300
aacttactct tggaagaagg cggcctggtc caggtggaga cgtcaacct caagtggcc    360 acctactcca aattccaacc tcagagccct gacttcctgg acatcaccaa ccccaaagcc    420
gtattagaaa acgcacttag gaactttgcc tgtctgacca ccggggatgt gattgccatc    480
aactataatg aaaagatcta cgaactgcgt gtgatggaga ccaaaccga caaggcagtg    540 tccatcattg agtgtgacat gaacgtggac tttgatgctc ccctgggcta caagaaccc    600 gaaagacaag tccagcatga ggagtcgaca gaaggtgaag ccgaccacag tggctatgct    660
ggagagctgg gcttccgcgc tttctctgga tctggcaata gactggatgg aaagaagaa    720 ggggtagagc ccagcccctc cccaatcaag cctggagata ttaaagagg aattcccaat    780 tatgaattta acttggtaa gataactttc atcagaaatt cacgtcccct tgtcaaaaag    840
gttgaagagg atgaagctgg aggcagattc gtcgctttct ctggagaagg acagtcattg    900
```
cgtaaaaagg gaagaaagcc ctaa                                                 924

<210> SEQ ID NO 25
<211> LENGTH: 745
<212> TYPE: PRT
<213> ORGANISM: Homo sapiens

<400> SEQUENCE: 25

Met Ser Leu Lys Pro Arg Val Val Asp Phe Asp Glu Thr Trp Asn Lys
1               5                   10                  15

Leu Leu Thr Thr Ile Lys Ala Val Val Met Leu Glu Tyr Val Glu Arg
            20                  25                  30

Ala Thr Trp Asn Asp Arg Phe Ser Asp Ile Tyr Ala Leu Cys Val Ala
        35                  40                  45

Tyr Pro Glu Pro Leu Gly Glu Arg Leu Tyr Thr Glu Thr Lys Ile Phe
    50                  55                  60

Leu Glu Asn His Val Arg His Leu His Lys Arg Val Leu Glu Ser Glu
65                  70                  75                  80

Glu Gln Val Leu Val Met Tyr His Arg Tyr Trp Glu Glu Tyr Ser Lys
                85                  90                  95

Gly Ala Asp Tyr Met Asp Cys Leu Tyr Arg Tyr Leu Asn Thr Gln Phe
            100                 105                 110

Ile Lys Lys Asn Lys Leu Thr Glu Ala Asp Leu Gln Tyr Gly Tyr Gly
        115                 120                 125

Gly Val Asp Met Asn Glu Pro Leu Met Glu Ile Gly Glu Leu Ala Leu
    130                 135                 140

Asp Met Trp Arg Lys Leu Met Val Glu Pro Leu Gln Ala Ile Leu Ile
145                 150                 155                 160

Arg Met Leu Leu Arg Glu Ile Lys Asn Asp Arg Gly Gly Glu Asp Pro
                165                 170                 175

Asn Gln Lys Val Ile His Gly Val Ile Asn Ser Phe Val His Val Glu
            180                 185                 190

Gln Tyr Lys Lys Lys Phe Pro Leu Lys Phe Tyr Gln Glu Ile Phe Glu
        195                 200                 205

Ser Pro Phe Leu Thr Glu Thr Gly Glu Tyr Tyr Lys Gln Glu Ala Ser
    210                 215                 220

Asn Leu Leu Gln Glu Ser Asn Cys Ser Gln Tyr Met Glu Lys Val Leu
225                 230                 235                 240

Gly Arg Leu Lys Asp Glu Glu Ile Arg Cys Arg Lys Tyr Leu His Pro
                245                 250                 255

Ser Ser Tyr Thr Lys Val Ile His Glu Cys Gln Gln Arg Met Val Ala
            260                 265                 270

Asp His Leu Gln Phe Leu His Ala Glu Cys His Asn Ile Ile Arg Gln
        275                 280                 285

Glu Lys Lys Asn Asp Met Ala Asn Met Tyr Val Leu Leu Arg Ala Val
    290                 295                 300

Ser Thr Gly Leu Pro His Met Ile Gln Glu Leu Gln Asn His Ile His
305                 310                 315                 320

Asp Glu Gly Leu Arg Ala Thr Ser Asn Leu Thr Gln Glu Asn Met Pro
                325                 330                 335

Thr Leu Phe Val Glu Ser Val Leu Glu Val His Gly Lys Phe Val Gln
            340                 345                 350

Leu Ile Asn Thr Val Leu Asn Gly Asp Gln His Phe Met Ser Ala Leu
        355                 360                 365

```
Asp Lys Ala Leu Thr Ser Val Val Asn Tyr Arg Glu Pro Lys Ser Val
        370                 375                 380

Cys Lys Ala Pro Glu Leu Leu Ala Lys Tyr Cys Asp Asn Leu Leu Lys
385                 390                 395                 400

Lys Ser Ala Lys Gly Met Thr Glu Asn Glu Val Glu Asp Arg Leu Thr
            405                 410                 415

Ser Phe Ile Thr Val Phe Lys Tyr Ile Asp Asp Lys Asp Val Phe Gln
        420                 425                 430

Lys Phe Tyr Ala Arg Met Leu Ala Lys Arg Leu Ile His Gly Leu Ser
            435                 440                 445

Met Ser Met Asp Ser Glu Glu Ala Met Ile Asn Lys Leu Lys Gln Ala
450                 455                 460

Cys Gly Tyr Glu Phe Thr Ser Lys Leu His Arg Met Tyr Thr Asp Met
465                 470                 475                 480

Ser Val Ser Ala Asp Leu Asn Asn Lys Phe Asn Asn Phe Ile Lys Asn
            485                 490                 495

Gln Asp Thr Val Ile Asp Leu Gly Ile Ser Phe Gln Ile Tyr Val Leu
        500                 505                 510

Gln Ala Gly Ala Trp Pro Leu Thr Gln Ala Pro Ser Ser Thr Phe Ala
    515                 520                 525

Ile Pro Gln Glu Leu Glu Lys Ser Val Gln Met Phe Glu Leu Phe Tyr
530                 535                 540

Ser Gln His Phe Ser Gly Arg Lys Leu Thr Trp Leu His Tyr Leu Cys
545                 550                 555                 560

Thr Gly Glu Val Lys Met Asn Tyr Leu Gly Lys Pro Tyr Val Ala Met
                565                 570                 575

Val Thr Thr Tyr Gln Met Ala Val Leu Leu Ala Phe Asn Asn Ser Glu
            580                 585                 590

Thr Val Ser Tyr Lys Glu Leu Gln Asp Ser Thr Gln Met Asn Glu Lys
        595                 600                 605

Glu Leu Thr Lys Thr Ile Lys Ser Leu Leu Asp Val Lys Met Ile Asn
    610                 615                 620

His Asp Ser Glu Lys Glu Asp Ile Asp Ala Glu Ser Ser Phe Ser Leu
625                 630                 635                 640

Asn Met Asn Phe Ser Ser Lys Arg Thr Lys Phe Lys Ile Thr Thr Ser
                645                 650                 655

Met Gln Lys Asp Thr Pro Gln Glu Met Glu Gln Thr Arg Ser Ala Val
            660                 665                 670

Asp Glu Asp Arg Lys Met Tyr Leu Gln Ala Ala Ile Val Arg Ile Met
        675                 680                 685

Lys Ala Arg Lys Val Leu Arg His Asn Ala Leu Ile Gln Glu Val Ile
    690                 695                 700

Ser Gln Ser Arg Ala Arg Phe Asn Pro Ser Ile Ser Met Ile Lys Lys
705                 710                 715                 720

Cys Ile Glu Val Leu Ile Asp Lys Gln Tyr Ile Glu Arg Ser Gln Ala
                725                 730                 735

Ser Ala Asp Glu Tyr Ser Tyr Val Ala
            740                 745

<210> SEQ ID NO 26
<211> LENGTH: 2238
<212> TYPE: DNA
<213> ORGANISM: Homo sapiens
```

```
<400> SEQUENCE: 26
atgtctttga aaccaagagt agtagatttt gatgaaacat ggaacaaact tttgacgaca      60
ataaaagccg tggtcatgtt ggaatacgtc gaaagagcaa catggaatga ccgtttctca     120
gatatctatg ctttatgtgt ggcctatcct gaacccttg gagaaagact ttatacagaa      180
actaagattt ttttggaaaa tcatgttcgg catttgcata agagagtttt ggagtcagaa     240
gaacaagtac ttgttatgta cataggtac tgggaagaat acagcaaggg tgcagactat     300
atggactgct tatataggta tctcaacacc cagtttatta aaagaataa attaacagaa      360
gcggaccttc agtatggcta tggtggtgta gatatgaatg aaccacttat ggaaatagga    420
gagctagcat tggatatgtg gaggaaattg atggttgaac cacttcaggc catccttatc    480
cgaatgctgc tccgagaaat caaaaatgat cgtggtggag aagacccaaa ccagaaagta    540
atccatgggg ttattaactc ctttgttcat gttgaacagt ataagaaaaa attcccctta   600
aagtttatc aggaaatttt tgagtctccc tttctgactg aaacaggaga gtattacaaa     660
caagaagctt caaatttatt acaagaatca aactgctcac agtatatgga aaaggttcta    720
ggtagattaa aagatgaaga aattcgatgt cgaaaatacc tacatccaag ttcatatact    780
aaggtgattc atgaatgtca acaacgaatg gtagcagacc acttacagtt tttacatgca    840
gaatgtcata atataattcg acaagagaaa aaaaatgaca tggcaaatat gtacgtctta    900
ctccgtgctg tgtccactgg tttacctcat atgattcagg agctgcaaaa ccacatccat    960
gatgagggcc ttcgagcaac cagcaaccct actcaggaaa acatgccaac actatttgtg   1020
gagtcagttt tggaagtgca tggtaaattt gttcagctta tcaacactgt tttgaatggt    1080
gatcagcatt ttatgagtgc gttggataag gcccttacgt cagttgtaaa ttacagagaa    1140
cctaagtctg tttgcaaagc acctgaactg cttgctaagt actgtgacaa cttactgaag   1200
aagtcagcga aagggatgac agagaatgaa gtggaagaca ggctcacgag cttcatcaca    1260
gtgttcaaat acattgatga caaggacgtc tttcaaaagt tctacgcaag aatgctggca   1320
aaacgtttaa ttcatgggtt atccatgtct atggactctg aagaagccat gatcaacaaa   1380
ttaaagcaag cctgtggtta tgagtttacc agcaagctac atcggatgta tacagatatg   1440
agtgtcagcg ctgatctcaa caataagttc aacaatttta tcaaaaacca agacacagta   1500
atagatttgg gaattagttt tcaaatatat gttctacagg ctggtgcgtg gcctcttact   1560
caggctcctt catctacgtt tgcaattccc caggaattag aaaaaagtgt acagatgttt   1620
gaattatttt atagccaaca tttcagtgga aggaaactta catggttaca ttatctgtgt   1680
acaggtgaag ttaaaatgaa ctatttgggc aaaccatatg tagccatggt tacaacatac   1740
caaatggcag ttcttcttgc ctttaacaac agtgaaactg tcagttataa agagcttcag    1800
gacagcactc agatgaatga aaaggaactg acaaaaacaa tcaaatcatt acttgatgtg    1860
aaaatgatta accatgattc agaaaaggaa gatattgatg cagaatcttc gtttttcatta   1920
aatatgaact ttagcagtaa aagaacaaaa tttaaaatta ctacatcaat gcagaaagac   1980
acaccacaag aaatggagca gactagaagt gcagttgatg aggaccggaa aatgtatctc    2040
caagctgcta tagttcgtat catgaaagca cgaaaagtgc ttcggcacaa tgcccttatt    2100
caagaggtga ttagccagtc aagagctagg tttaatccca gtatcagcat gattaagaag   2160
tgtattgaag ttctgataga caaacaatac atagaacgca gccaggcgtc ggcagatgaa   2220
tacagctacg tcgcgtga                                                  2238
```

<210> SEQ ID NO 27
<211> LENGTH: 72
<212> TYPE: PRT
<213> ORGANISM: Homo sapiens

<400> SEQUENCE: 27

Asp Asp Gln Leu Leu Asp Asp Gly Lys Thr Leu Gly Glu Cys Gly Phe
1               5                   10                  15

Thr Ser Gln Thr Ala Arg Pro Gln Ala Pro Ala Thr Val Gly Leu Ala
            20                  25                  30

Phe Arg Ala Asp Asp Thr Phe Glu Ala Leu Cys Ile Glu Pro Phe Ser
        35                  40                  45

Ser Pro Pro Glu Leu Pro Asp Val Met Lys Pro Gln Asp Ser Gly Ser
    50                  55                  60

Ser Ala Asn Glu Gln Ala Val Gln
65                  70

<210> SEQ ID NO 28
<211> LENGTH: 219
<212> TYPE: DNA
<213> ORGANISM: Homo sapiens

<400> SEQUENCE: 28
gatgaccaac tcttggatga tggcaagaca ctgggcgagt gtggcttcac cagtcaaaca      60
gcacggccac aggccccagc cacagtgggg ctggccttcc gggcagatga cacctttgag     120
gccctgtgca tcgagccgtt ttccagcccg ccagagctgc ccgatgtgat gaagccccag     180
gactcgggaa gcagtgccaa tgaacaagcc gtgcagtga                            219

<210> SEQ ID NO 29
<211> LENGTH: 112
<212> TYPE: PRT
<213> ORGANISM: Homo sapiens

<400> SEQUENCE: 29

Met Asp Gly Glu Glu Lys Thr Tyr Gly Gly Cys Glu Gly Pro Asp Ala
1               5                   10                  15

Met Tyr Val Lys Leu Ile Ser Ser Asp Gly His Glu Phe Ile Val Lys
            20                  25                  30

Arg Glu His Ala Leu Thr Ser Gly Thr Ile Lys Ala Met Leu Ser Gly
        35                  40                  45

Pro Gly Gln Phe Ala Glu Asn Glu Thr Asn Glu Val Asn Phe Arg Glu
    50                  55                  60

Ile Pro Ser His Val Leu Ser Lys Val Cys Met Tyr Phe Thr Tyr Lys
65                  70                  75                  80

Val Arg Tyr Thr Asn Ser Ser Thr Glu Ile Pro Glu Phe Pro Ile Ala
                85                  90                  95

Pro Glu Ile Ala Leu Glu Leu Leu Met Ala Ala Asn Phe Leu Asp Cys
            100                 105                 110

<210> SEQ ID NO 30
<211> LENGTH: 339
<212> TYPE: DNA
<213> ORGANISM: Homo sapiens

<400> SEQUENCE: 30
atggatggag aggagaaaac ctatggtggc tgtgaaggac ctgatgccat gtatgtcaaa      60
ttgatatcat ctgatggcca tgaatttatt gtaaaaagag aacatgcatt aacatcaggc     120

```
acgataaaag ccatgttgag tggcccaggt cagtttgctg agaacgaaac caatgaggtc      180
aattttagag agataccttc acatgtgcta tcgaaagtat gcatgtattt tacgtacaag      240
gttcgctaca ctaacagctc caccgagatt cctgaattcc caattgcacc tgaaattgca      300
ctggaactgc tgatggctgc gaacttctta gattgttaa                             339
```

<210> SEQ ID NO 31
<211> LENGTH: 213
<212> TYPE: PRT
<213> ORGANISM: Homo sapiens

<400> SEQUENCE: 31

```
Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
    130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
            180                 185                 190

Asn Val Gln Lys Asp Leu Glu Arg Leu Thr Gln Glu Arg Ile Ala His
        195                 200                 205

Gln Arg Met Gly Asp
    210
```

<210> SEQ ID NO 32
<211> LENGTH: 642
<212> TYPE: DNA
<213> ORGANISM: Homo sapiens

<400> SEQUENCE: 32

```
atgccccgga gggcggagaa ctgggacgag gccgaggtag gcgcggagga ggcaggcgtc      60
gaagagtacg gccctgaaga agacggcggg gaggagtcgg gcgccgagga gtccggcccg      120
gaagagtccg gcccggagga actgggcgcc gaggaggaga tggaggccgg gcggccgcgg      180
cccgtgctgc gctcggtgaa ctcgcgcgag ccctcccagg tcatcttctg caatcgcagt      240
ccgcgcgtcg tgctgcccgt atggctcaac ttcgacggcg agccgcagcc ctacccaacg      300
ctgccgcctg gcacgggccg ccgcatccac agctaccgag gtcacctttg gctcttcaga      360
gatgcaggga cacacgatgg gcttctggtt aaccaaactg aattatttgt gccatctctc      420
```

```
aatgttgacg gacagcctat ttttgccaat atcacactgc cagtgtatac tctgaaagag      480
cgatgcctcc aggttgtccg gagcctagtc aagcctgaga attacaggag actggacatc      540
gtcaggtcgc tctacgaaga tctggaagac cacccaaatg tgcagaaaga cctggagcgg      600
ctgacacagg agcgcattgc acatcaacgg atgggagatt ga                         642
```

```
<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
cugaugacca gcaacuugat t                                                21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
cauucuaucc ucuagaggau gtt                                              23

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatgtaatgc tcccctcacc caac                                             24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cactgggact attaggctca ggtg                                             24

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggacacgga caggattgac agattg                                           26
```

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcacacgctg agccagtcag tgtag                                           25

<210> SEQ ID NO 39
<211> LENGTH: 12
<212> TYPE: PRT
<213> ORGANISM: Homo sapiens

<400> SEQUENCE: 39

Val Glu Ser Glu Asp Thr Ser Ser Leu Phe Asp Lys
1               5                   10

<210> SEQ ID NO 40
<211> LENGTH: 14
<212> TYPE: PRT
<213> ORGANISM: Homo sapiens

<400> SEQUENCE: 40

Ser Ser Ala Asp Pro Ala Leu Asn Gln Glu Val Ala Leu Lys
1               5                   10

<210> SEQ ID NO 41
<211> LENGTH: 9
<212> TYPE: PRT
<213> ORGANISM: Homo sapiens

<400> SEQUENCE: 41

Leu Phe Ala Glu Asp Thr Glu Ala Lys
1               5

<210> SEQ ID NO 42
<211> LENGTH: 12
<212> TYPE: PRT
<213> ORGANISM: Homo sapiens

<400> SEQUENCE: 42

Ser Pro Asn Val Leu Ser Val Ala Leu Ser Gln Arg
1               5                   10

<210> SEQ ID NO 43
<211> LENGTH: 11
<212> TYPE: PRT
<213> ORGANISM: Homo sapiens

<400> SEQUENCE: 43

Thr Thr Val Pro Glu Glu Glu Leu Asn Pro Lys
1               5                   10

<210> SEQ ID NO 44
<211> LENGTH: 9
<212> TYPE: PRT
<213> ORGANISM: Homo sapiens

<400> SEQUENCE: 44

Ile Leu Ala Leu Gln Asn Ala Gln Arg
1               5

```
<210> SEQ ID NO 45
<211> LENGTH: 12
<212> TYPE: PRT
<213> ORGANISM: Homo sapiens

<400> SEQUENCE: 45

Thr Ile Ile Leu Ile Pro Ser Asp Leu Ala Cys Arg
1               5                   10

<210> SEQ ID NO 46
<211> LENGTH: 10
<212> TYPE: PRT
<213> ORGANISM: Homo sapiens

<400> SEQUENCE: 46

Asn Leu Leu Gln Gly Glu Glu Leu Leu Arg
1               5                   10
```